United States Patent
Drury et al.

(10) Patent No.: US 11,911,279 B2
(45) Date of Patent: *Feb. 27, 2024

(54) POSTERIOR STABILIZED PROSTHESIS SYSTEM

(71) Applicant: Zimmer, Inc., Warsaw, IN (US)

(72) Inventors: Nick Drury, Warsaw, IN (US); Jeff Blaylock, Fort Wayne, IN (US)

(73) Assignee: Zimmer, Inc., Warsaw, IN (US)

( * ) Notice: Subject to any disclaimer, the term of this patent is extended or adjusted under 35 U.S.C. 154(b) by 688 days.

This patent is subject to a terminal disclaimer.

(21) Appl. No.: 17/068,435

(22) Filed: Oct. 12, 2020

(65) Prior Publication Data
US 2021/0022875 A1    Jan. 28, 2021

Related U.S. Application Data

(63) Continuation of application No. 16/389,381, filed on Apr. 19, 2019, now Pat. No. 10,835,380.
(Continued)

(51) Int. Cl.
*A61F 2/38* (2006.01)
*A61F 2/30* (2006.01)

(52) U.S. Cl.
CPC ............ *A61F 2/3836* (2013.01); *A61F 2/389* (2013.01); *A61F 2/3859* (2013.01); *A61F 2002/30518* (2013.01); *A61F 2002/3863* (2013.01)

(58) Field of Classification Search
CPC ....... A61F 2/3836; A61F 2/3859; A61F 2/389
See application file for complete search history.

(56) References Cited

U.S. PATENT DOCUMENTS

| 3,774,244 A | 11/1973 | Walker |
| 4,016,606 A | 4/1977 | Murray et al. |
| (Continued) | | |

FOREIGN PATENT DOCUMENTS

| AU | 2011343440 B2 | 4/2014 |
| AU | 2011286306 B2 | 10/2014 |
| (Continued) | | |

OTHER PUBLICATIONS

U.S. Appl. No. 17/866,151, filed Jul. 15, 2022, Implants for Adding Joint Inclination to a Knee Arthroplasty.
(Continued)

*Primary Examiner* — Brian A Dukert
(74) *Attorney, Agent, or Firm* — SCHWEGMAN LUNDBERG & WOESSNER, P.A.

(57) ABSTRACT

According to one example, a posterior-stabilized femoral prosthesis for a knee arthroplasty. The femoral prosthesis can include medial and lateral condyles, a femoral cam and a recess. The medial and lateral condyles can be shaped to articulate with a tibial articular surface of a tibial bearing component through a range of motion, in which full extension corresponds to zero degrees flexion of a knee joint and positive flexion corresponds to greater than zero degrees flexion of the knee joint. In a sagittal plane, the medial and lateral condyles can define medial and lateral multi-radius curves, respectively. The medial multi-radius curve can have a single common radius swept through a first angular extent to define a single arc length that extends from between substantially −20 degrees flexion to substantially 90 degrees flexion, inclusive.

19 Claims, 14 Drawing Sheets

Related U.S. Application Data

(60) Provisional application No. 62/664,500, filed on Apr. 30, 2018.

(56) References Cited

U.S. PATENT DOCUMENTS

| | | |
|---|---|---|
| 4,257,129 A | 3/1981 | Volz |
| 4,340,978 A | 7/1982 | Buechel et al. |
| 4,501,266 A | 2/1985 | McDaniel |
| 4,568,348 A | 2/1986 | Johnson et al. |
| 4,673,408 A | 6/1987 | Grobbelaar |
| 4,711,639 A | 12/1987 | Grundei |
| 4,714,474 A | 12/1987 | Brooks, Jr. et al. |
| 4,759,767 A | 7/1988 | Lacey |
| 4,769,040 A | 9/1988 | Wevers |
| 4,770,661 A | 9/1988 | Oh |
| 4,795,468 A | 1/1989 | Hodorek et al. |
| 4,822,365 A | 4/1989 | Walker et al. |
| 4,936,853 A | 6/1990 | Fabian et al. |
| 4,944,756 A | 7/1990 | Kenna |
| 4,944,757 A | 7/1990 | Martinez et al. |
| 4,950,298 A | 8/1990 | Gustilo et al. |
| 4,959,071 A | 9/1990 | Brown et al. |
| 4,963,152 A | 10/1990 | Hofmann et al. |
| 5,007,933 A | 4/1991 | Sidebotham et al. |
| 5,047,057 A | 9/1991 | Lawes |
| 5,047,058 A | 9/1991 | Roberts et al. |
| 5,059,216 A | 10/1991 | Winters |
| 5,061,271 A | 10/1991 | Van Zile |
| 5,071,438 A | 12/1991 | Jones et al. |
| 5,108,442 A | 4/1992 | Smith |
| 5,116,375 A | 5/1992 | Hofmann |
| 5,133,758 A | 7/1992 | Hollister |
| 5,137,536 A | 8/1992 | Koshino |
| 5,147,405 A | 9/1992 | Van Zile |
| 5,171,283 A | 12/1992 | Pappas et al. |
| 5,192,328 A | 3/1993 | Winters |
| 5,194,066 A | 3/1993 | Van Zile |
| 5,197,488 A | 3/1993 | Kovacevic |
| 5,219,362 A | 6/1993 | Tuke et al. |
| 5,226,915 A | 7/1993 | Bertin |
| 5,236,461 A | 8/1993 | Forte |
| 5,246,459 A | 9/1993 | Elias |
| 5,271,737 A | 12/1993 | Baldwin et al. |
| 5,275,603 A | 1/1994 | Ferrante et al. |
| 5,282,861 A | 2/1994 | Kaplan |
| 5,282,868 A | 2/1994 | Bahler |
| 5,282,870 A | 2/1994 | Moser et al. |
| 5,290,313 A | 3/1994 | Heldreth |
| 5,310,480 A | 5/1994 | Vidueira |
| 5,326,361 A | 7/1994 | Hollister |
| 5,344,460 A | 9/1994 | Turanyi et al. |
| 5,344,461 A | 9/1994 | Phlipot |
| 5,360,016 A | 11/1994 | Kovacevic |
| 5,364,402 A | 11/1994 | Mumme et al. |
| 5,370,699 A | 12/1994 | Hood et al. |
| 5,387,239 A | 2/1995 | Bianco et al. |
| 5,387,240 A | 2/1995 | Pottenger et al. |
| 5,395,401 A | 3/1995 | Bahler |
| 5,405,396 A | 4/1995 | Heldreth et al. |
| 5,413,604 A | 5/1995 | Hodge |
| 5,413,605 A | 5/1995 | Ashby et al. |
| 5,425,775 A | 6/1995 | Kovacevic et al. |
| 5,445,642 A | 8/1995 | McNulty et al. |
| 5,458,637 A | 10/1995 | Hayes |
| 5,470,354 A | 11/1995 | Hershberger et al. |
| 5,489,311 A | 2/1996 | Cipolletti |
| 5,507,820 A | 4/1996 | Pappas |
| 5,549,688 A | 8/1996 | Ries et al. |
| 5,556,433 A | 9/1996 | Gabriel et al. |
| 5,571,194 A | 11/1996 | Gabriel |
| 5,609,639 A | 3/1997 | Walker |
| 5,609,641 A | 3/1997 | Johnson et al. |
| 5,609,643 A | 3/1997 | Colleran et al. |
| 5,609,645 A | 3/1997 | Vinciguerra |
| 5,613,970 A | 3/1997 | Houston et al. |
| 5,656,785 A | 8/1997 | Trainor et al. |
| 5,658,341 A | 8/1997 | Delfosse |
| 5,658,342 A | 8/1997 | Draganich et al. |
| 5,658,344 A | 8/1997 | Hurlburt |
| 5,683,470 A | 11/1997 | Johnson et al. |
| 5,702,463 A | 12/1997 | Pothier et al. |
| 5,702,464 A | 12/1997 | Lackey et al. |
| 5,733,292 A | 3/1998 | Gustilo et al. |
| 5,755,801 A | 5/1998 | Walker et al. |
| 5,755,802 A | 5/1998 | Gerber |
| 5,776,200 A | 7/1998 | Johnson et al. |
| 5,782,925 A | 7/1998 | Collazo et al. |
| 5,824,100 A | 10/1998 | Kester et al. |
| 5,824,102 A | 10/1998 | Buscayret |
| 5,824,103 A | 10/1998 | Williams |
| 5,871,539 A | 2/1999 | Pappas |
| 5,871,541 A | 2/1999 | Gerber |
| 5,871,543 A | 2/1999 | Hofmann |
| 5,871,545 A | 2/1999 | Goodfellow et al. |
| 5,879,394 A | 3/1999 | Ashby et al. |
| 5,906,643 A | 5/1999 | Walker |
| 5,911,723 A | 6/1999 | Ashby et al. |
| 5,928,286 A | 7/1999 | Ashby et al. |
| 5,964,808 A | 10/1999 | Blaha et al. |
| 5,968,099 A | 10/1999 | Badorf et al. |
| 5,976,147 A | 11/1999 | LaSalle et al. |
| 6,004,351 A | 12/1999 | Tomita et al. |
| 6,004,352 A | 12/1999 | Buni |
| 6,010,534 A | 1/2000 | O'neil et al. |
| 6,013,103 A | 1/2000 | Kaufman et al. |
| 6,039,764 A | 3/2000 | Pottenger et al. |
| 6,068,658 A | 5/2000 | Insall et al. |
| 6,074,425 A | 6/2000 | Pappas |
| 6,080,195 A | 6/2000 | Colleran et al. |
| 6,090,144 A | 7/2000 | Letot et al. |
| 6,102,954 A | 8/2000 | Albrektsson et al. |
| 6,102,955 A | 8/2000 | Mendes et al. |
| 6,123,728 A | 9/2000 | Brosnahan et al. |
| 6,123,729 A | 9/2000 | Insall et al. |
| 6,126,692 A | 10/2000 | Robie et al. |
| 6,143,034 A | 11/2000 | Burrows |
| 6,197,064 B1 | 3/2001 | Haines et al. |
| 6,203,576 B1 | 3/2001 | Afriat et al. |
| 6,206,927 B1 | 3/2001 | Fell et al. |
| 6,210,443 B1 | 4/2001 | Marceaux et al. |
| 6,217,618 B1 | 4/2001 | Hileman |
| RE37,277 E | 7/2001 | Baldwin et al. |
| 6,258,127 B1 | 7/2001 | Schmotzer |
| 6,306,172 B1 | 10/2001 | O'Neil et al. |
| 6,325,828 B1 | 12/2001 | Dennis et al. |
| 6,379,388 B1 | 4/2002 | Ensign et al. |
| 6,406,497 B2 | 6/2002 | Takei |
| 6,413,279 B1 | 7/2002 | Metzger et al. |
| 6,428,577 B1 | 8/2002 | Evans et al. |
| 6,436,145 B1 | 8/2002 | Miller |
| 6,485,519 B2 | 11/2002 | Meyers et al. |
| 6,491,726 B2 | 12/2002 | Pappas |
| 6,506,215 B1 | 1/2003 | Letot et al. |
| 6,506,216 B1 | 1/2003 | McCue et al. |
| 6,558,426 B1 | 5/2003 | Masini |
| 6,607,559 B2 | 8/2003 | Ralph et al. |
| 6,623,526 B1 | 9/2003 | Lloyd |
| 6,632,225 B2 | 10/2003 | Sanford et al. |
| 6,660,039 B1 | 12/2003 | Evans et al. |
| 6,702,821 B2 | 3/2004 | Bonutti |
| 6,709,461 B2 | 3/2004 | O'neil et al. |
| 6,743,258 B1 | 6/2004 | Keller |
| 6,755,864 B1 | 6/2004 | Brack et al. |
| 6,770,078 B2 | 8/2004 | Bonutti |
| 6,869,448 B2 | 3/2005 | Tuke et al. |
| 6,916,340 B2 | 7/2005 | Metzger et al. |
| 6,923,832 B1 | 8/2005 | Sharkey et al. |
| 6,942,670 B2 | 9/2005 | Heldreth et al. |
| 6,953,479 B2 | 10/2005 | Carson et al. |
| 6,974,481 B1 | 12/2005 | Carson |
| 6,986,791 B1 | 1/2006 | Metzger |
| 7,025,788 B2 | 4/2006 | Metzger et al. |
| 7,060,074 B2 | 6/2006 | Rosa et al. |
| 7,081,137 B1 | 7/2006 | Servidio |

(56) References Cited

U.S. PATENT DOCUMENTS

| | | |
|---|---|---|
| 7,083,652 B2 | 8/2006 | McCue et al. |
| 7,153,326 B1 | 12/2006 | Metzger |
| 7,160,330 B2 | 1/2007 | Axelson, Jr. et al. |
| 7,189,262 B2 | 3/2007 | Hayes, Jr. et al. |
| 7,261,740 B2 | 8/2007 | Tuttle |
| 7,264,635 B2 | 9/2007 | Suguro |
| 7,294,149 B2 | 11/2007 | Hozack et al. |
| 7,309,362 B2 | 12/2007 | Yasuda et al. |
| 7,309,363 B2 | 12/2007 | Dietz |
| 7,326,252 B2 | 2/2008 | Otto et al. |
| 7,351,263 B2 | 4/2008 | Afriat |
| 7,364,581 B2 | 4/2008 | Michalowicz |
| 7,412,897 B2 | 8/2008 | Crottet et al. |
| 7,413,577 B1 | 8/2008 | Servidio |
| 7,442,196 B2 | 10/2008 | Fisher et al. |
| 7,445,639 B2 | 11/2008 | Metzger et al. |
| 7,488,330 B2 | 2/2009 | Stad |
| 7,497,874 B1 | 3/2009 | Metzger et al. |
| 7,513,912 B2 | 4/2009 | Hayes, Jr. et al. |
| 7,544,211 B2 | 6/2009 | Rochetin |
| 7,547,327 B2 | 6/2009 | Collazo |
| 7,575,602 B2 | 8/2009 | Amirouche et al. |
| 7,578,821 B2 | 8/2009 | Fisher et al. |
| 7,585,328 B2 | 9/2009 | Haas |
| 7,587,945 B2 | 9/2009 | Crottet et al. |
| 7,591,854 B2 | 9/2009 | Wasielewski |
| 7,625,407 B2 | 12/2009 | Akizuki |
| 7,628,818 B2 | 12/2009 | Hazebrouck et al. |
| 7,632,283 B2 | 12/2009 | Heldreth |
| 7,632,314 B2 | 12/2009 | Dietz |
| 7,635,390 B1 | 12/2009 | Bonutti |
| 7,678,152 B2 | 3/2010 | Suguro et al. |
| 7,695,519 B2 | 4/2010 | Collazo |
| 7,695,520 B2 | 4/2010 | Metzger et al. |
| 7,731,755 B2 * | 6/2010 | Wyss ............... A61F 2/3868 623/20.27 |
| 7,776,085 B2 | 8/2010 | Bernero et al. |
| 7,837,691 B2 | 11/2010 | Cordes et al. |
| 7,850,698 B2 | 12/2010 | Straszheim-Morley et al. |
| 8,012,216 B2 | 9/2011 | Metzger |
| 8,065,927 B2 | 11/2011 | Crottet et al. |
| 8,105,386 B2 | 1/2012 | Perrone, Jr. et al. |
| 8,141,437 B2 | 3/2012 | Amirouche et al. |
| 8,152,853 B2 | 4/2012 | Belcher |
| 8,163,028 B2 | 4/2012 | Metzger et al. |
| 8,187,280 B2 | 5/2012 | May et al. |
| 8,197,549 B2 | 6/2012 | Amirouche et al. |
| 8,211,041 B2 | 7/2012 | Fisher et al. |
| 8,245,583 B2 | 8/2012 | Stein |
| 8,268,006 B2 | 9/2012 | Meyers et al. |
| 8,317,870 B2 | 11/2012 | Wagner et al. |
| 8,328,873 B2 | 12/2012 | Metzger et al. |
| 8,366,782 B2 | 2/2013 | Wright |
| 8,491,589 B2 | 7/2013 | Fisher et al. |
| 8,506,571 B2 | 8/2013 | Chana et al. |
| RE44,476 E | 9/2013 | Meyers et al. |
| 8,568,486 B2 | 10/2013 | Wentorf et al. |
| 8,574,304 B2 | 11/2013 | Wentorf et al. |
| 8,591,594 B2 | 11/2013 | Parisi et al. |
| 8,603,101 B2 | 12/2013 | Claypool et al. |
| 8,613,775 B2 | 12/2013 | Wentorf et al. |
| 8,617,250 B2 | 12/2013 | Metzger |
| 8,628,580 B2 | 1/2014 | Sanford et al. |
| 8,690,954 B2 | 4/2014 | Parisi et al. |
| 8,740,984 B2 | 6/2014 | Hartdegen et al. |
| 8,758,444 B2 | 6/2014 | Wentorf et al. |
| 8,764,838 B2 | 7/2014 | Parisi et al. |
| 8,764,840 B2 | 7/2014 | Sanford et al. |
| 8,795,282 B2 | 8/2014 | Earl et al. |
| 8,808,387 B2 | 8/2014 | Hawkins et al. |
| 8,858,643 B2 | 10/2014 | Parisi et al. |
| 8,932,298 B2 | 1/2015 | Colquhoun et al. |
| 8,932,365 B2 | 1/2015 | Parisi et al. |
| 8,979,847 B2 | 3/2015 | Belcher et al. |
| 8,979,936 B2 | 3/2015 | White et al. |
| 8,998,997 B2 | 4/2015 | Ries et al. |
| 9,011,459 B2 | 4/2015 | Claypool et al. |
| 9,072,607 B2 | 7/2015 | Parisi et al. |
| 9,131,945 B2 | 9/2015 | Aram et al. |
| 9,149,206 B2 | 10/2015 | Claypool et al. |
| 9,173,744 B2 | 11/2015 | Donno et al. |
| 9,186,255 B2 | 11/2015 | Parisi et al. |
| 9,192,480 B2 | 11/2015 | Wentorf et al. |
| 9,204,970 B2 | 12/2015 | Parisi et al. |
| 9,283,082 B2 | 3/2016 | Sanford et al. |
| 9,295,557 B2 | 3/2016 | Wentorf et al. |
| 9,295,558 B2 | 3/2016 | Parisi et al. |
| 9,308,095 B2 | 4/2016 | Parisi et al. |
| 9,308,096 B2 | 4/2016 | Wentorf et al. |
| 9,314,343 B2 | 4/2016 | Parisi et al. |
| 9,381,090 B2 | 7/2016 | Wentorf et al. |
| 9,427,337 B2 | 8/2016 | Claypool et al. |
| 9,539,116 B2 | 1/2017 | Claypool et al. |
| 9,592,133 B2 | 3/2017 | Toler et al. |
| 9,597,090 B2 | 3/2017 | Claypool et al. |
| 9,655,728 B2 | 5/2017 | Parisi et al. |
| 9,655,729 B2 | 5/2017 | Parisi et al. |
| 9,707,089 B2 | 7/2017 | Grey et al. |
| 9,763,794 B2 | 9/2017 | Sanford et al. |
| 9,763,795 B2 | 9/2017 | Parisi et al. |
| 9,763,796 B2 | 9/2017 | Wentorf et al. |
| 9,763,807 B2 | 9/2017 | Claypool et al. |
| 9,788,954 B2 | 10/2017 | Parisi et al. |
| 9,861,490 B2 | 1/2018 | Wentorf et al. |
| 9,901,331 B2 | 2/2018 | Toler et al. |
| 9,918,844 B2 | 3/2018 | Sanford et al. |
| 9,925,050 B2 | 3/2018 | Parisi et al. |
| 9,925,052 B2 | 3/2018 | Dai et al. |
| 10,010,330 B2 | 7/2018 | Claypool et al. |
| 10,092,407 B2 | 10/2018 | Faccioli et al. |
| 10,188,530 B2 | 1/2019 | Claypool et al. |
| 10,195,041 B2 | 2/2019 | Wentorf et al. |
| 10,265,181 B2 | 4/2019 | Wentorf et al. |
| 10,278,827 B2 | 5/2019 | Drury et al. |
| 10,413,415 B2 | 9/2019 | Parisi et al. |
| 10,470,889 B2 | 11/2019 | Wentorf et al. |
| 10,500,054 B2 | 12/2019 | Croll |
| 10,517,735 B2 | 12/2019 | Lloyd et al. |
| 10,543,099 B2 | 1/2020 | Sanford et al. |
| 10,575,956 B2 | 3/2020 | Dai et al. |
| 10,675,153 B2 | 6/2020 | Byrd et al. |
| 10,835,380 B2 | 11/2020 | Drury et al. |
| 10,898,337 B2 | 1/2021 | Parisi et al. |
| 11,051,948 B2 | 7/2021 | Arnold et al. |
| 11,160,659 B2 | 11/2021 | Drury et al. |
| 11,207,198 B2 | 12/2021 | Oh et al. |
| 11,224,519 B2 | 1/2022 | Wentorf et al. |
| 11,324,598 B2 | 5/2022 | Dai et al. |
| 11,324,599 B2 | 5/2022 | Croll |
| 11,426,282 B2 | 8/2022 | Yager |
| 11,471,288 B2 | 10/2022 | Parisi et al. |
| 11,547,571 B2 | 1/2023 | Byrd et al. |
| 2001/0047210 A1 | 11/2001 | Wolf |
| 2002/0058997 A1 | 5/2002 | O'connor et al. |
| 2002/0072802 A1 | 6/2002 | O'Neil et al. |
| 2002/0103541 A1 | 8/2002 | Meyers et al. |
| 2002/0120340 A1 | 8/2002 | Metzger et al. |
| 2002/0161448 A1 | 10/2002 | Hayes, Jr. et al. |
| 2003/0055509 A1 | 3/2003 | Mccue et al. |
| 2003/0199985 A1 | 10/2003 | Masini |
| 2004/0019382 A1 | 1/2004 | Amirouche et al. |
| 2004/0019383 A1 | 1/2004 | Beguec |
| 2004/0034432 A1 | 2/2004 | Hughes et al. |
| 2004/0059340 A1 | 3/2004 | Serra et al. |
| 2004/0064191 A1 | 4/2004 | Wasielewski |
| 2004/0122441 A1 | 6/2004 | Muratsu |
| 2004/0153066 A1 | 8/2004 | Coon et al. |
| 2004/0162620 A1 | 8/2004 | Wyss |
| 2004/0167537 A1 | 8/2004 | Errico et al. |
| 2004/0186582 A1 | 9/2004 | Yasuda et al. |
| 2004/0204765 A1 | 10/2004 | Fenning et al. |
| 2004/0225368 A1 | 11/2004 | Plumet et al. |
| 2004/0236429 A1 | 11/2004 | Ensign et al. |
| 2004/0243244 A1 | 12/2004 | Otto et al. |

(56) References Cited

U.S. PATENT DOCUMENTS

| | | |
|---|---|---|
| 2004/0267371 A1 | 12/2004 | Hayes, Jr. et al. |
| 2005/0055102 A1 | 3/2005 | Tornier et al. |
| 2005/0096747 A1 | 5/2005 | Tuttle et al. |
| 2005/0143831 A1 | 6/2005 | Justin et al. |
| 2005/0143832 A1 | 6/2005 | Carson |
| 2005/0177170 A1 | 8/2005 | Fisher et al. |
| 2005/0197710 A1 | 9/2005 | Naegerl |
| 2005/0209701 A1 | 9/2005 | Suguro et al. |
| 2005/0209702 A1 | 9/2005 | Todd et al. |
| 2005/0246030 A1 | 11/2005 | Yao |
| 2005/0267485 A1 | 12/2005 | Cordes et al. |
| 2005/0267584 A1 | 12/2005 | Burdulis, Jr. et al. |
| 2005/0278035 A1 | 12/2005 | Wyss et al. |
| 2006/0004460 A1 | 1/2006 | Engh et al. |
| 2006/0020343 A1 | 1/2006 | Ek |
| 2006/0030945 A1 | 2/2006 | Wright |
| 2006/0052782 A1 | 3/2006 | Morgan et al. |
| 2006/0069436 A1 | 3/2006 | Sutton et al. |
| 2006/0089653 A1 | 4/2006 | Auger et al. |
| 2006/0111726 A1 | 5/2006 | Felt et al. |
| 2006/0142869 A1 | 6/2006 | Gross |
| 2006/0161259 A1 | 7/2006 | Cheng et al. |
| 2006/0184176 A1 | 8/2006 | Straszheim-Morley et al. |
| 2006/0189864 A1 | 8/2006 | Paradis et al. |
| 2006/0190087 A1 | 8/2006 | O'Connor |
| 2006/0195195 A1 | 8/2006 | Burstein et al. |
| 2006/0224244 A1 | 10/2006 | Thomas et al. |
| 2006/0265080 A1 | 11/2006 | Mcminn |
| 2007/0010890 A1 | 1/2007 | Collazo |
| 2007/0123992 A1 | 5/2007 | Sanford |
| 2007/0129808 A1 | 6/2007 | Justin et al. |
| 2007/0135924 A1 | 6/2007 | Verhoogen |
| 2007/0135926 A1 | 6/2007 | Walker |
| 2007/0185581 A1 | 8/2007 | Akizuki et al. |
| 2007/0198022 A1 | 8/2007 | Lang et al. |
| 2007/0233269 A1 | 10/2007 | Steines et al. |
| 2007/0234819 A1 | 10/2007 | Amirouche et al. |
| 2007/0239165 A1 | 10/2007 | Amirouche |
| 2008/0021566 A1 | 1/2008 | Peters et al. |
| 2008/0051908 A1 | 2/2008 | Angibaud et al. |
| 2008/0058947 A1 | 3/2008 | Earl et al. |
| 2008/0058948 A1 | 3/2008 | Biegun et al. |
| 2008/0091271 A1 | 4/2008 | Bonitati et al. |
| 2008/0091272 A1 | 4/2008 | Aram et al. |
| 2008/0091273 A1 | 4/2008 | Hazebrouck |
| 2008/0103603 A1 | 5/2008 | Hintermann |
| 2008/0114462 A1 | 5/2008 | Guidera et al. |
| 2008/0119938 A1 | 5/2008 | Oh |
| 2008/0119940 A1 | 5/2008 | Otto et al. |
| 2008/0140212 A1 | 6/2008 | Metzger et al. |
| 2008/0161918 A1 | 7/2008 | Fankhauser et al. |
| 2008/0167722 A1 | 7/2008 | Metzger et al. |
| 2008/0215156 A1 | 9/2008 | Duggal et al. |
| 2008/0243258 A1 | 10/2008 | Sancheti |
| 2008/0262624 A1 | 10/2008 | White et al. |
| 2008/0281426 A1 | 11/2008 | Fitz et al. |
| 2008/0288080 A1 | 11/2008 | Sancheti |
| 2008/0300689 A1 | 12/2008 | McKinnon et al. |
| 2008/0300690 A1 | 12/2008 | Burstein et al. |
| 2009/0005708 A1 | 1/2009 | Johanson et al. |
| 2009/0036992 A1 | 2/2009 | Tsakonas |
| 2009/0043395 A1 | 2/2009 | Hotokebuchi et al. |
| 2009/0062806 A1 | 3/2009 | Scott et al. |
| 2009/0082873 A1 | 3/2009 | Hazebrouck et al. |
| 2009/0088862 A1 | 4/2009 | Thomas et al. |
| 2009/0125114 A1 | 5/2009 | May et al. |
| 2009/0149963 A1 | 6/2009 | Sekel |
| 2009/0149964 A1 | 6/2009 | May et al. |
| 2009/0204221 A1 | 8/2009 | Walker |
| 2009/0204222 A1 | 8/2009 | Burstein et al. |
| 2009/0210066 A1 | 8/2009 | Jasty |
| 2009/0222103 A1 | 9/2009 | Fitz et al. |
| 2009/0259314 A1 | 10/2009 | Linder-ganz et al. |
| 2009/0264894 A1 | 10/2009 | Wasielewski |
| 2009/0265011 A1 | 10/2009 | Mandell |
| 2009/0265013 A1 | 10/2009 | Mandell |
| 2009/0287310 A1 | 11/2009 | Fisher et al. |
| 2009/0306786 A1 | 12/2009 | Samuelson |
| 2009/0306787 A1 | 12/2009 | Crabtree et al. |
| 2009/0319047 A1 | 12/2009 | Walker |
| 2009/0319048 A1 | 12/2009 | Shah et al. |
| 2009/0319049 A1 | 12/2009 | Shah et al. |
| 2009/0326663 A1 | 12/2009 | Dun |
| 2009/0326665 A1 | 12/2009 | Wyss et al. |
| 2009/0326666 A1 | 12/2009 | Wyss et al. |
| 2009/0326668 A1 | 12/2009 | Dun |
| 2010/0010494 A1 | 1/2010 | Quirno |
| 2010/0016976 A1 | 1/2010 | Siebel |
| 2010/0016977 A1 | 1/2010 | Masini |
| 2010/0016978 A1 | 1/2010 | Williams et al. |
| 2010/0016979 A1 | 1/2010 | Wyss et al. |
| 2010/0036499 A1 | 2/2010 | Pinskerova |
| 2010/0036500 A1 | 2/2010 | Heldreth et al. |
| 2010/0063594 A1 | 3/2010 | Hazebrouck et al. |
| 2010/0063595 A1 | 3/2010 | Dietz |
| 2010/0076563 A1 | 3/2010 | Otto et al. |
| 2010/0082111 A1 | 4/2010 | Thomas |
| 2010/0100011 A1 | 4/2010 | Roche |
| 2010/0100189 A1 | 4/2010 | Metzger |
| 2010/0100191 A1 | 4/2010 | May et al. |
| 2010/0125339 A1 | 5/2010 | Earl et al. |
| 2010/0152858 A1 | 6/2010 | Lu et al. |
| 2010/0191298 A1 | 7/2010 | Earl et al. |
| 2010/0191341 A1 | 7/2010 | Byrd |
| 2010/0198275 A1 | 8/2010 | Chana et al. |
| 2010/0222890 A1 | 9/2010 | Barnett et al. |
| 2010/0249660 A1 | 9/2010 | Sherman et al. |
| 2010/0249789 A1 | 9/2010 | Rock et al. |
| 2010/0262253 A1 | 10/2010 | Cipolletti et al. |
| 2010/0286788 A1 | 11/2010 | Komistek |
| 2010/0292804 A1 | 11/2010 | Samuelson |
| 2010/0305708 A1 | 12/2010 | Lang |
| 2010/0329530 A1 | 12/2010 | Lang et al. |
| 2011/0022179 A1 | 1/2011 | Andriacchi et al. |
| 2011/0029091 A1 | 2/2011 | Bojarski et al. |
| 2011/0040387 A1 | 2/2011 | Ries et al. |
| 2011/0066246 A1 | 3/2011 | Ries et al. |
| 2011/0082558 A1 | 4/2011 | Kim et al. |
| 2011/0082559 A1 | 4/2011 | Hartdegen et al. |
| 2011/0087332 A1 | 4/2011 | Bojarski et al. |
| 2011/0098824 A1 | 4/2011 | Jukes et al. |
| 2011/0100011 A1 | 5/2011 | Staffend |
| 2011/0125278 A1 | 5/2011 | Bercovy et al. |
| 2011/0144760 A1 | 6/2011 | Wong et al. |
| 2011/0153026 A1 | 6/2011 | Heggendorn et al. |
| 2011/0190898 A1 | 8/2011 | Lenz et al. |
| 2011/0202139 A1 | 8/2011 | Metzger et al. |
| 2011/0251695 A1 | 10/2011 | Lenz et al. |
| 2012/0022658 A1 | 1/2012 | Wentorf |
| 2012/0022659 A1 | 1/2012 | Wentorf |
| 2012/0022660 A1 | 1/2012 | Wentorf |
| 2012/0035735 A1 | 2/2012 | Sanford et al. |
| 2012/0035737 A1 | 2/2012 | Sanford |
| 2012/0095563 A1 | 4/2012 | Sanford et al. |
| 2012/0101585 A1 | 4/2012 | Parisi et al. |
| 2012/0158152 A1 | 6/2012 | Claypool et al. |
| 2012/0179069 A1 | 7/2012 | Amirouche |
| 2012/0185054 A1 | 7/2012 | Maloney et al. |
| 2012/0185055 A1 | 7/2012 | Maloney et al. |
| 2012/0232429 A1 | 9/2012 | Fischer et al. |
| 2012/0290088 A1 | 11/2012 | Amirouche et al. |
| 2012/0296437 A1 | 11/2012 | Wyss et al. |
| 2012/0310246 A1 | 12/2012 | Belcher et al. |
| 2012/0310361 A1 | 12/2012 | Zubok et al. |
| 2012/0323335 A1 | 12/2012 | Parisi et al. |
| 2012/0323336 A1 | 12/2012 | Parisi et al. |
| 2013/0013076 A1 | 1/2013 | Fisher et al. |
| 2013/0024001 A1 | 1/2013 | Wentorf et al. |
| 2013/0079671 A1 | 3/2013 | Stein et al. |
| 2013/0096567 A1 | 4/2013 | Fisher et al. |
| 2013/0102929 A1 | 4/2013 | Haight et al. |
| 2013/0103038 A1 | 4/2013 | Fischer et al. |
| 2013/0131816 A1 | 5/2013 | Parisi et al. |
| 2013/0131817 A1 | 5/2013 | Parisi et al. |

(56) References Cited

U.S. PATENT DOCUMENTS

| | | |
|---|---|---|
| 2013/0131818 A1 | 5/2013 | Parisi et al. |
| 2013/0131819 A1 | 5/2013 | Parisi et al. |
| 2013/0131820 A1 | 5/2013 | Wentorf et al. |
| 2013/0173010 A1 | 7/2013 | Irwin |
| 2013/0226305 A1 | 8/2013 | Donno et al. |
| 2013/0253378 A1 | 9/2013 | Claypool et al. |
| 2013/0261504 A1 | 10/2013 | Claypool et al. |
| 2013/0261757 A1 | 10/2013 | Claypool et al. |
| 2013/0261758 A1 | 10/2013 | Claypool et al. |
| 2013/0345820 A1 | 12/2013 | Maloney et al. |
| 2014/0025175 A1 | 1/2014 | Wentorf et al. |
| 2014/0025176 A1 | 1/2014 | Wentorf et al. |
| 2014/0025177 A1 | 1/2014 | Wentorf et al. |
| 2014/0052268 A1 | 2/2014 | Sanford et al. |
| 2014/0052269 A1 | 2/2014 | Claypool et al. |
| 2014/0156015 A1 | 6/2014 | Parisi et al. |
| 2014/0163687 A1 | 6/2014 | Parisi et al. |
| 2014/0249641 A1 | 9/2014 | Wentorf et al. |
| 2014/0257505 A1 | 9/2014 | Parisi et al. |
| 2014/0257506 A1 | 9/2014 | Sanford et al. |
| 2014/0296859 A1 | 10/2014 | Claypool et al. |
| 2015/0005890 A1 | 1/2015 | Parisi et al. |
| 2015/0025644 A1 | 1/2015 | Heggendorn et al. |
| 2015/0066150 A1 | 3/2015 | Dai et al. |
| 2015/0088140 A1 | 3/2015 | Toler et al. |
| 2015/0190243 A1 | 7/2015 | Claypool et al. |
| 2015/0282936 A1 | 10/2015 | Parisi et al. |
| 2015/0320564 A1 | 11/2015 | Parisi et al. |
| 2015/0359642 A1 | 12/2015 | Claypool et al. |
| 2016/0030053 A1 | 2/2016 | Yager et al. |
| 2016/0038294 A1 | 2/2016 | Parisi et al. |
| 2016/0045322 A1 | 2/2016 | Parisi et al. |
| 2016/0135959 A1 | 5/2016 | Sanford et al. |
| 2016/0158019 A1 | 6/2016 | Grey et al. |
| 2016/0184107 A1 | 6/2016 | Parisi et al. |
| 2016/0287397 A1 | 10/2016 | Wentorf et al. |
| 2016/0324647 A1 | 11/2016 | Claypool et al. |
| 2017/0079801 A1 | 3/2017 | Drury et al. |
| 2017/0143324 A1 | 5/2017 | Toler et al. |
| 2017/0156736 A1 | 6/2017 | Claypool et al. |
| 2017/0231773 A1 | 8/2017 | Lu |
| 2017/0266011 A1 | 9/2017 | Wentorf et al. |
| 2017/0281354 A1 | 10/2017 | Soffiatti et al. |
| 2018/0000601 A1 | 1/2018 | Sanford et al. |
| 2018/0000602 A1 | 1/2018 | Wentorf et al. |
| 2018/0000612 A1 | 1/2018 | Claypool et al. |
| 2018/0021143 A1 | 1/2018 | Parisi et al. |
| 2018/0021144 A1 | 1/2018 | Parisi et al. |
| 2018/0085225 A1 | 3/2018 | Wentorf et al. |
| 2018/0161166 A1 | 6/2018 | Dai et al. |
| 2018/0256346 A1 | 9/2018 | Byrd et al. |
| 2018/0325684 A1 | 11/2018 | Croll |
| 2019/0142594 A1 | 5/2019 | Yager |
| 2019/0209333 A1 | 7/2019 | Drury et al. |
| 2019/0328535 A1 | 10/2019 | Drury et al. |
| 2019/0350718 A1 | 11/2019 | Parisi et al. |
| 2020/0030106 A1 | 1/2020 | Wentorf et al. |
| 2020/0060833 A1 | 2/2020 | Arnold et al. |
| 2020/0069433 A1 | 3/2020 | Croll |
| 2020/0113702 A1 | 4/2020 | Sanford et al. |
| 2020/0146830 A1 | 5/2020 | Dai et al. |
| 2020/0237518 A1 | 7/2020 | Byrd et al. |
| 2021/0113340 A1 | 4/2021 | Parisi et al. |
| 2022/0096243 A1 | 3/2022 | Wentorf et al. |
| 2022/0233321 A1 | 7/2022 | Croll |
| 2022/0241081 A1 | 8/2022 | Garino |
| 2022/0346962 A1 | 11/2022 | Yager |
| 2023/0113335 A1 | 4/2023 | Byrd et al. |

FOREIGN PATENT DOCUMENTS

| | | |
|---|---|---|
| CA | 2190029 A1 | 11/1995 |
| CA | 2856070 C | 7/2016 |
| CH | 687584 A5 | 1/1997 |
| CN | 1087506 A | 6/1994 |
| CN | 1174498 A | 2/1998 |
| CN | 1179709 A | 4/1998 |
| CN | 1440262 A | 9/2003 |
| CN | 1549695 A | 11/2004 |
| CN | 2768715 Y | 4/2006 |
| CN | 1780594 A | 5/2006 |
| CN | 1874738 A | 12/2006 |
| CN | 101214175 A | 7/2008 |
| CN | 101222886 A | 7/2008 |
| CN | 101288597 A | 10/2008 |
| CN | 101347359 A | 1/2009 |
| CN | 201175391 Y | 1/2009 |
| CN | 101361684 A | 2/2009 |
| CN | 101401750 A | 4/2009 |
| CN | 101426453 A | 5/2009 |
| CN | 101522136 A | 9/2009 |
| CN | 101646392 A | 2/2010 |
| CN | 101658446 A | 3/2010 |
| CN | 101683289 A | 3/2010 |
| CN | 101711701 A | 5/2010 |
| CN | 101795643 A | 8/2010 |
| CN | 101835441 A | 9/2010 |
| CN | 102018584 A | 4/2011 |
| CN | 102048594 A | 5/2011 |
| CN | 102058446 A | 5/2011 |
| CN | 102058448 A | 5/2011 |
| CN | 102917670 A | 2/2013 |
| CN | 103118634 A | 5/2013 |
| CN | 103118635 A | 5/2013 |
| CN | 103118636 A | 5/2013 |
| CN | 103370025 A | 10/2013 |
| CN | 103379880 A | 10/2013 |
| CN | 103732186 A | 4/2014 |
| CN | 104039273 A | 9/2014 |
| CN | 104066402 A | 9/2014 |
| CN | 104093380 A | 10/2014 |
| CN | 104135969 A | 11/2014 |
| CN | 104203160 A | 12/2014 |
| CN | 104321263 A | 1/2015 |
| CN | 104379094 A | 2/2015 |
| CN | 104736105 A | 6/2015 |
| CN | 105055052 A | 11/2015 |
| CN | 105167889 A | 12/2015 |
| CN | 103118634 B | 8/2016 |
| CN | 103118636 B | 8/2016 |
| CN | 104093380 B | 8/2016 |
| CN | 103370025 B | 11/2016 |
| CN | 106073949 A | 11/2016 |
| CN | 106214292 A | 12/2016 |
| CN | 108135701 A | 6/2018 |
| CN | 106073949 B | 12/2018 |
| CN | 109310504 A | 2/2019 |
| CN | 110022798 A | 7/2019 |
| CN | 110402123 A | 11/2019 |
| CN | 110636818 A | 12/2019 |
| CN | 113317912 A | 8/2021 |
| EP | 0021421 A1 | 1/1981 |
| EP | 0303467 A2 | 2/1989 |
| EP | 0327495 A2 | 8/1989 |
| EP | 0340919 A1 | 11/1989 |
| EP | 340919 A1 | 11/1989 |
| EP | 0372811 A1 | 6/1990 |
| EP | 0306744 B1 | 4/1992 |
| EP | 0495340 A1 | 7/1992 |
| EP | 0636353 A1 | 2/1995 |
| EP | 0672397 A1 | 9/1995 |
| EP | 0552950 B1 | 9/1996 |
| EP | 0536457 B1 | 1/1997 |
| EP | 0642328 B1 | 12/1998 |
| EP | 0592750 B1 | 1/1999 |
| EP | 0903125 A1 | 3/1999 |
| EP | 0956836 A1 | 11/1999 |
| EP | 0956836 B1 | 11/1999 |
| EP | 1025818 A2 | 8/2000 |
| EP | 1097679 A1 | 5/2001 |
| EP | 0709074 B1 | 12/2002 |
| EP | 1327424 A1 | 7/2003 |
| EP | 1378216 A2 | 1/2004 |
| EP | 1477143 A1 | 11/2004 |

(56) References Cited

FOREIGN PATENT DOCUMENTS

| | | |
|---|---|---|
| EP | 1568336 A1 | 8/2005 |
| EP | 1719478 A2 | 11/2006 |
| EP | 1722721 A1 | 11/2006 |
| EP | 1354571 B1 | 6/2007 |
| EP | 1396240 B1 | 4/2008 |
| EP | 1604623 B1 | 6/2008 |
| EP | 1996122 A1 | 12/2008 |
| EP | 0927009 B1 | 1/2009 |
| EP | 2011455 A1 | 1/2009 |
| EP | 1696835 B1 | 2/2009 |
| EP | 1132063 A2 | 9/2009 |
| EP | 1591082 B1 | 9/2009 |
| EP | 2140838 A2 | 1/2010 |
| EP | 2140839 A1 | 1/2010 |
| EP | 2143403 A1 | 1/2010 |
| EP | 2237177 A1 | 10/2010 |
| EP | 1555962 B1 | 2/2011 |
| EP | 2319460 A1 | 5/2011 |
| EP | 2324799 A2 | 5/2011 |
| EP | 2335654 A1 | 6/2011 |
| EP | 2347733 A1 | 7/2011 |
| EP | 0689808 B1 | 9/2012 |
| EP | 2595573 A1 | 5/2013 |
| EP | 2782525 A1 | 10/2014 |
| EP | 2830543 A1 | 2/2015 |
| EP | 2830544 A1 | 2/2015 |
| EP | 2830544 B1 | 9/2016 |
| EP | 2918235 B1 | 1/2017 |
| EP | 3143964 A2 | 3/2017 |
| EP | 2595574 B1 | 5/2017 |
| EP | 3111894 B1 | 12/2018 |
| FR | 2728782 A1 | 7/1996 |
| FR | 2736819 A1 | 1/1997 |
| FR | 2747914 A1 | 10/1997 |
| FR | 2778332 A1 | 11/1999 |
| FR | 2788964 A1 | 8/2000 |
| FR | 2824260 A1 | 11/2002 |
| FR | 2852819 A1 | 10/2004 |
| FR | 2926719 A1 | 7/2009 |
| GB | 225347 A | 12/1924 |
| GB | 2253147 A | 9/1992 |
| GB | 2345446 A | 7/2000 |
| IN | 7145DELNP2014 A | 4/2015 |
| JP | 61247449 A | 11/1986 |
| JP | 62270153 A | 11/1987 |
| JP | 06203576 A | 7/1994 |
| JP | 09289998 A | 11/1997 |
| JP | 09511668 A | 11/1997 |
| JP | 2000000255 A | 1/2000 |
| JP | 2000245758 A | 9/2000 |
| JP | 2003516183 A | 5/2003 |
| JP | 2004166802 A | 6/2004 |
| JP | 2004254811 A | 9/2004 |
| JP | 3734270 B2 | 1/2006 |
| JP | 2007054488 A | 3/2007 |
| JP | 2007509709 A | 4/2007 |
| JP | 2007222616 A | 9/2007 |
| JP | 2009082713 A | 4/2009 |
| JP | 2009245619 A | 10/2009 |
| JP | 2010022827 A | 2/2010 |
| JP | 2010188051 A | 9/2010 |
| JP | 2010240406 A | 10/2010 |
| JP | 2010259808 A | 11/2010 |
| JP | 2011092738 A | 5/2011 |
| JP | 2012500667 A | 1/2012 |
| JP | 2012531265 A | 12/2012 |
| JP | 2015512307 A | 4/2013 |
| JP | 2013535276 A | 9/2013 |
| JP | 2013536005 A | 9/2013 |
| JP | 2013536006 A | 9/2013 |
| JP | 2013536007 A | 9/2013 |
| JP | 2014505517 A | 3/2014 |
| JP | 2014508554 A | 4/2014 |
| JP | 2014522292 A | 9/2014 |
| JP | 2014239900 A | 12/2014 |
| JP | 2015502203 A | 1/2015 |
| JP | 2015504333 A | 2/2015 |
| JP | 2015504759 A | 2/2015 |
| JP | 2015513966 A | 5/2015 |
| JP | 2015231566 A | 12/2015 |
| JP | 2016028729 A | 3/2016 |
| JP | 5980341 B2 | 8/2016 |
| JP | 2016195841 A | 11/2016 |
| JP | 2017221732 A | 12/2017 |
| JP | 2021142355 A | 9/2021 |
| WO | WO-9305729 A2 | 4/1993 |
| WO | WO-9409725 A1 | 5/1994 |
| WO | WO-9514444 A1 | 6/1995 |
| WO | WO-9514446 A1 | 6/1995 |
| WO | WO-9530389 A1 | 11/1995 |
| WO | WO-9535074 A1 | 12/1995 |
| WO | WO-9934755 A1 | 7/1999 |
| WO | WO-0141680 A1 | 6/2001 |
| WO | WO-200141680 A1 | 6/2001 |
| WO | WO-03099106 A2 | 12/2003 |
| WO | WO-2004058108 A1 | 7/2004 |
| WO | WO-2005037147 A1 | 4/2005 |
| WO | WO-2005051240 A1 | 6/2005 |
| WO | WO-2005122967 A1 | 12/2005 |
| WO | WO-2006058057 A2 | 6/2006 |
| WO | WO-2006092167 A1 | 9/2006 |
| WO | WO-2007108804 A1 | 9/2007 |
| WO | WO-2007109641 A2 | 9/2007 |
| WO | WO-2007119173 A2 | 10/2007 |
| WO | WO-2009029631 A1 | 3/2009 |
| WO | WO-2009088235 A2 | 7/2009 |
| WO | WO-2009088236 A2 | 7/2009 |
| WO | WO-2009088238 A2 | 7/2009 |
| WO | WO-2009105495 A1 | 8/2009 |
| WO | WO 2010001010 A1 | 1/2010 |
| WO | WO-2010008803 A2 | 1/2010 |
| WO | WO-2010011590 A1 | 1/2010 |
| WO | WO-2010022272 A1 | 2/2010 |
| WO | WO-2010023062 A1 | 3/2010 |
| WO | WO-2010045537 A1 | 4/2010 |
| WO | WO-2010075365 A2 | 7/2010 |
| WO | WO-2011043955 A1 | 4/2011 |
| WO | WO-2011063123 A2 | 5/2011 |
| WO | WO-2011071979 A1 | 6/2011 |
| WO | WO-2011072235 A2 | 6/2011 |
| WO | WO-2011110865 A2 | 9/2011 |
| WO | WO-2012004580 A1 | 1/2012 |
| WO | WO-2012018563 A1 | 2/2012 |
| WO | WO-2012018564 A1 | 2/2012 |
| WO | WO-2012018565 A1 | 2/2012 |
| WO | WO-2012018566 A1 | 2/2012 |
| WO | WO-2012018567 A1 | 2/2012 |
| WO | WO-2012020460 A1 | 2/2012 |
| WO | WO-2012082628 A1 | 6/2012 |
| WO | WO-2012083280 A1 | 6/2012 |
| WO | WO-2012112698 A2 | 8/2012 |
| WO | WO-2012173706 A1 | 12/2012 |
| WO | WO-2013003433 A1 | 1/2013 |
| WO | WO-2013013094 A1 | 1/2013 |
| WO | WO-2013074142 A1 | 5/2013 |
| WO | WO-2013074143 A1 | 5/2013 |
| WO | WO-2013074144 A1 | 5/2013 |
| WO | WO-2013074145 A1 | 5/2013 |
| WO | WO-2013077919 A1 | 5/2013 |
| WO | WO-2013115849 A1 | 8/2013 |
| WO | WO-2013148954 A1 | 10/2013 |
| WO | WO-2013148960 A1 | 10/2013 |
| WO | WO-2017053196 A1 | 3/2017 |
| WO | WO-2018165442 A1 | 9/2018 |
| WO | WO-2018208612 A1 | 11/2018 |

OTHER PUBLICATIONS

"U.S. Appl. No. 16/179,201, Supplemental Notice of Allowability dated Aug. 2, 2022", 2 pgs.

"U.S. Appl. No. 16/530,423, Notice of Allowance dated Jun. 14, 2022", 6 pgs.

(56) References Cited

OTHER PUBLICATIONS

"U.S. Appl. No. 16/530,423, Response filed Jun. 1, 2022 to Non Final Office Action dated Mar. 3, 2022", 14 pgs.
"U.S. Appl. No. 16/849,394, Examiner Interview Summary dated Aug. 29, 2022", 2 pgs.
"U.S. Appl. No. 16/849,394, Non Final Office Action dated Jun. 3, 2022", 9 pgs.
"U.S. Appl. No. 16/849,394, Notice of Allowance dated Sep. 15, 2022", 8 pgs.
"U.S. Appl. No. 16/849,394, Response filed Aug. 24, 2022 to Non Final Office Action dated Jun. 3, 2022", 15 pgs.
"U.S. Appl. No. 17/717,898, Preliminary Amendment filed Apr. 29, 2022", 7 pgs.
"U.S. Appl. No. 17/866,151, Preliminary Amendment filed Aug. 3, 2022", 6 pgs.
"European Application Serial No. 21177256.1, Extended European Search Report dated May 17, 2022", 9 pgs.
"Japanese Application Serial No. 2021-097369, Notification of Reasons for Rejection dated Jun. 14, 2022", w/ English Translation, 11 pgs.
"U.S. Appl. No. 15/720,866, PTO Response to Rule 312 Communication dated Nov. 20, 2020", 2 pgs.
"U.S. Appl. No. 16/179,201, Advisory Action dated Jun. 25, 2021", 3 pgs.
"U.S. Appl. No. 16/179,201, Examiner Interview Summary dated Feb. 8, 2021", 3 pgs.
"U.S. Appl. No. 16/179,201, Examiner Interview Summary dated Nov. 9, 2021", 4 pgs.
"U.S. Appl. No. 16/179,201, Examiner Interview Summary dated Nov. 17, 2021", 3 pgs.
"U.S. Appl. No. 16/179,201, Final Office Action dated Apr. 20, 2021", 11 pgs.
"U.S. Appl. No. 16/179,201, Non Final Office Action dated Sep. 22, 2021", 11 pgs.
"U.S. Appl. No. 16/179,201, Notice of Allowance dated Apr. 21, 2022", 9 pgs.
"U.S. Appl. No. 16/179,201, Response filed Jan. 28, 2021 to Non Final Office Action dated Nov. 2, 2020", 16 pgs.
"U.S. Appl. No. 16/179,201, Response filed Jun. 18, 2021 to Final Office Action dated Apr. 20, 2021", 16 pgs.
"U.S. Appl. No. 16/179,201, Response filed Dec. 3, 2021 to Non Final Office Action dated Sep. 22, 2021", 11 pgs.
"U.S. Appl. No. 16/179,201, Supplemental Response filed Feb. 19, 2021 to Non-Final Office Action dated Nov. 2, 2020", 17 pgs.
"U.S. Appl. No. 16/352,287, Final Office Action dated May 25, 2021", 8 pgs.
"U.S. Appl. No. 16/352,287, Non Final Office Action dated Dec. 10, 2020", 12 pgs.
"U.S. Appl. No. 16/352,287, Notice of Allowance dated Jun. 30, 2021", 7 pgs.
"U.S. Appl. No. 16/352,287, Response filed Feb. 22, 2021 to Non Final Office Action dated Dec. 10, 2020", 14 pgs.
"U.S. Appl. No. 16/352,287, Response filed Jun. 18, 2021 to Final Office Action dated May 25, 2021", 8 pgs.
"U.S. Appl. No. 16/530,423, Final Office Action dated Nov. 4, 2021", 11 pgs.
"U.S. Appl. No. 16/530,423, Non Final Office Action dated Mar. 3, 2022", 14 pgs.
"U.S. Appl. No. 16/530,423, Non Final Office Action dated May 17, 2021", 10 pgs.
"U.S. Appl. No. 16/530,423, Response filed Feb. 4, 2022 to Final Office Action dated Nov. 4, 2021", 15 pgs.
"U.S. Appl. No. 16/530,423, Response filed Aug. 11, 2021 to Non Final Office Action dated May 17, 2021", 15 pgs.
"U.S. Appl. No. 16/596,194, Amendment Under 1.312 Filed Dec. 7, 2021", 9 pgs.
"U.S. Appl. No. 16/596,194, Final Office Action dated May 20, 2021", 21 pgs.
"U.S. Appl. No. 16/596,194, Non Final Office Action dated Jan. 22, 2021", 19 pgs.
"U.S. Appl. No. 16/596,194, Notice of Allowance dated Sep. 9, 2021", 10 pgs.
"U.S. Appl. No. 16/596,194, PTO Response to Rule 312 Communication dated Dec. 13, 2021", 2 pgs.
"U.S. Appl. No. 16/596,194, Response filed Apr. 12, 2021 to Non Final Office Action dated Jan. 22, 2021", 15 pgs.
"U.S. Appl. No. 16/596,194, Response filed Aug. 18, 2021 to Final Office Action dated May 20, 2021", 15 pgs.
"U.S. Appl. No. 16/675,938, Non Final Office Action dated Sep. 16, 2021", 5 pgs.
"U.S. Appl. No. 16/675,938, Notice of Allowance dated Jan. 12, 2022", 8 pgs.
"U.S. Appl. No. 16/675,938, Response filed Dec. 3, 2021 to Non Final Office Action dated Sep. 16, 2021", 8 pgs.
"U.S. Appl. No. 16/675,938, Supplemental Notice of Allowability dated Feb. 1, 2022", 2 pgs.
"U.S. Appl. No. 16/715,092, Final Office Action dated Mar. 16, 2022", 8 pgs.
"U.S. Appl. No. 16/715,092, Non Final Office Action dated Sep. 22, 2021", 8 pgs.
"U.S. Appl. No. 16/715,092, Response filed Aug. 9, 2021 to Restriction Requirement dated Jun. 25, 2021", 7 pgs.
"U.S. Appl. No. 16/715,092, Response filed Dec. 10, 2021 to Non Final Office Action dated Sep. 22, 2021", 14 pgs.
"U.S. Appl. No. 16/715,092, Restriction Requirement dated Jun. 25, 2021", 6 pgs.
"U.S. Appl. No. 16/743,746, Notice of Allowance dated Jan. 13, 2022", 14 pgs.
"U.S. Appl. No. 16/743,746, Supplemental Notice of Allowability dated Jan. 27, 2022", 2 pgs.
"U.S. Appl. No. 17/134,885, Preliminary Amendment filed Jan. 18, 2021", 10 pgs.
"U.S. Appl. No. 17/545,728, Preliminary Amendment filed Jan. 7, 2022", 10 pgs.
"Australian Application Serial No. 2020204019, First Examination Report dated Jun. 18, 2021", 7 pgs.
"Australian Application Serial No. 2020204019, Response filed Jan. 11, 2022 to Subsequent Examiners Report dated Nov. 16, 2021", 19 pgs.
"Australian Application Serial No. 2020204019, Response filed Aug. 19, 2021 to First Examination Report dated Jun. 18, 2021", 3 pgs.
"Australian Application Serial No. 2020204019, Response filed Oct. 15, 2021 to Subsequent Examiners Report dated Sep. 2, 2021", 22 pgs.
"Australian Application Serial No. 2020204019, Subsequent Examiners Report dated Sep. 2, 2021", 4 pgs.
"Australian Application Serial No. 2020204019, Subsequent Examiners Report dated Nov. 16, 2021", 3 pgs.
"Canadian Application Serial No. 3,063,415, Response filed Nov. 12, 2020 to Office Action dated Jul. 13, 2020", 15 pgs.
"Chinese Application Serial No. 201880016775.4, Decision of Rejection dated Jul. 12, 2021", (W/ English Translation), 13 pgs.
"Chinese Application Serial No. 201880016775.4, Office Action dated Jan. 22, 2021", with English translation, 15 pages.
"Chinese Application Serial No. 201880031319.7, Office Action dated Nov. 18, 2020", (W/ English Translation), 9 pgs.
"Chinese Application Serial No. 201880031319.7, Response filed Jan. 18, 2021 to Office Action dated Nov. 18, 2020", (W/ English Claims), 16 pgs.
"European Application Serial No. 16189084.3, Communication Pursuant to Article 94(3) EPC dated Jul. 1, 2021", 6 pgs.
"European Application Serial No. 16189084.3, Response filed Nov. 8, 2021 to Communication Pursuant to Article 94(3) EPC dated Jul. 1, 2021", 61 pgs.
"European Application Serial No. 20175535.2, Extended European Search Report dated Aug. 18, 2021", 16 pgs.
"European Application Serial No. 20175535.2, Partial European Search Report dated May 18, 2021", 18 pgs.
"European Application Serial No. 20175535.2, Response Filed Mar. 15, 2022 to Extended European Search Report dated Aug. 18, 2021", 31 pgs.

(56) References Cited

OTHER PUBLICATIONS

"European Application Serial No. 21178298.2, Extended European Search Report dated Mar. 1, 2022", 9 pgs.
"Japanese Application Serial No. 2019-562605, Notification of Reasons for Refusal dated Nov. 10, 2020", (W/ English Translation), 5 pgs.
"Japanese Application Serial No. 2019-562605, Response filed Feb. 9, 2021 to Notification of Reasons for Refusal dated Nov. 10, 2020", (W/ English Claims), 19 pgs.
"Mexican Application Serial No. 2016/001734, Response filed Aug. 31, 2021 to Office Action dated Jun. 7, 2021", (W/ English Translation of Claims), 29 pgs.
"U.S. Appl. No. 16/179,201, Non Final Office Action dated Nov. 2, 2020", 15 pgs.
"U.S. Appl. No. 16/352,287, Response filed Oct. 12, 2020 to Restriction Requirement dated Aug. 17, 2020", 8 pgs.
"Brazilian Application Serial No. BR1120130016736, Response filed Oct. 5, 2020 to Office Action dated Jun. 10, 2020", w/ English claims, 91 pgs.
U.S. Appl. No. 17/545,728, filed Dec. 8, 2021, Asymmetric Tibial Components for a Knee Prosthesis.
U.S. Appl. No. 15/045,799 U.S. Pat. No. 9,707,089, filed Feb. 17, 2016, Tibial Baseplate With Asymmetric Placement of Fixation Structures.
U.S. Appl. No. 17/134,885, filed Dec. 28, 2020, Tibial Bearing Component for a Knee Prosthesis With Improved Articular Characteristics.
U.S. Appl. No. 17/717,898, filed Apr. 11, 2022, Femoral Prostheses With Upsizing and Downsizing Capabilities.
"U.S. Appl. No. 13/087,610, Non Final Office Action dated Feb. 26, 2013", 7 pgs.
"U.S. Appl. No. 13/087,610, Notice of Allowance dated Jun. 28, 2013", 6 pgs.
"U.S. Appl. No. 13/087,610, Notice of Allowance dated Oct. 8, 2013", 7 pgs.
"U.S. Appl. No. 13/087,610, Response filed May 24, 2013 to Non Final Office Action dated Feb. 26, 2013", 15 pgs.
"U.S. Appl. No. 13/189,324, Examiner Interview Summary dated Jan. 13, 2014", 4 pgs.
"U.S. Appl. No. 13/189,324, Final Office Action dated Jul. 16, 2013", 19 pgs.
"U.S. Appl. No. 13/189,324, Non Final Office Action dated Dec. 11, 2012", 19 pgs.
"U.S. Appl. No. 13/189,324, Notice of Allowance dated Feb. 20, 2014", 8 pgs.
"U.S. Appl. No. 13/189,324, PTO Response to 312 Amendment dated May 29, 2014", 2 pgs.
"U.S. Appl. No. 13/189,324, Response filed Jan. 15, 2014 to Final Office Action dated Jul. 16, 2013", 23 pgs.
"U.S. Appl. No. 13/189,324, Response filed Jun. 10, 2013 to Non Final Office Action dated Dec. 11, 2012", 24 pgs.
"U.S. Appl. No. 13/189,328, Non Final Office Action dated Mar. 19, 2013", 10 pgs.
"U.S. Appl. No. 13/189,328, Notice of Allowance dated Oct. 8, 2013", 12 pgs.
"U.S. Appl. No. 13/189,328, PTO Response to 312 Amendment dated Dec. 13, 2013", 2 pgs.
"U.S. Appl. No. 13/189,328, Response filed Jan. 10, 2013 to Restriction Requirement dated Dec. 10, 2012", 9 pgs.
"U.S. Appl. No. 13/189,328, Response filed Jul. 18, 2013 to Non Final Office Action dated Mar. 19, 2013", 16 pgs.
"U.S. Appl. No. 13/189,328, Restriction Requirement dated Dec. 10, 2012", 6 pgs.
"U.S. Appl. No. 13/189,336, Notice of Allowance dated Sep. 13, 2013", 30 pgs.
"U.S. Appl. No. 13/189,336, PTO Response to 312 Amendment dated Nov. 25, 2013", 2 pgs.
"U.S. Appl. No. 13/189,336, Response filed Apr. 15, 2013 to Restriction Requirement dated Jan. 30, 2013", 21 pgs.
"U.S. Appl. No. 13/189,336, Response filed Jul. 17, 2013 to Restriction Requirement dated Jun. 17, 2013", 20 pgs.
"U.S. Appl. No. 13/189,336, Restriction Requirement dated Jan. 30, 2013", 5 pgs.
"U.S. Appl. No. 13/189,336, Restriction Requirement dated Jun. 17, 2013", 6 pgs.
"U.S. Appl. No. 13/189,338, Notice of Allowance dated Sep. 23, 2013", 23 pgs.
"U.S. Appl. No. 13/189,338, Response filed Apr. 15, 2013 to Restriction Requirement dated Feb. 14, 2013", 18 pgs.
"U.S. Appl. No. 13/189,338, Response filed Jul. 17, 2013 to Restriction Requirement dated Jun. 17, 2013", 16 pgs.
"U.S. Appl. No. 13/189,338, Restriction Requirement dated Feb. 14, 2013", 5 pgs.
"U.S. Appl. No. 13/189,338, Restriction Requirement dated Jun. 17, 2013", 6 pgs.
"U.S. Appl. No. 13/189,339, Notice of Allowance dated Sep. 20, 2013", 16 pgs.
"U.S. Appl. No. 13/189,339, Response filed Apr. 15, 2013 to Restriction Requirement dated Mar. 6, 2013", 11 pgs.
"U.S. Appl. No. 13/189,339, Response filed Jul. 17, 2013 to Restriction Requirement dated Jun. 17, 2013", 10 pgs.
"U.S. Appl. No. 13/189,339, Restriction Requirement dated Mar. 6, 2013", 6 pgs.
"U.S. Appl. No. 13/189,339, Restriction Requirement dated Jun. 17, 2013", 7 pgs.
"U.S. Appl. No. 13/229,103, Applicant Interview Summary dated Sep. 23, 2013", 2 pgs.
"U.S. Appl. No. 13/229,103, Examiner Interview Summary dated Sep. 13, 2013", 3 pgs.
"U.S. Appl. No. 13/229,103, Non Final Office Action dated Apr. 1, 2013", 18 pgs.
"U.S. Appl. No. 13/229,103, Notice of Allowance dated Sep. 18, 2013", 9 pgs.
"U.S. Appl. No. 13/229,103, Response filed Jul. 1, 2013 to Non Final Office Action dated Apr. 1, 2013", 19 pgs.
"U.S. Appl. No. 13/229,103, Supplemental Notice of Allowability dated Oct. 18, 2013", 2 pgs.
"U.S. Appl. No. 13/459,037, Final Office Action dated Sep. 23, 2013", 9 pgs.
"U.S. Appl. No. 13/459,037, Non Final Office Action dated Apr. 23, 2013", 10 pgs.
"U.S. Appl. No. 13/459,037, Notice of Allowance dated Jun. 13, 2014", 9 pgs.
"U.S. Appl. No. 13/459,037, Preliminary Amendment filed Apr. 27, 2012", 3 pgs.
"U.S. Appl. No. 13/459,037, Response filed Mar. 21, 2014 to Final Office Action dated Sep. 23, 2013", 15 pgs.
"U.S. Appl. No. 13/459,037, Response filed Mar. 28, 2013 to Restriction Requirement dated Feb. 26, 2013", 9 pgs.
"U.S. Appl. No. 13/459,037, Response filed Jul. 23, 2013 to Non Final Office Action dated Apr. 23, 2013", 19 pgs.
"U.S. Appl. No. 13/459,037, Restriction Requirement dated Feb. 26, 2013", 6 pgs.
"U.S. Appl. No. 13/459,041, Non Final Office Action dated Jan. 15, 2014", 16 pgs.
"U.S. Appl. No. 13/459,041, Non Final Office Action dated Sep. 9, 2014", 14 pgs.
"U.S. Appl. No. 13/459,041, Notice of Allowance dated Apr. 2, 2015", 10 pgs.
"U.S. Appl. No. 13/459,041, Preliminary Amendment filed Apr. 27, 2012", 7 pgs.
"U.S. Appl. No. 13/459,041, PTO Response to Rule 312 Communication dated Jun. 9, 2015", 2 pgs.
"U.S. Appl. No. 13/459,041, Response filed May 15, 2014 to Non-Final Office Action dated Jan. 15, 2014", 24 pgs.
"U.S. Appl. No. 13/459,041, Response filed Sep. 23, 2013 to Restriction Requirement dated Jul. 25, 2013", 18 pgs.
"U.S. Appl. No. 13/459,041, Response filed Dec. 9, 2014 to Non-Final Office Action dated Sep. 9, 2014", 23 pgs.
"U.S. Appl. No. 13/459,041, Restriction Requirement dated Jul. 25, 2013", 9 pgs.

(56) References Cited

OTHER PUBLICATIONS

"U.S. Appl. No. 13/459,048, Non Final Office Action dated Jul. 11, 2013", 6 pgs.
"U.S. Appl. No. 13/459,048, Notice of Allowance dated Nov. 26, 2013", 10 pgs.
"U.S. Appl. No. 13/459,048, Preliminary Amendment filed Apr. 27, 2012", 7 pgs.
"U.S. Appl. No. 13/459,048, Response filed Nov. 11, 2013 to Non-Final Office Action dated Jul. 11, 2013", 16 pgs.
"U.S. Appl. No. 13/459,056, Examiner Interview Summary dated Dec. 26, 2013", 3 pgs.
"U.S. Appl. No. 13/459,056, Non Final Office Action dated Jul. 25, 2013", 11 pgs.
"U.S. Appl. No. 13/459,056, Notice of Allowance dated Feb. 20, 2014", 5 pgs.
"U.S. Appl. No. 13/459,056, Preliminary Amendment filed Apr. 27, 2012", 7 pgs.
"U.S. Appl. No. 13/459,056, PTO Response to Rule 312 Communication dated May 22, 2014", 2 pgs.
"U.S. Appl. No. 13/459,056, Response filed Jan. 24, 2014 to Non-Final office Action dated Jul. 25, 2013", 27 pgs.
"U.S. Appl. No. 13/459,056, Response filed Apr. 8, 2013 to Restriction Requirement dated Mar. 6, 2013", 15 pgs.
"U.S. Appl. No. 13/459,056, Restriction Requirement dated Mar. 6, 2013", 6 pgs.
"U.S. Appl. No. 13/593,339, Non Final Office Action dated Oct. 4, 2013", 7 pgs.
"U.S. Appl. No. 13/593,339, Notice of Allowance dated Feb. 14, 2014", 9 pgs.
"U.S. Appl. No. 13/593,339, Preliminary Amendment filed Aug. 23, 2012", 6 pgs.
"U.S. Appl. No. 13/593,339, Response filed Jan. 31, 2014 to Non-Final Office Action dated Oct. 4, 2013", 19 pgs.
"U.S. Appl. No. 13/593,339, Response filed Aug. 30, 2013 to Restriction Requirement dated Aug. 1, 2013", 14 pgs.
"U.S. Appl. No. 13/593,339, Restriction Requirement dated Aug. 1, 2013", 5 pgs.
"U.S. Appl. No. 13/593,339, Supplemental Notice of Allowability dated Mar. 31, 2014", 2 pgs.
"U.S. Appl. No. 13/594,543, Corrected Notice of Allowance dated Mar. 16, 2016", 2 pgs.
"U.S. Appl. No. 13/594,543, Examiner Interview Summary dated Jan. 22, 2016", 3 pgs.
"U.S. Appl. No. 13/594,543, Final Office Action dated Jul. 17, 2014", 12 pgs.
"U.S. Appl. No. 13/594,543, Final Office Action dated Nov. 20, 2015", 28 pgs.
"U.S. Appl. No. 13/594,543, Non Final Office Action dated Jun. 19, 2015", 30 pgs.
"U.S. Appl. No. 13/594,543, Non Final Office Action dated Dec. 26, 2013", 15 pgs.
"U.S. Appl. No. 13/594,543, Non-Final Office Action dated Jan. 9, 2015", 23 pgs.
"U.S. Appl. No. 13/594,543, Notice of Allowance dated Mar. 1, 2016", 9 pgs.
"U.S. Appl. No. 13/594,543, Preliminary Amendment filed Aug. 24, 2012", 4 pgs.
"U.S. Appl. No. 13/594,543, Response filed Feb. 8, 2016 to Final Office Action dated Nov. 20, 2015", 17 pgs.
"U.S. Appl. No. 13/594,543, Response filed Apr. 7, 2015 to Non-Final Office Action dated Jan. 9, 2015", 27 pgs.
"U.S. Appl. No. 13/594,543, Response filed May 7, 2014 to Non-Final office Action dated Dec. 26, 2013", 17 pgs.
"U.S. Appl. No. 13/594,543, Response filed Sep. 21, 2015 to Non-Final Office Action dated Jun. 19, 2015", 25 pgs.
"U.S. Appl. No. 13/594,543, Response filed Oct. 11, 2013 to Restriction Requirement dated Sep. 12, 2013", 8 pgs.
"U.S. Appl. No. 13/594,543, Response filed Dec. 17, 2014 to Final Office Action dated Jul. 17, 2014", 15 pgs.
"U.S. Appl. No. 13/594,543, Restriction Requirement dated Sep. 12, 2013", 5 pgs.
"U.S. Appl. No. 13/819,116, Advisory Action dated Jan. 5, 2016", 3 pgs.
"U.S. Appl. No. 13/819,116, Corrected Notice of Allowance dated Oct. 21, 2016", 2 pgs.
"U.S. Appl. No. 13/819,116, Examiner Interview Summary dated Apr. 18, 2016", 11 pgs.
"U.S. Appl. No. 13/819,116, Final Office Action dated Jul. 26, 2016", 6 pgs.
"U.S. Appl. No. 13/819,116, Final Office Action dated Oct. 21, 2015", 15 pgs.
"U.S. Appl. No. 13/819,116, Non Final Office Action dated Feb. 17, 2016", 15 pgs.
"U.S. Appl. No. 13/819,116, Non Final Office Action dated Jun. 2, 2015", 14 pgs.
"U.S. Appl. No. 13/819,116, Notice of Allowance dated Sep. 29, 2016", 5 pgs.
"U.S. Appl. No. 13/819,116, Preliminary Amendment filed Feb. 26, 2013", 8 pgs.
"U.S. Appl. No. 13/819,116, Response filed Mar. 27, 2015 to Restriction Requirement dated Feb. 12, 2015", 11 pgs.
"U.S. Appl. No. 13/819,116, Response filed Apr. 29, 2016 to Non Final Office Action dated Feb. 17, 2016", 17 pgs.
"U.S. Appl. No. 13/819,116, Response filed Jul. 16, 2015 to Non Final Office Action dated Jun. 2, 2015", 22 pgs.
"U.S. Appl. No. 13/819,116, Response filed Sep. 14, 2016 Final Office Action dated Jul. 26, 2016", 10 pgs.
"U.S. Appl. No. 13/819,116, Response filed Dec. 15, 2015 to Final Office Action dated Oct. 21, 2015", 16 pgs.
"U.S. Appl. No. 13/819,116, Restriction Requirement dated Feb. 12, 2015", 7 pgs.
"U.S. Appl. No. 13/836,586, Express Abandonment filed May 30, 2014", 1 pg.
"U.S. Appl. No. 13/836,665, Examiner Interview Summary dated Jul. 17, 2014", 4 pgs.
"U.S. Appl. No. 13/836,665, Final Office Action dated Jul. 25, 2014", 25 pgs.
"U.S. Appl. No. 13/836,665, Non Final Office Action dated Jan. 30, 2014", 21 pgs.
"U.S. Appl. No. 13/836,665, Notice of Allowance dated Jun. 9, 2015", 10 pgs.
"U.S. Appl. No. 13/836,665, Response filed Jan. 23, 2015 to Final Office Action dated Jul. 25, 2014", 25 pgs.
"U.S. Appl. No. 13/836,665, Response filed May 30, 2014 to Non-Final Office Action dated Jan. 30, 2014", 21 pgs.
"U.S. Appl. No. 13/837,294, Final Office Action dated Apr. 25, 2016", 7 pgs.
"U.S. Appl. No. 13/837,294, Final Office Action dated Jun. 2, 2016", 7 pgs.
"U.S. Appl. No. 13/837,294, Non Final Office Action dated Dec. 10, 2015", 8 pgs.
"U.S. Appl. No. 13/837,294, Notice of Allowance dated Aug. 25, 2016", 5 pgs.
"U.S. Appl. No. 13/837,294, Response filed Mar. 4, 2016 to Non Final Office Action dated Dec. 10, 2015", 16 pgs.
"U.S. Appl. No. 13/837,294, Response filed Aug. 3, 2016 to Final Office Action dated Jun. 2, 2016", 7 pgs.
"U.S. Appl. No. 13/837,294, Response filed Oct. 12, 2015 to Restriction Requirement dated Aug. 24, 2015", 9 pgs.
"U.S. Appl. No. 13/837,294, Restriction Requirement dated Aug. 24, 2015", 6 pgs.
"U.S. Appl. No. 13/837,774, Examiner Interview Summary dated Jul. 22, 2014", 4 pgs.
"U.S. Appl. No. 13/837,774, Final Office Action dated Mar. 17, 2016", 14 pgs.
"U.S. Appl. No. 13/837,774, Final Office Action dated Jul. 28, 2014", 17 pgs.
"U.S. Appl. No. 13/837,774, Non Final Office Action dated Feb. 10, 2014", 33 pgs.
"U.S. Appl. No. 13/837,774, Non Final Office Action dated Sep. 18, 2015", 16 pgs.

(56) References Cited

OTHER PUBLICATIONS

"U.S. Appl. No. 13/837,774, Response filed Jan. 28, 2015 to Final Office Action dated Jul. 28, 2014", 16 pgs.
"U.S. Appl. No. 13/837,774, Response filed Jun. 10, 2014 to Non-Final Office Action dated Feb. 20, 2014", 29 pgs.
"U.S. Appl. No. 13/837,774, Response filed Jul. 7, 2015 to Restriction Requirement dated May 20, 2015", 10 pgs.
"U.S. Appl. No. 13/837,774, Response filed Dec. 16, 2015 to Non Final Office Action dated Sep. 18, 2015", 17 pgs.
"U.S. Appl. No. 13/837,774, Restriction Requirement dated May 20, 2015", 6 pgs.
"U.S. Appl. No. 14/034,076, Appeal Brief Filed Apr. 18, 2016", 21 pgs.
"U.S. Appl. No. 14/034,076, Final Office Action dated Dec. 21, 2015", 11 pgs.
"U.S. Appl. No. 14/034,076, Non Final Office Action dated Jun. 24, 2015", 11 pgs.
"U.S. Appl. No. 14/034,076, Notice of Allowance dated Oct. 28, 2016", 7 pgs.
"U.S. Appl. No. 14/034,076, Response filed Nov. 16, 2015 to Non Final Office Action dated Jun. 24, 2015", 13 pgs.
"U.S. Appl. No. 14/034,937, Appeal Brief Filed Sep. 9, 2015", 41 pgs.
"U.S. Appl. No. 14/034,937, Appeal Decision mailed May 30, 2017", 34 pgs.
"U.S. Appl. No. 14/034,937, Final Office Action dated Jun. 5, 2015", 22 pgs.
"U.S. Appl. No. 14/034,937, Non Final Office Action dated Jan. 2, 2015", 21 pgs.
"U.S. Appl. No. 14/034,937, Notice of Allowance dated Aug. 30, 2017", 14 pgs.
"U.S. Appl. No. 14/034,937, Preliminary Amendment filed Sep. 24, 2013", 3 pgs.
"U.S. Appl. No. 14/034,937, PTO Response to Rule 312 Communication dated Oct. 10, 2017", 2 pgs.
"U.S. Appl. No. 14/034,937, Response filed Mar. 30, 2015 to Non-Final Office Action", 24 pgs.
"U.S. Appl. No. 14/034,937, Response filed Oct. 27, 2014 to Restriction Requirement dated Sep. 11, 2014", 12 pgs.
"U.S. Appl. No. 14/034,937, Restriction Requirement dated Sep. 11, 2014", 6 pgs.
"U.S. Appl. No. 14/034,937, Supplemental Preliminary Amendment filed Oct. 24, 2013", 11 pgs.
"U.S. Appl. No. 14/034,944, Non Final Office Action dated Mar. 3, 2015", 16 pgs.
"U.S. Appl. No. 14/034,944, Notice of Allowance dated Aug. 28, 2015", 7 pgs.
"U.S. Appl. No. 14/034,944, Preliminary Amendment filed Sep. 24, 2013", 3 pgs.
"U.S. Appl. No. 14/034,944, Response filed Jun. 23, 2015 to Non Final Office Action dated Mar. 3, 2015", 15 pgs.
"U.S. Appl. No. 14/034,944, Response filed Dec. 15, 2014 to Restriction Requirement dated Oct. 14, 2014", 12 pgs.
"U.S. Appl. No. 14/034,944, Restriction Requirement dated Oct. 14, 2014", 6 pgs.
"U.S. Appl. No. 14/034,944, Supplemental Preliminary Amendment filed Oct. 24, 2013", 11 pgs.
"U.S. Appl. No. 14/034,954, Advisory Action dated Aug. 25, 2015", 3 pgs.
"U.S. Appl. No. 14/034,954, Final Office Action dated Jun. 1, 2015", 26 pgs.
"U.S. Appl. No. 14/034,954, Non Final Office Action dated Dec. 19, 2014", 25 pgs.
"U.S. Appl. No. 14/034,954, Notice of Allowance dated Nov. 20, 2015", 11 pgs.
"U.S. Appl. No. 14/034,954, Preliminary Amendment filed Sep. 24, 2013", 3 pgs.
"U.S. Appl. No. 14/034,954, Response filed Mar. 17, 2015 to Non Final Office Action dated Dec. 19, 2014", 21 pgs.
"U.S. Appl. No. 14/034,954, Response filed Aug. 3, 2015 to Final Office Action dated Jun. 1, 2015", 19 pgs.
"U.S. Appl. No. 14/034,954, Response filed Aug. 31, 2015 to Advisory Action dated Aug. 25, 2015", 21 pgs.
"U.S. Appl. No. 14/034,954, Response filed Oct. 27, 2014 to Restriction Requirement dated Aug. 25, 2014", 11 pgs.
"U.S. Appl. No. 14/034,954, Restriction Requirement dated Aug. 25, 2014", 7 pgs.
"U.S. Appl. No. 14/034,954, Supplemental Preliminary Amendment filed Oct. 25, 2013", 8 pgs.
"U.S. Appl. No. 14/034,963, Final Office Action dated Apr. 13, 2015", 22 pgs.
"U.S. Appl. No. 14/034,963, Final Office Action dated Oct. 13, 2015", 11 pgs.
"U.S. Appl. No. 14/034,963, Non Final Office Action dated Jul. 1, 2015", 15 pgs.
"U.S. Appl. No. 14/034,963, Non Final Office Action dated Nov. 21, 2014", 19 pgs.
"U.S. Appl. No. 14/034,963, Notice of Allowance dated Dec. 18, 2015", 5 pgs.
"U.S. Appl. No. 14/034,963, Preliminary Amendment filed Sep. 24, 2013", 3 pgs.
"U.S. Appl. No. 14/034,963, Response filed Mar. 20, 2015 to Non-Final Office Action dated Nov. 21, 2014", 20 pgs.
"U.S. Appl. No. 14/034,963, Response filed Jun. 19, 2015 to Final Office Action dated Apr. 13, 2015", 17 pgs.
"U.S. Appl. No. 14/034,963, Response filed Sep. 30, 2015 to Non Final Office Action dated Jul. 1, 2015", 14 pgs.
"U.S. Appl. No. 14/034,963, Response filed Nov. 20, 2015 to Final Office Action dated Oct. 13, 2015", 12 pgs.
"U.S. Appl. No. 14/063,032, Non Final Office Action dated Jun. 20, 2014", 6 pgs.
"U.S. Appl. No. 14/063,032, Notice of Allowance dated Dec. 19, 2014", 6 pgs.
"U.S. Appl. No. 14/063,032, Preliminary Amendment filed Oct. 25, 2013", 3 pgs.
"U.S. Appl. No. 14/063,032, Response filed Oct. 20, 2014 to Non-Final Office Action dated Jun. 20, 2014", 9 pgs.
"U.S. Appl. No. 14/063,593, Advisory Action dated Aug. 19, 2016", 3 pgs.
"U.S. Appl. No. 14/063,593, Final Office Action dated Jun. 9, 2016", 10 pgs.
"U.S. Appl. No. 14/063,593, Non Final Office Action dated Jan. 25, 2016", 9 pgs.
"U.S. Appl. No. 14/063,593, Non Final Office Action dated Nov. 30, 2016", 12 pgs.
"U.S. Appl. No. 14/063,593, Notice of Allowance dated May 2, 2017", 5 pgs.
"U.S. Appl. No. 14/063,593, Notice of Allowance dated May 25, 2017", 5 pgs.
"U.S. Appl. No. 14/063,593, Preliminary Amendment filed Oct. 25, 2013", 3 pgs.
"U.S. Appl. No. 14/063,593, Response filed Jan. 4, 2016 to Restriction Requirement dated Nov. 6, 2015", 6 pgs.
"U.S. Appl. No. 14/063,593, Response filed Feb. 24, 2017 to Non Final Office Action dated Nov. 30, 2016", 17 pgs.
"U.S. Appl. No. 14/063,593, Response filed Apr. 20, 2016 to Non Final Office Action dated Jan. 25, 2016", 17 pgs.
"U.S. Appl. No. 14/063,593, Response filed Aug. 11, 2016 to Final Office Action dated Jun. 9, 2016", 10 pgs.
"U.S. Appl. No. 14/063,593, Restriction Requirement dated Nov. 6, 2015", 6 pgs.
"U.S. Appl. No. 14/181,033, Non Final Office Action dated May 1, 2015", 5 pgs.
"U.S. Appl. No. 14/181,033, Notice of Allowance dated Jul. 17, 2015", 10 pgs.
"U.S. Appl. No. 14/181,033, Response filed Jun. 22, 2015 to Non-Final Office Action dated May 1, 2015", 11 pgs.
"U.S. Appl. No. 14/278,805, Notice of Allowance dated Dec. 1, 2015", 8 pgs.
"U.S. Appl. No. 14/278,805, Supplemental Notice of Allowability dated Jan. 21, 2016", 2 pgs.

(56) References Cited

OTHER PUBLICATIONS

"U.S. Appl. No. 14/284,028, Non Final Office Action dated Jul. 7, 2015", 17 pgs.
"U.S. Appl. No. 14/284,028, Notice of Allowance dated Nov. 6, 2015", 5 pgs.
"U.S. Appl. No. 14/284,028, Response filed Oct. 6, 2015 to Non Final Office Action dated Jul. 7, 2015", 15 pgs.
"U.S. Appl. No. 14/284,028, Supplemental Notice of Allowability dated Feb. 26, 2016", 5 pgs.
"U.S. Appl. No. 14/284,028, Supplemental Preliminary Amendment filed Jul. 8, 2014", 13 pgs.
"U.S. Appl. No. 14/284,144, Final Office Action dated Aug. 7, 2015", 13 pgs.
"U.S. Appl. No. 14/284,144, Non Final Office Action dated Mar. 25, 2015", 26 pgs.
"U.S. Appl. No. 14/284,144, Notice of Allowance dated Oct. 29, 2015", 8 pgs.
"U.S. Appl. No. 14/284,144, Preliminary Amendment filed May 21, 2014", 3 pgs.
"U.S. Appl. No. 14/284,144, Response filed Oct. 9, 2015 to Final Office Action dated Aug. 7, 2015", 13 pgs.
"U.S. Appl. No. 14/284,144, Response filed Jun. 23, 2015 to Non Final Office Action dated Mar. 25, 2015", 22 pgs.
"U.S. Appl. No. 14/284,144, Supplemental Preliminary Amendment filed Jul. 3, 2014", 10 pgs.
"U.S. Appl. No. 14/304,009, Notice of Allowance dated Nov. 16, 2016", 7 pgs.
"U.S. Appl. No. 14/304,009, Preliminary Amendment Filed Jul. 31, 2014", 7 pgs.
"U.S. Appl. No. 14/471,440, Notice of Allowance dated Nov. 13, 2017", 9 pgs.
"U.S. Appl. No. 14/471,440, Response filed Aug. 16, 2017 to Restriction Requirement dated Jun. 30, 2017", 8 pgs.
"U.S. Appl. No. 14/471,440, Restriction Requirement dated Jun. 30, 2017", 6 pgs.
"U.S. Appl. No. 14/490,153, Final Office Action dated Apr. 15, 2015", 18 pgs.
"U.S. Appl. No. 14/490,153, Non Final Office Action dated Nov. 12, 2014", 9 pgs.
"U.S. Appl. No. 14/490,153, Notice of Allowance dated Aug. 14, 2015", 10 pgs.
"U.S. Appl. No. 14/490,153, Preliminary Amendment filed Sep. 18, 2014", 3 pgs.
"U.S. Appl. No. 14/490,153, Response filed Feb. 18, 2015 to Non-Final Office Action dated Nov. 12, 2014", 14 pgs.
"U.S. Appl. No. 14/490,153, Response filed Jul. 7, 2015 to Final Office Action dated Apr. 15, 2015", 14 pgs.
"U.S. Appl. No. 14/660,217, Corrected Notice of Allowance dated May 26, 2016", 3 pgs.
"U.S. Appl. No. 14/660,217, Non Final Office Action dated Dec. 17, 2015", 8 pgs.
"U.S. Appl. No. 14/660,217, Notice of Allowance dated Apr. 26, 2016", 5 pgs.
"U.S. Appl. No. 14/660,217, Preliminary Amendment filed Mar. 18, 2015", 9 pgs.
"U.S. Appl. No. 14/660,217, Response filed Mar. 23, 2016 to Non Final Office Action dated Dec. 17, 2015", 14 pgs.
"U.S. Appl. No. 14/740,690, Non Final Office Action dated Dec. 7, 2016", 19 pgs.
"U.S. Appl. No. 14/740,690, Notice of Allowability dated Aug. 29, 2017", 2 pgs.
"U.S. Appl. No. 14/740,690, Notice of Allowance dated Jun. 13, 2017", 9 pgs.
"U.S. Appl. No. 14/740,690, Response filed Mar. 3, 2017 to Non Final Office Action dated Dec. 7, 2016", 14 pgs.
"U.S. Appl. No. 14/791,952, Corrected Notice of Allowance dated Jul. 21, 2017", 2 pgs.
"U.S. Appl. No. 14/791,952, Final Office Action dated Mar. 31, 2017", 8 pgs.
"U.S. Appl. No. 14/791,952, Final Office Action dated Sep. 1, 2016", 17 pgs.
"U.S. Appl. No. 14/791,952, Non Final Office Action dated Apr. 21, 2016", 12 pgs.
"U.S. Appl. No. 14/791,952, Non Final Office Action dated Dec. 29, 2016", 12 pgs.
"U.S. Appl. No. 14/791,952, Notice of Allowance dated May 30, 2017", 7 pgs.
"U.S. Appl. No. 14/791,952, Preliminary Amendment filed Jul. 7, 2015", 7 pgs.
"U.S. Appl. No. 14/791,952, Response filed Mar. 20, 2017 to Non Final Office Action dated Dec. 29, 2016", 12 pgs.
"U.S. Appl. No. 14/791,952, Response filed May 17, 2017-to Final Office Action dated Mar. 31, 2017", 10 pgs.
"U.S. Appl. No. 14/791,952, Response filed Jul. 15, 2016 to Non Final Office Action dated Apr. 21, 2016", 18 pgs.
"U.S. Appl. No. 14/791,952, Response filed Nov. 21, 2016 to Final Office Action dated Sep. 1, 2016", 15 pgs.
"U.S. Appl. No. 14/833,385, Examiner Interview Summary dated Dec. 27, 2017", 3 pgs.
"U.S. Appl. No. 14/833,385, Final Office Action dated Nov. 13, 2017", 9 pgs.
"U.S. Appl. No. 14/833,385, Non Final Office Action dated Jun. 19, 2017", 10 pgs.
"U.S. Appl. No. 14/833,385, Preliminary Amendment filed Aug. 25, 2015", 6 pgs.
"U.S. Appl. No. 14/833,385, Response filed May 12, 2017 to Restriction Requirement dated Mar. 17, 2017", 8 pgs.
"U.S. Appl. No. 14/833,385, Response filed Sep. 18, 2017 to Non Final Office Action dated Jun. 19, 2017", 14 pgs.
"U.S. Appl. No. 14/833,385, Restriction Requirement dated Mar. 17, 2017", 6 pgs.
"U.S. Appl. No. 14/918,721, Final Office Action dated Oct. 20, 2016", 5 pgs.
"U.S. Appl. No. 14/918,721, Non Final Office Action dated Jun. 16, 2016", 6 pgs.
"U.S. Appl. No. 14/918,721, Notice of Allowance dated Feb. 1, 2017", 9 pgs.
"U.S. Appl. No. 14/918,721, Preliminary Amendment filed Oct. 23, 2015", 8 pgs.
"U.S. Appl. No. 14/918,721, PTO Response to Rule 312 Communication dated Mar. 17, 2017", 2 pgs.
"U.S. Appl. No. 14/918,721, Response filed Sep. 12, 2016 to Non Final Office Action dated Jun. 16, 2016", 12 pgs.
"U.S. Appl. No. 14/918,721, Response filed Dec. 13, 2016 to Final Office Action dated Oct. 20, 2016", 9 pgs.
"U.S. Appl. No. 14/926,281, Non Final Office Action dated Jun. 21, 2017", 17 pgs.
"U.S. Appl. No. 14/926,281, Notice of Allowance dated Nov. 16, 2017", 9 pgs.
"U.S. Appl. No. 14/926,281, Preliminary Amendment filed Oct. 30, 2015", 8 pgs.
"U.S. Appl. No. 14/926,281, Response filed Sep. 18, 2017 to Non Final Office Action dated Jun. 21, 2017", 11 pgs.
"U.S. Appl. No. 15/003,091, Preliminary Amendment filed Jan. 22, 2016", 12 pgs.
"U.S. Appl. No. 15/003,091, Non Final Office Action dated Jun. 20, 2017", 14 pgs.
"U.S. Appl. No. 15/003,091, Notice of Allowance dated Nov. 6, 2017", 8 pgs.
"U.S. Appl. No. 15/003,091, PTO Response to Rule 312 Communication dated Jan. 23, 2018", 2 pgs.
"U.S. Appl. No. 15/003,091, Response filed Sep. 20, 2017 to Non Final Office Action dated Jun. 20, 2017", 17 pgs.
"U.S. Appl. No. 15/045,799, Non Final Office Action dated Nov. 1, 2016", 8 pgs.
"U.S. Appl. No. 15/045,799, Notice of Allowance dated Mar. 10, 2017", 10 pgs.
"U.S. Appl. No. 15/045,799, Preliminary Amendment filed Feb. 18, 2016", 9 pgs.
"U.S. Appl. No. 15/045,799, PTO Response to Rule 312 Communication dated Apr, 18, 2017", 2 pgs.

(56) References Cited

OTHER PUBLICATIONS

"U.S. Appl. No. 15/045,799, Response filed Feb. 1, 2017 to Non Final Office Action dated Nov. 1, 2016", 15 pgs.
"U.S. Appl. No. 15/062,252, Preliminary Amendment filed Mar. 9, 2016", 8 pgs.
"U.S. Appl. No. 15/062,262, Non Final Office Action dated Jul. 22, 2016", 12 pgs.
"U.S. Appl. No. 15/062,262, Notice of Allowance dated Jan. 31, 2017", 5 pgs.
"U.S. Appl. No. 15/062,262, PTO Response to Rule 312 Communication dated Mar. 7, 2017", 2 pgs.
"U.S. Appl. No. 15/062,262, Response filed Oct. 24, 2016 to Non Final Office Action dated Jul. 22, 2016", 13 pgs.
"U.S. Appl. No. 15/177,734, Non Final Office Action dated Feb. 10, 2017", 21 pgs.
"U.S. Appl. No. 15/177,734, Notice of Allowance dated May 17, 2017", 7 pgs.
"U.S. Appl. No. 15/177,734, Preliminary Amendment filed Jun. 22, 2016", 8 pgs.
"U.S. Appl. No. 15/177,734, Response filed Apr. 19, 2017 to Non Final Office Action dated Feb. 10, 2017", 22 pgs.
"U.S. Appl. No. 15/211,812, Non Final Office Action dated Jan. 27, 2017", 5 pgs.
"U.S. Appl. No. 15/211,812, Notice of Allowance dated May 31, 2017", 5 pgs.
"U.S. Appl. No. 15/211,812, Preliminary Amendment filed Sep. 8, 2016", 8 pgs.
"U.S. Appl. No. 15/211,812, Response filed Apr. 19, 2017 to Non Final Office Action dated Jan. 27, 2017", 9 pgs.
"U.S. Appl. No. 15/267,793, Non Final Office Action dated Jun. 14, 2018", 12 pgs.
"U.S. Appl. No. 15/267,793, Notice of Allowability dated Jan. 17, 2019", 2 pgs.
"U.S. Appl. No. 15/267,793, Notice of Allowance dated Dec. 21, 2018", 5 pgs.
"U.S. Appl. No. 15/267,793, Response Filed Apr. 11, 2018 to Restriction Requirement dated Feb. 16, 2018", 8 pgs.
"U.S. Appl. No. 15/267,793, Response filed Aug. 22, 2018 Non Final Office Action dated Jun. 14, 2018", 16 pgs.
"U.S. Appl. No. 15/267,793, Restriction Requirement dated Feb. 16, 2018", 7 pgs.
"U.S. Appl. No. 15/424,328, Non Final Office Action dated Jun. 23, 2017", 5 pgs.
"U.S. Appl. No. 15/424,328, Notice of Allowance dated Oct. 16, 2017", 6 pgs.
"U.S. Appl. No. 15/424,328, Preliminary Amendment filed Feb. 28, 2017", 10 pgs.
"U.S. Appl. No. 15/424,328, Response filed Sep. 20, 2017 to Non Final Office Action dated Jun. 23, 2017", 9 pgs.
"U.S. Appl. No. 15/435,620, Final Office Action dated Dec. 15, 2017", 9 pgs.
"U.S. Appl. No. 15/435,620, Non Final Office Action dated Jul. 26, 2017", 10 pgs.
"U.S. Appl. No. 15/435,620, Notice of Allowance dated Mar. 13, 2018", 5 pgs.
"U.S. Appl. No. 15/435,620, Preliminary Amendment filed Mar. 20, 2017", 7 pgs.
"U.S. Appl. No. 15/435,620, Response filed Feb. 12, 2018 to Final Office Action dated Dec. 15, 2017", 9 pgs.
"U.S. Appl. No. 15/435,620, Response filed Oct. 25, 2017 to Non Final Office Action dated Jul. 26, 2017", 13 pgs.
"U.S. Appl. No. 15/616,561, Non Final Office Action dated Aug. 9, 2018", 8 pgs.
"U.S. Appl. No. 15/616,561, Notice of Allowability dated Feb. 12, 2019", 2 pgs.
"U.S. Appl. No. 15/616,561, Notice of Allowance dated Dec. 10, 2018", 7 pgs.
"U.S. Appl. No. 15/616,561, Preliminary Amendment filed Jun. 8, 2017", 7 pgs.
"U.S. Appl. No. 15/616,561, Response filed Nov. 8, 2018 to Non Final Office Action dated Aug. 9, 2018", 11 pgs.
"U.S. Appl. No. 15/703,678, Non Final Office Action dated Apr. 8, 2019", 11 pgs.
"U.S. Appl. No. 15/703,678, Notice of Allowance dated Sep. 17, 2019", 7 pgs.
"U.S. Appl. No. 15/703,678, Preliminary Amendment filed Sep. 28, 2017", 9 pgs.
"U.S. Appl. No. 15/703,678, Response Filed Jan. 3, 2019 to Restriction Requirement dated Nov. 5, 2018", 8 pgs.
"U.S. Appl. No. 15/703,678, Response filed Jul. 3, 2019 to Non-Final Office Action dated Apr. 8, 2019", 20 pgs.
"U.S. Appl. No. 15/703,678, Restriction Requirement dated Nov. 5, 2018", 6 pgs.
"U.S. Appl. No. 15/703,692, Corrected Notice of Allowability dated Jul. 8, 2019", 2 pgs.
"U.S. Appl. No. 15/703,692, Non Final Office Action dated Jan. 14, 2019", 11 pgs.
"U.S. Appl. No. 15/703,692, Notice of Allowance dated May 7, 2019", 5 pgs.
"U.S. Appl. No. 15/703,692, Preliminary Amendment filed Sep. 28, 2017", 9 pgs.
"U.S. Appl. No. 15/703,692, Response filed Apr. 4, 2019 to Non Final Office Action dated Jan. 14, 2019", 11 pgs.
"U.S. Appl. No. 15/703,698, Corrected Notice of Allowability dated Dec. 18, 2018", 2 pgs.
"U.S. Appl. No. 15/703,698, Non Final Office Action dated Apr. 6, 2018", 7 pgs.
"U.S. Appl. No. 15/703,698, Notice of Allowance dated Sep. 12, 2018", 5 pgs.
"U.S. Appl. No. 15/703,698, Preliminary Amendment filed Sep. 28, 2017", 8 pgs.
"U.S. Appl. No. 15/703,698, Response filed Jul. 6, 2018 to Non Final Office Action dated Apr. 6, 2018", 10 pgs.
"U.S. Appl. No. 15/703,713, Non Final Office Action dated Mar. 27, 2018", 29 pgs.
"U.S. Appl. No. 15/703,713, Notice of Allowance dated Sep. 25, 2018", 11 pgs.
"U.S. Appl. No. 15/703,713, Response Filed Jun. 15, 2018 to Non-Final Office Action dated Mar. 27, 2018", 16 pgs.
"U.S. Appl. No. 15/703,713, Preliminary Amendment filed Sep. 28, 2017", 7 pgs.
"U.S. Appl. No. 15/720,866, Final Office Action dated Feb. 28, 2020", 10 pgs.
"U.S. Appl. No. 15/720,866, Non Final Office Action dated Sep. 9, 2019", 12 pgs.
"U.S. Appl. No. 15/720,866, Notice of Allowance dated Sep. 23, 2020", 7 pgs.
"U.S. Appl. No. 15/720,866, Response filed Jan. 9, 2020 to Non Final Office Action dated Sep. 9, 2019", 11 pgs.
"U.S. Appl. No. 15/720,866, Response filed May 27, 2020 to Final Office Action dated Feb. 28, 2020", 13 pgs.
"U.S. Appl. No. 15/720,866, Response filed Jul. 10, 2019 to Restriction Requirement dated May 14, 2019", 10 pgs.
"U.S. Appl. No. 15/720,866, Response filed Nov. 13, 2017 to Non Final Office Action dated Sep. 14, 2017", 10 pgs.
"U.S. Appl. No. 15/720,866, Restriction Requirement dated May 14, 2019", 7 pgs.
"U.S. Appl. No. 15/720,866, Preliminary Amendment filed Nov. 13, 2017", 9 pgs.
"U.S. Appl. No. 15/827,654, Examiner Interview Summary dated Apr. 26, 2019", 4 pgs.
"U.S. Appl. No. 15/827,654, Final Office Action dated Feb. 19, 2019", 19 pgs.
"U.S. Appl. No. 15/827,654, Non Final Office Action dated Sep. 7, 2018", 21 pgs.
"U.S. Appl. No. 15/827,654, Notice of Allowance dated Jul. 8, 2019", 8 pgs.
"U.S. Appl. No. 15/827,654, Preliminary Amendment filed Dec. 22, 2017", 11 pgs.
"U.S. Appl. No. 15/827,654, Response Filed May 20, 2019 to Final Office Action dated Feb. 19, 2019", 17 pgs.

(56) References Cited

OTHER PUBLICATIONS

"U.S. Appl. No. 15/827,654, Response filed Jun. 6, 2018 to Restriction Requirement dated Apr. 6, 2018", 11 pgs.
"U.S. Appl. No. 15/827,654, Response filed to Non Final Office Action dated Sep. 7, 2018", 24 pgs.
"U.S. Appl. No. 15/827,654, Restriction Requirement dated Apr. 6, 2018", 6 pgs.
"U.S. Appl. No. 15/890,735, Notice of Allowance dated Oct. 29, 2019", 11 pgs.
"U.S. Appl. No. 15/915,886, Non Final Office Action dated Aug. 2, 2019", 9 pgs.
"U.S. Appl. No. 15/915,886, Notice of Allowance dated Jan. 16, 2020", 9 pgs.
"U.S. Appl. No. 15/915,886, PTO Response to Rule 312 Communication dated May 8, 2020", 2 pgs.
"U.S. Appl. No. 15/915,886, Response Filed Nov. 4, 2019 to Non-Final Office Action dated Aug. 2, 2019", 8 pgs.
"U.S. Appl. No. 15/971,743, Notice of Allowance dated Aug. 6, 2019", 8 pgs.
"U.S. Appl. No. 16/179,201, Response filed Oct. 5, 2020 to Restriction Requirement dated Aug. 7, 2020", 9 pgs.
"U.S. Appl. No. 16/179,201, Restriction Requirement dated Aug. 7, 2020", 10 pgs.
"U.S. Appl. No. 16/352,287, Restriction Requirement dated Aug. 17, 2020", 6 pgs.
"U.S. Appl. No. 16/389,381, Non Final Office Action dated Mar. 30, 2020", 9 pgs.
"U.S. Appl. No. 16/389,381, Notice of Allowance dated Jul. 16, 2020", 5 pgs.
"U.S. Appl. No. 16/389,381, Response filed Jun. 19, 2020 to Non Final Office Action dated Mar. 30, 2020", 9 pgs.
"U.S. Appl. No. 16/530,423, Preliminary Amendment filed Aug. 28, 2019", 7 pgs.
"U.S. Appl. No. 16/596,194, Preliminary Amendment Filed Nov. 14, 2019", 8 pgs.
"U.S. Appl. No. 16/675,938, Preliminary Amendment filed Jan. 22, 2020", 7 pgs.
"U.S. Appl. No. 16/715,092, Preliminary Amendment filed Mar. 19, 2020", 10 pgs.
"U.S. Appl. No. 16/743,746, Preliminary Amendment filed Mar. 19, 2020", 8 pgs.
"U.S. Appl. No. 16/849,394, Preliminary Amendment filed Jun. 3, 2020", 7 pgs.
"Australian Application Serial No. 2011286306, First Examiner Report dated Jun. 19, 2013", 4 pgs.
"Australian Application Serial No. 2011286306, Response filed Jun. 3, 2014 to First Examiner Report dated Jun. 19, 2013", 16 pgs.
"Australian Application Serial No. 2011286307, First Examiner Report dated Oct. 17, 2013", 2 pgs.
"Australian Application Serial No. 2011286307, Response filed May 21, 2014 to First Examiner Report dated Oct. 17, 2013", 16 pgs.
"Australian Application Serial No. 2011286308, First Examiner Report dated Jun. 21, 2013", 4 pgs.
"Australian Application Serial No. 2011286308, Response filed Jun. 6, 2014 First Examiner Report dated Jun. 21, 2013", 19 pgs.
"Australian Application Serial No. 2011286309, First Examiner Report dated Jun. 21, 2013", 3 pgs.
"Australian Application Serial No. 2011286309, Response filed Jun. 10, 2014 to First Examiner Report dated Jun. 21, 2013", 4 pgs.
"Australian Application Serial No. 2011343440, First Examiner Report dated Feb. 17, 2014", 3 pgs.
"Australian Application Serial No. 2011343440, Response filed Mar. 21, 2014 to Office Action dated Feb. 17, 2014", 1 pg.
"Australian Application Serial No. 2012271243, Office Action dated Apr. 1, 2015", 2 pgs.
"Australian Application Serial No. 2012271243, Response filed Apr. 8, 2015 to Office Action dated Apr. 1, 2015", 4 pgs.
"Australian Application Serial No. 2012271243, Response filed Apr. 15, 2015 to Office Action dated Apr. 13, 2015", 1 pg.
"Australian Application Serial No. 2012271243, Subsequent Examiners Report dated Apr. 13, 2015", 2 pgs.
"Australian Application Serial No. 2012341026, First Examiner Report dated Jul. 14, 2014", 2 pgs.
"Australian Application Serial No. 2012341026, Response filed Nov. 21, 2014 to First Examiner Report dated Jul. 14, 2014", 1 pg.
"Australian Application Serial No. 2012341026, Statement of Proposed Amendment filed Jun. 18, 2014", 25 pgs.
"Australian Application Serial No. 2012368262, First Examiner Report dated Nov. 2, 2016", 4 pgs.
"Australian Application Serial No. 2012368262, Response filed Jan. 17, 2017 to Office Action dated Nov. 2, 2016", 21 pgs.
"Australian Application Serial No. 2012368262, Response filed May 15, 2017 to Subsequent Examiners Report dated Mar. 16, 2017", 2 pgs.
"Australian Application Serial No. 2012368262, Subsequent Examiners Report dated Mar. 16, 2017", 3 pgs.
"Australian Application Serial No. 2013238046, First Examiner Report dated Nov. 26, 2015", pgs.
"Australian Application Serial No. 2013238046, Response filed Feb. 2, 2016 to First Examiner Report dated Nov. 26, 2015", 1 pg.
"Australian Application Serial No. 2013238054, First Examiner Report dated Oct. 17, 2016", 4 pgs.
"Australian Application Serial No. 2013238054, Response filed Jan. 18, 2017 to First Examiner Report dated Oct. 17, 2016", 9 pgs.
"Australian Application Serial No. 2014250709, First Examiner Report dated Dec. 21, 2015", 3 pgs.
"Australian Application Serial No. 2014250709, Response filed May 4, 2016 to First Examiner Report dated Dec. 21, 2015", 12 pgs.
"Australian Application Serial No. 2014250709, Subsequent Examiners Report dated May 31, 2016", 6 pgs.
"Australian Application Serial No. 2014250710, First Examiner Report dated Dec. 11, 2015", 7 pgs.
"Australian Application Serial No. 2014250710, Response filed Mar. 22, 2016 to First Examiner Report dated Dec. 11, 2015", 18 pgs.
"Australian Application Serial No. 2014250710, Response filed May 4, 2016 to Subsequent Examiners Report dated Mar. 23, 2016", 15 pgs.
"Australian Application Serial No. 2014250710, Subsequent Examiners Report dated Mar. 23, 2016", 3 pgs.
"Australian Application Serial No. 2014250711, First Examiner Report dated Feb. 12, 2016", 7 pgs.
"Australian Application Serial No. 2014250711, Response filed Apr. 27, 2016 to First Examiner Report dated Feb. 12, 2016", 32 pgs.
"Australian Application Serial No. 2015201511, First Examination Report dated Apr. 18, 2016", 2 pgs.
"Australian Application Serial No. 2015201511, Response filed Jun. 30, 2016 to First Examiner Report dated Apr. 18, 2016", 12 pgs.
"Australian Application Serial No. 2015238820, First Examination Report dated May 30, 2017", 13 pgs.
"Australian Application Serial No. 2015238820, Response filed Jul. 12, 2017 to First Examination Report dated May 30, 2017", 12 pgs.
"Australian Application Serial No. 2016225911, First Examiners Report dated Jun. 2, 2017", 3 pgs.
"Australian Application Serial No. 2016225911, Response filed Aug. 22, 2017 to First Examiners Report dated Jun. 2, 2017", 18 pgs.
"Australian Application Serial No. 2017235987, First Examination Report dated Nov. 1, 2018", 4 pgs.
"Australian Application Serial No. 2017251736, First Examiners Report dated Oct. 31, 2017", 2 pgs.
"Australian Application Serial No. 2018266322, First Examination Report dated Dec. 19, 2019", 2 pgs.
"Bi-Cruciate Stabilized Knee System", Design Rationale, Smith & Nephew Journal, (2006), 20 pgs.
"Brazil Application Serial No. BR1120130016698, Office Action dated Aug. 27, 2019", (W/ English Translation), 8 pages.
"Brazil Application Serial No. BR1120130016698, Response filed Dec. 9, 2019 to Office Action dated Aug. 27, 2019", w/ English Claims, 22 pgs.
"Brazil Application Serial No. BR1120130016736, Office Action dated Aug. 27, 2019", (with English translation), 8 pages.

(56) References Cited

OTHER PUBLICATIONS

"Brazil Application Serial No. BR1120130016736, Response filed Dec. 9, 2019 to Office Action dated Aug. 27, 2019", w/ English Claims, 25 pgs.
"Canadian Application Serial No. 2,806,321, Office Action dated Jan. 15, 2018", 3 pgs.
"Canadian Application Serial No. 2,806,321, Response filed Jan. 22, 2018 to Office Action dated Jan. 15, 2018", 7 pgs.
"Canadian Application Serial No. 2,806,321, Response filed Dec. 6, 2017 to Office Action dated Jun. 15, 2017", 12 pgs.
"Canadian Application Serial No. 2,806,325, Office Action dated Mar. 14, 2016", 4 pgs.
"Canadian Application Serial No. 2,806,325, Response filed Sep. 14, 2016 to Office Action dated Mar. 14, 2016", 17 pgs.
"Canadian Application Serial No. 2,806,326, Examiner's Rule 30(2) Requisition dated Sep. 20, 2018", 4 pgs.
"Canadian Application Serial No. 2,806,326, Office Action dated Feb. 8, 2018", 4 pgs.
"Canadian Application Serial No. 2,806,326, Office Action dated Jun. 19, 2017", 3 pgs.
"Canadian Application Serial No. 2,806,326, Response Filed Mar. 20, 2019 to Examiner's Rule 30(2) Requisition dated Sep. 20, 2018", 4 pgs.
"Canadian Application Serial No. 2,806,326, Response filed Jul. 20, 2018 to Office Action dated Feb. 8, 2018", 12 pgs.
"Canadian Application Serial No. 2,821,927, Office Action dated Jan. 25, 2018", 6 pgs.
"Canadian Application Serial No. 2,821,927, Response filed Jul. 18, 2018 to Office Action dated Jan. 25, 2018", 10 pgs.
"Canadian Application Serial No. 2,821,927, Voluntary Amendment dated Jun. 14, 2013", 7 pgs.
"Canadian Application Serial No. 2,824,527, Office Action dated Mar. 17, 2014", 2 pgs.
"Canadian Application Serial No. 2,824,527, Response filed Sep. 17, 2014 to Office Action dated Mar. 17, 2014", 14 pgs.
"Canadian Application Serial No. 2,856,070, Preliminary Amendment filed May 25, 2015", 27 pgs.
"Canadian Application Serial No. 2,856,571 Response filed Jan. 22, 2015 to Office Action dated Jul. 22, 2014", 24 pgs.
"Canadian Application Serial No. 2,856,571, Office Action dated Jul. 22, 2014", 2 pgs.
"Canadian Application Serial No. 2,863,375, Office Action dated Apr. 20, 2018", 3 pgs.
"Canadian Application Serial No. 2,863,375, Response filed Oct. 22, 2018 Office Action dated Apr. 20, 2018", 12 pgs.
"Canadian Application Serial No. 2,868,825, Office Action dated Dec. 27, 2018", 3 pgs.
"Canadian Application Serial No. 2,956,119, Examiner's Rule 30(2) Requisition dated Sep. 27, 2018", 4 pgs.
"Canadian Application Serial No. 2,956,119, Office Action dated Jan. 22, 2018", 3 pgs.
"Canadian Application Serial No. 2,956,119, Response Filed Mar. 27, 2019 to Examiner's Rule 30(2) Requisition dated Sep. 27, 2018", 7 pgs.
"Canadian Application Serial No. 2,989,184, Office Action dated Oct. 1, 2018", 4 pgs.
"Canadian Application Serial No. 2,989,184, Response filed Apr. 1, 2019 to Office Action dated Oct. 1, 2018", 10 pgs.
"Canadian Application Serial No. 3,063,415, Office Action dated Jul. 13, 2020", 3 pgs.
"Canadian Application Serial No. 2,806,321, Office Action dated Jun. 15, 2017", 3 pgs.
"Chinese Application Serial No. 201180045673.3, Office Action dated Feb. 14, 2016", (W/ English Translation), 17 pgs.
"Chinese Application Serial No. 201180045673.3, Office Action dated Mar. 29, 2015", (W/ English Translation), 6 pgs.
"Chinese Application Serial No. 201180045673.3, Office Action dated Aug. 12, 2015", (W/ English Translation), 7 pgs.
"Chinese Application Serial No. 201180045673.3, Response filed Jun. 19, 2015 to Office Action dated Mar. 29, 2015", (W/ English translation of claims), 11 pgs.
"Chinese Application Serial No. 201180045673.3, Response filed Oct. 27, 2015 to Office Action dated Aug. 12, 2015", (W/ English translation of claims), 9 pgs.
"Chinese Application Serial No. 201180045681.8, Office Action dated Jan. 22, 2015", (W/ English Translation), 11 pgs.
"Chinese Application Serial No. 201180045681.8, Response filed May 14, 2015 to Office Action dated Jan. 22, 2015", W/ English Claims, 17 pgs.
"Chinese Application Serial No. 201180045683.7, Office Action dated Mar. 9, 2015", (W/ English Translation), 6 pgs.
"Chinese Application Serial No. 201180045683.7, Response filed Jul. 14, 2015 to Office Action dated Mar. 9, 2015", (W/ English translation of claims), 30 pgs.
"Chinese Application Serial No. 201180045689.4, Office Action dated Jan. 5, 2015", (W/ English Translation), 4 pgs.
"Chinese Application Serial No. 201180045689.4, Office Action dated Feb. 2, 2016", w/English Translation, 11 pgs.
"Chinese Application Serial No. 201180045689.4, Office Action dated Aug. 5, 2015", (W/ English Translation), 11 pgs.
"Chinese Application Serial No. 201180045689.4, Response filed May 1, 2015 to Office Action dated Jan. 5, 2015", W/ English Claims, 13 pgs.
"Chinese Application Serial No. 201180067430.X, Office Action dated Aug. 28, 2014", (W/ English Translation), 8 pgs.
"Chinese Application Serial No. 201180067430.X, Response filed Jan. 4, 2015 to Office Action dated Sep. 26, 2014", (W/ English Translation), 14 pgs.
"Chinese Application Serial No. 201180067757.7, Office Action dated Mar. 2, 2015", (W/ English Translation), 18 pgs.
"Chinese Application Serial No. 201180067757.7, Office Action dated Jun. 1, 2016", (W/ English Translation), 10 pgs.
"Chinese Application Serial No. 201180067757.7, Office Action dated Nov. 16, 2015", (W/ English Translation), 17 pgs.
"Chinese Application Serial No. 201180067757.7, Response filed Jan. 27, 2016 to Office Action dated Nov. 16, 2015", (W/ English Translation of Claims), 12 pgs.
"Chinese Application Serial No. 201180067757.7, Response filed Jul. 10, 2015 to Office Action dated Mar. 2, 2015", (W/ English Translation), 13 pgs.
"Chinese Application Serial No. 201180067757.7, Response filed Aug. 11, 2016 to Office Action dated Jun. 1, 2016", (W/ English Translation Of Claims), 9 pgs.
"Chinese Application Serial No. 201180067757.7, Voluntary Amendment dated Feb. 14, 2014", (W/ English Translation of Claims), 8 pgs.
"Chinese Application Serial No. 201280067473.2, Office Action dated Feb. 1, 2016", (W/ English Translation), 4 pgs.
"Chinese Application Serial No. 201280067473.2, Office Action dated May 20, 2015", (W/ English Translation), 15 pgs.
"Chinese Application Serial No. 201280067473.2, Office Action dated Nov. 20, 2015", W/ English Translation of Claims, 7 pgs.
"Chinese Application Serial No. 201280067473.2, Response filed Apr. 7, 2016 to Office Action dated Feb. 1, 2016", (W/ English translation of claims), 11 pgs.
"Chinese Application Serial No. 201280067473.2, Response filed Sep. 7, 2015 to Office Action dated May 20, 2015", (W/ English translation of claims), 12 pgs.
"Chinese Application Serial No. 201280067473.2, Response filed Dec. 4, 2015 to Office Action dated Nov. 20, 2015", w/English Claims, 11 pgs.
"Chinese Application Serial No. 201280067481.7, Office Action dated Sep. 30, 2015", (W/ English Translation), 7 pgs.
"Chinese Application Serial No. 201280071940.9, Office Action dated Jul. 22, 2015", (W/ English Translation), 13 pgs.
"Chinese Application Serial No. 201280071940.9, Preliminary Amendment filed Mar. 23, 2015", W/ English Claims, 11 pgs.
"Chinese Application Serial No. 201380028572.4, Office Action dated Aug. 13, 2015", (W/ English Translation), 16 pgs.
"Chinese Application Serial No. 201380028683.5, Office Action dated Jun. 27, 2016", (W/ English Translation), 8 pgs.

(56) References Cited

OTHER PUBLICATIONS

"Chinese Application Serial No. 201380028683.5, Office Action dated Nov. 4, 2015", (W/ English Translation), 16 pgs.
"Chinese Application Serial No. 201380028683.5, Office Action dated Dec. 30, 2016", (W/ English Translation), 4 pgs.
"Chinese Application Serial No. 201380028683.5, Response filed Feb. 8, 2017 to Office Action dated Dec. 30, 2016", (W/ English Translation), 13 pgs.
"Chinese Application Serial No. 201380028683.5, Response filed Mar. 18, 2016 to Office Action dated Nov. 4, 2015", (W/ English Translation of Claims), 11 pgs.
"Chinese Application Serial No. 201380028683.5, Response filed Sep. 6, 2016 to Office Action dated Jun. 27, 2016", (W/ English Translation of Claims), 11 pgs.
"Chinese Application Serial No. 201510394094.X, Office Action dated May 24, 2017", (W/ English Translation), 11 pgs.
"Chinese Application Serial No. 201510394094.X, Office Action dated Aug. 30, 2016", (W/ English Translation), 14 pgs.
"Chinese Application Serial No. 201510394094.X, Office Action dated Nov. 3, 2017", (W/ English Translation), 10 pgs.
"Chinese Application Serial No. 201510394094.X, Response filed Jan. 16, 2017 to Office Action dated Aug. 30, 2016", (W/ English Translation of Claims), 11 pgs.
"Chinese Application Serial No. 201510394094.X, Response filed Jan. 18, 2018 to Office Action dated Nov. 3, 2017", (W/ English Claims), 10 pgs.
"Chinese Application Serial No. 201510394094.X, Response filed Jul. 10, 2017 to Office Action dated May 24, 2017", (W/ English Translation), 10 pgs.
"Chinese Application Serial No. 201510640436.1, Office Action dated Sep. 28, 2016", (W/ English Translation), 13 pgs.
"Chinese Application Serial No. 201510640436.1, Response filed Feb. 16, 2017 to Office Action dated Sep. 28, 2016", (W/ English Translation), 18 pgs.
"Chinese Application Serial No. 201610634595.5, Office Action dated Apr. 20, 2018", (W/ English Translation), 8 pgs.
"Chinese Application Serial No. 201610634595.5, Office Action dated Jun. 21, 2017", w/English Translation, 9 pgs.
"Chinese Application Serial No. 201610634595.5, Response filed Jun. 4, 2018 to Office Action dated Apr. 20, 2018", (W/ English Translation of Claims), 8 pgs.
"Chinese Application Serial No. 201610634595.5, Response filed Nov. 3, 2017 to Office Action dated Jun. 21, 2017", w/English Claims, 8 pgs.
"Chinese Application Serial No. 201610685172.6, Office Action dated Apr. 10, 2017", (W/ English Translation), 11 pgs.
"Chinese Application Serial No. 201610685172.6, Office Action dated Sep. 28, 2017", (W/ English Translation), 9 pgs.
"Chinese Application Serial No. 201610685172.6, Response filed Dec. 13, 2017 to Office Action dated Sep. 28, 2017", (W/ English Claims), 13 pgs.
"Chinese Application Serial No. 201680061268.3, Office Action dated Apr. 24, 2019", (W/ English Translation), 11 pgs.
"Chinese Application Serial No. 201680061268.3, Response filed Aug. 21, 2019 to Office Action dated Apr. 24, 2019", (W/ English Claims), 8 pgs.
"Chinese Application Serial No. 201880031319.7, Office Action dated May 15, 2020", (W/ English Translation), 12 pgs.
"Chinese Application Serial No. 201880031319.7, Response filed Jul. 22, 2020 to Office Action dated May 15, 2020", (W/ English Claims), 10 pgs.
"Complete Knee Solution Surgical Technique for the CR-Flex Fixed Bearing Knee", Zimmer Nexgen, (2003), 22 pgs.
"Euorpean Application Serial No. 18726670.5, Response to Communication pursuant to Rules 161(1) and 162 EPC filed Jul. 20, 2020", 9 pgs.
"European Application Serial No. 11738918.9, Examination Notification Art. 94(3) dated Oct. 23, 2014", 5 pgs.
"European Application Serial No. 11738918.9, Preliminary Amendment dated Sep. 24, 2013", 11 pgs.
"European Application Serial No. 11738918.9, Response filed Mar. 2, 2015 to Examination Notification Art. 94(3) dated Oct. 23, 2014", 14 pgs.
"European Application Serial No. 11738919.7, Examination Notification Art. 94(3) dated Jul. 7, 2014", 4 pgs.
"European Application Serial No. 11738919.7, Preliminary Amendment filed Nov. 4, 2013", 25 pgs.
"European Application Serial No. 11738919.7, Response filed Nov. 13, 2014 to Examination Notification Art. 94(3) dated Jul. 7, 2014", 14 pgs.
"European Application Serial No. 11738920.5, Communication Pursuant to Article 94(3) EPC dated Mar. 15, 2016", 4 pgs.
"European Application Serial No. 11738920.5, Preliminary Amendment dated Sep. 24, 2013", 9 pgs.
"European Application Serial No. 11738920.5, Response filed Jul. 25, 2016 to Communication Pursuant to Article 94(3) EPC dated Mar. 15, 2016", 6 pgs.
"European Application Serial No. 11738920.5, Response filed Sep. 24, 2013 to Communication pursuant to Rules 161(2) and 162 EPC dated Mar. 15, 2013", 22 pgs.
"European Application Serial No. 11758060.5, Communication Pursuant to Article 94(3) EPC dated Jul. 12, 2016", 3 pgs.
"European Application Serial No. 11758060.5, Communication Pursuant to Article 94(3) EPC dated Dec. 11, 2015", 4 pgs.
"European Application Serial No. 11758060.5, Preliminary Amendment filed Nov. 4, 2013", 15 pgs.
"European Application Serial No. 11758060.5, Response filed Apr. 21, 2016 to Communication Pursuant to Article 94(3) EPC dated Dec. 11, 2015", 16 pgs.
"European Application Serial No. 11758060.5, Response filed Nov. 15, 2016 to Communication Pursuant to Article 94(3) EPC dated Jul. 12, 2016", 23 pgs.
"European Application Serial No. 11802835.6, Communication Pursuant to Article 94(3) EPC dated Dec. 11, 2017", 4 pgs.
"European Application Serial No. 11802835.6, Response filed Apr. 23, 2018 to Office Action dated Dec. 11, 2017", 16 pgs.
"European Application Serial No. 11808493.8, Communication Pursuant to Article 94(3) EPC dated Dec. 7, 2015", 4 pgs.
"European Application Serial No. 11808493.8, Examination Notification Art. 94(3) dated Feb. 20, 2015", 6 pgs.
"European Application Serial No. 11808493.8, Response filed Feb. 26, 2014 to Communication pursuant to Rules 161(1) and 162 EPC dated Aug. 16, 2013", 14 pgs.
"European Application Serial No. 11808493.8, Response filed Apr. 18, 2016 to Communication Pursuant to Article 94(3) EPC dated Dec. 7, 2015", 15 pgs.
"European Application Serial No. 11808493.8, Response filed Jul. 2, 2015 to Examination Notification Art. 94(3) dated Feb. 20, 2015", 13 pgs.
"European Application Serial No. 11815029.1, Communication Pursuant to Article 94(3) EPC dated Sep. 29, 2016", 4 pgs.
"European Application Serial No. 11815029.1, Extended European Search Report dated Dec. 10, 2013", 8 pgs.
"European Application Serial No. 11815029.1, Response filed Apr. 10, 2017 to Communication Pursuant to Article 94(3) EPC dated Sep. 29, 2016", 22 pgs.
"European Application Serial No. 11815029.1, Response filed Jul. 21, 2014 Extended European Search Report dated Dec. 10, 2013", 15 pgs.
"European Application Serial No. 12718882.9, Communication Pursuant to Article 94(3) EPC dated Dec. 1, 2015", 11 pgs.
"European Application Serial No. 12718882.9, Response filed Feb. 10, 2015 to Communication Pursuant to Rules 161(1) and 162 EPC dated Jul. 31, 2014", 11 pgs.
"European Application Serial No. 12718882.9, Response filed Apr. 11, 2016 to Communication Pursuant to Article 94(3) EPC dated Dec. 1, 2015", 12 pgs.
"European Application Serial No. 12718883.7, Communication Pursuant to Article 94(3) EPC dated Dec. 2, 2015", 4 pgs.
"European Application Serial No. 12718883.7, Communication Pursuant to Rules 161(1) and 162 EPC dated Jul. 31, 2014", 2 pgs.
"European Application Serial No. 12718883.7, Intention to Grant dated May 20, 2016", 5 pgs.

(56) References Cited

OTHER PUBLICATIONS

"European Application Serial No. 12718883.7, Response filed Feb. 10, 2015 to Communication Pursuant to Rules 161(1) and 162 EPC dated Jul. 31, 2014", 16 pgs.
"European Application Serial No. 12718883.7, Response filed Apr. 12, 2016 to Communication Pursuant to Article 94(3) EPC dated Dec. 2, 2015", 30 pgs.
"European Application Serial No. 12719236.7 Response filed Feb. 9, 2015 to Communication Pursuant to Rules 161(1) and 162 EPC dated Jul. 30, 2014", 10 pgs.
"European Application Serial No. 12719236.7, Decision to Grant dated Feb. 18, 2016", 3 pgs.
"European Application Serial No. 12719236.7, Office Action dated Aug. 27, 2015", 7 pgs.
"European Application Serial No. 12720352.9 Response filed Feb. 9, 2015 to Communication Pursuant to Rules 161(1) and 162 EPC dated Jul. 30, 2014", 10 pgs.
"European Application Serial No. 12756058.9, Communication Pursuant to Article 94(3) EPC dated Feb. 18, 2019", 4 pgs.
"European Application Serial No. 12756058.9, Office Action dated Jan. 17, 2017", 5 Pgs.
"European Application Serial No. 12756058.9, Preliminary Amendment filed Apr. 20, 2015", 12 pgs.
"European Application Serial No. 12756058.9, Response filed May 26, 2017 to Office Action dated Jan. 17, 2017", 16 pgs.
"European Application Serial No. 12756058.9, Response filed Jun. 28, 2019 to Communication Pursuant to Article 94(3) EPC dated Feb. 18, 2019", 21 pgs.
"European Application Serial No. 12756869.9 Response filed Feb. 10, 2015 to Communication Pursuant to Rule 161(1) and 162 EPC dated Jul. 31, 2014", 14 pgs.
"European Application Serial No. 12756869.9, Examination Notification Art. 94(3) dated Jul. 2, 2015", 4 pgs.
"European Application Serial No. 12756869.9, Response filed Nov. 12, 2015 to Examination Notification Art. 94(3) dated Jul. 2, 2015", 28 pgs.
"European Application Serial No. 13716636.9, Communication Pursuant to Article 94(3) EPC dated Nov. 16, 2015", 4 pgs.
"European Application Serial No. 13716636.9, Communication Pursuant to Article 94(3) EPC dated Nov. 17, 2016", 4 pgs.
"European Application Serial No. 13716636.9, Communication Pursuant to Article 94(3) EPC dated Jun. 6, 2016", 5 pgs.
"European Application Serial No. 13716636.9, Communication pursuant to Rules 161(1) and 162 EPC dated Dec. 12, 2014", 2 pgs.
"European Application Serial No. 13716636.9, Response filed Mar. 24, 2016 to Communication Pursuant to Article 94(3) EPC dated Nov. 16, 2015", 18 pgs.
"European Application Serial No. 13716636.9, Response filed Mar. 27, 2017 to Communication Pursuant to Article 94(3) EPC dated Nov. 17, 2016", 15 pgs.
"European Application Serial No. 13716636.9, Response filed Jun. 22, 2015 to Communication pursuant to Rules 161(1) and 162 EPC dated Dec. 12, 2014", 10 pgs.
"European Application Serial No. 13716636.9, Response filed Oct. 17, 2016 to Communication Pursuant to Article 94(3) EPC dated Jun. 6, 2016", 5 pgs.
"European Application Serial No. 14190180.1, Extended European Search Report dated Sep. 24, 2015", 8 pgs.
"European Application Serial No. 15160934.4, Communication Pursuant to Article 94(3) EPC dated Apr. 26, 2018", 5 pgs.
"European Application Serial No. 15160934.4, Extended European Search Report dated Jun. 1, 2016", 8 pgs.
"European Application Serial No. 15160934.4, Response filed Aug. 30, 2018 to Communication Pursuant to Article 94(3) EPC dated Apr. 26, 2018", 63 pgs.
"European Application Serial No. 15160934.4, Response filed Dec. 21, 2016 to Extended European Search Report dated Jun. 1, 2016", 5 pgs.
"European Application Serial No. 15174394.5 Extended European Search Report dated Mar. 21, 2016", 8 pgs.

"European Application Serial No. 15174394.5, Response filed Nov. 18, 2016 to Extended European Search Report dated Mar. 21, 2016", 12 pgs.
"European Application Serial No. 15191781.2, Communication Pursuant to Article 94(3) EPC dated Jan. 8, 2018", 4 pgs.
"European Application Serial No. 15191781.2, Extended European Search Report dated Mar. 1, 2017", 8 pgs.
"European Application Serial No. 15191781.2, Response filed May 17, 2018 to Communication Pursuant to Article 94(3) EPC dated Jan. 8, 2018", 58 pgs.
"European Application Serial No. 15191781.2, Response filed Sep. 28, 2017 to Extended European Search Report dated Mar. 1, 2017", 14pgs.
"European Application Serial No. 16156228.5, Extended European Search Report dated May 11, 2017", 5 pgs.
"European Application Serial No. 16183635.8, Extended European Search Report dated Jun. 30, 2017", 9 pgs.
"European Application Serial No. 16183635.8, Response filed Mar. 27, 2018 to Extended European Search Report dated Jun. 30, 2017", 8 pgs.
"European Application Serial No. 16189084.3, Extended European Search Report dated Oct. 9, 2017", 9 pgs.
"European Application Serial No. 16189084.3, Response filed May 10, 2018 to Extended European Search Report dated Oct. 9, 2017", 20 pgs.
"European Application Serial No. 16770657.1, Communication Pursuant to Article 94(3) EPC dated May 20, 2019", 3 pgs.
"European Application Serial No. 16770657.1, Response filed Sep. 30, 2019 to Communication Pursuant to Article 94(3) EPC dated May 20, 2019", 26 pgs.
"European Application Serial No. 16770657.1, Response filed Nov. 26, 2018 to Office Action dated May 14, 2018", 17 pgs.
"European Application Serial No. 17157909.7, Extended European Search Report dated Jul. 17, 2018", 7 pgs.
"European Application Serial No. 17157909.7, Response Filed Feb. 15, 2019 to Extended European Search Report dated Jul. 17, 2018", 37 pgs.
"European Application Serial No. 17163432.2, Extended European Search Report dated May 14, 2018", 6 pgs.
"European Application Serial No. 17163440.5, Extended European Search Report dated Jan. 3, 2019", 16 pgs.
"European Application Serial No. 17163440.5, Partial European Search Report dated Jul. 23, 2018", 15 pgs.
"European Application Serial No. 17163440.5, Response filed Jul. 22, 2019 to Extended European Search Report dated Jan. 3, 2019", 14 pgs.
"European Application Serial No. 17168095.2, Extended European Search Report dated Jun. 8, 2018", 8 pgs.
"European Application Serial No. 17168095.2, Response Filed Jan. 17, 2019 Extended European Search Report dated Jun. 8, 2018", 29 pgs.
"European Application Serial No. 17168308.9, Extended European Search Report dated Jun. 13, 2018", 8 pgs.
"European Application Serial No. 17168308.9, Response Filed Jan. 17, 2019 to Extended European Search Report dated Jun. 13, 2018", 24 pgs.
"European Application Serial No. 18206326.3, Extended European Search Report dated Apr. 15, 2019", 10 pgs.
"European Application Serial No. 18206326.3, Response filed Nov. 22, 2019 to Extended European Search Report dated Apr. 15, 2019", 15 pgs.
"European Application Serial No. 18711801.3, Response to Communication pursuant to Rules 161(1) and 162 EPC filed May 7, 2020", 14 pgs.
"European Application Serial No. 19171990.5, Extended European Search Report dated Oct. 16, 2019", 8 pgs.
"European Application Serial No. 19171990.5, Response filed May 13, 2020 to Extended European Search Report dated Oct. 16, 2019", 31 pgs.
"Gender Solutions Natural Knee Flex System: Because Men and Women are Different", Zimmer, Inc., (2007, 2009), 6 pg.
"Gender Solutions Natural Knee Flex System: Surgical Technique", (2007, 2008, 2009), 36 pgs.

(56) References Cited

OTHER PUBLICATIONS

"Gender Solutions Natural-Knee Flex System", Zimmer, Inc., (2007, 2009), 6 pgs.
"Indian Application Serial No. 1544/DELNP/2013, Office Action dated May 21, 2019", (W/ English Translation), 10 pgs.
"Indian Application Serial No. 1544/DELNP/2013, Response filed Nov. 18, 2019 to Office Action dated May 21, 2019", (W/ English Translation), 34 pgs.
"Indian Application Serial No. 1545/DELNP/2013, Office Action dated Dec. 9, 2019", (with English translation), 8 pages.
"Indian Application Serial No. 1545/DELNP/2013, Response filed Jun. 9, 2020 to Office Action dated Dec. 9, 2019", (W/ English Claims), 78 pgs.
"International Application Serial No. PCT/US2011/045077, International Preliminary Report on Patentability dated Jul. 5, 2012", 23 pgs.
"International Application Serial No. PCT/US2011/045077, International Search Report and Written Opinion dated Jan. 9, 2012", 15 pgs.
"International Application Serial No. PCT/US2011/045078, International Preliminary Report on Patentability dated Feb. 7, 2013", 11 pgs.
"International Application Serial No. PCT/US2011/045078, International Search Report and Written Opinion dated Jan. 9, 2012", 14 pgs.
"International Application Serial No. PCT/US2011/045080, International Preliminary Report on Patentability dated Feb. 7, 2013", 13 pgs.
"International Application Serial No. PCT/US2011/045080, International Search Report dated Jan. 9, 2012", 7 pgs.
"International Application Serial No. PCT/US2011/045080, Written Opinion dated Jan. 9, 2012", 11 pgs.
"International Application Serial No. PCT/US2011/045082, International Preliminary Report on Patentability dated Feb. 7, 2013", 11 pgs.
"International Application Serial No. PCT/US2011/045082, International Search Report dated Jan. 9, 2012", 5 pgs.
"International Application Serial No. PCT/US2011/045082, Written Opinion dated Jan. 9, 2012", 10 pgs.
"International Application Serial No. PCT/US2011/045083, International Preliminary Report on Patentability dated Feb. 7, 2013", 8 pgs.
"International Application Serial No. PCT/US2011/045083, International Search Report dated Dec. 7, 2011", 2 pgs.
"International Application Serial No. PCT/US2011/045083, Written Opinion dated Dec. 7, 2011", 6 pgs.
"International Application Serial No. PCT/US2011/051021, International Preliminary Report on Patentability dated Mar. 21, 2013", 8 pgs.
"International Application Serial No. PCT/US2011/051021, International Search Report dated Nov. 23, 2011", 12 pgs.
"International Application Serial No. PCT/US2011/051021, Written Opinion dated Nov. 23, 2011", 7 pgs.
"International Application Serial No. PCT/US2011/064435, International Preliminary Report on Patentability dated Jun. 27, 2013", 9 pgs.
"International Application Serial No. PCT/US2011/064435, Search Report dated Jun. 21, 2012", 5 pgs.
"International Application Serial No. PCT/US2011/064435, Written Opinion dated Jun. 21, 2012", 7 pgs.
"International Application Serial No. PCT/US2011/065683, International Preliminary Report on Patentability dated Jun. 27, 2013", 11 pgs.
"International Application Serial No. PCT/US2011/065683, International Search Report dated Apr. 24, 2012", 12 pgs.
"International Application Serial No. PCT/US2011/065683, Written Opinion dated Apr. 24, 2012", 10 pgs.
"International Application Serial No. PCT/US2012/035679, International Preliminary Report on Patentability dated May 30, 2014", 8 pgs.
"International Application Serial No. PCT/US2012/035679, International Search Report dated Jun. 8, 2012", 4 pgs.
"International Application Serial No. PCT/US2012/035679, Written Opinion dated Jun. 8, 2012", 7 pgs.
"International Application Serial No. PCT/US2012/035680, International Preliminary Report on Patentability dated May 30, 2014", 13 pgs.
"International Application Serial No. PCT/US2012/035680, Search Report dated Oct. 9, 2012", 7 pgs.
"International Application Serial No. PCT/US2012/035680, Written Opinion dated Oct. 9, 2012", 11 pgs.
"International Application Serial No. PCT/US2012/035683, International Preliminary Report on Patentability dated May 30, 2014", 9 pgs.
"International Application Serial No. PCT/US2012/035683, International Search Report and Written Opinion dated Jun. 5, 2012", 12 pgs.
"International Application Serial No. PCT/US2012/035684, International Preliminary Report on Patentability dated May 30, 2014", 14 pgs.
"International Application Serial No. PCT/US2012/035684, International Search Report dated Aug. 8, 2012", 9 pgs.
"International Application Serial No. PCT/US2012/035684, Written Opinion dated Jun. 8, 2012", 12 pgs.
"International Application Serial No. PCT/US2012/052132, International Preliminary Report on Patentability dated Jun. 5, 2014", 12 pgs.
"International Application Serial No. PCT/US2012/052132, International Search Report dated Jan. 10, 2013", 5 pgs.
"International Application Serial No. PCT/US2012/052132, Invitation to Pay Additional Fees and Partial Search Report dated Nov. 15, 2012", 7 pgs.
"International Application Serial No. PCT/US2012/052132, Written Opinion dated Jan. 10, 2013", 10 pgs.
"International Application Serial No. PCT/US2012/052340, International Preliminary Report on Patentability dated Aug. 14, 2014", 8 pgs.
"International Application Serial No. PCT/US2012/052340, Search Report dated Oct. 12, 2012", 4 pgs.
"International Application Serial No. PCT/US2012/052340, Written Opinion dated Oct. 12, 2012", 6 pgs.
"International Application Serial No. PCT/US2013/034286, International Preliminary Report on Patentability dated Oct. 9, 2014", 8 pgs.
"International Application Serial No. PCT/US2013/034286, International Search Report dated Jun. 25, 2013", 6 pgs.
"International Application Serial No. PCT/US2013/034286, Written Opinion dated Jun. 25, 2013", 6 pgs.
"International Application Serial No. PCT/US2013/034293, International Preliminary Report on Patentability dated Oct. 9, 2014", 9 pgs.
"International Application Serial No. PCT/US2013/034293, International Search Report dated Jun. 25, 2013", 6 pgs.
"International Application Serial No. PCT/US2013/034293, Written Opinion dated Jun. 25, 2013", 7 pgs.
"International Application Serial No. PCT/US2016/052163, International Preliminary Report on Patentability dated Apr. 5, 2018", 10 pgs.
"International Application Serial No. PCT/US2016/052163, International Search Report dated Jan. 20, 2017", 7 pgs.
"International Application Serial No. PCT/US2016/052163, Invitation to Pay Add'l Fees and Partial Search Report dated Nov. 7, 2016", 7 pgs.
"International Application Serial No. PCT/US2016/052163, Written Opinion dated Jaun. 20, 2017", 8 pgs.
"International Application Serial No. PCT/US2018/021571, International Preliminary Report on Patentability dated Sep. 19, 2019", 8 pgs.
"International Application Serial No. PCT/US2018/021571, International Search Report dated Jun. 7, 2018", 6 pgs.
"International Application Serial No. PCT/US2018/021571, Written Opinion dated Jun. 7, 2018", 6 pgs.

(56) References Cited

OTHER PUBLICATIONS

"International Application Serial No. PCT/US2018/031177, International Preliminary Report on Patentability dated Nov. 21, 2019", 8 pgs.
"International Application Serial No. PCT/US2018/031177, International Search Report dated Jul. 31, 2018", 6 pgs.
"International Application Serial No. PCT/US2018/031177, Written Opinion dated Jul. 31, 2018", 6 pgs.
"Intramedullary Instrumentation Surgical Technique for the NexGen Cruciate Retaining & Legacy Posterior Stabilized Knee", Zimmer, Inc. Nexgen Complete Knee Solution, 97-5973-102, Rev. 1, (1995, 1997, 1998), 36 pgs.
"Japanese Application Serial No. 2015-162707, Office Action dated Jun. 28, 2016", (W/ English Translation), 8 pgs.
"Japanese Application Serial No. 2013-521854, Notice of Reason for Rejection dated Sep. 16, 2014", (W/ English Translation), 6 pgs.
"Japanese Application Serial No. 2013-521854, Response filed Dec. 16, 2014 to Notice of Reason for Rejection dated Sep. 16, 2014", W/ English Claims, 11 pgs.
"Japanese Application Serial No. 2013-521855, Amendment filed Jul. 22, 2014", (W/ English Translation), 20 pgs.
"Japanese Application Serial No. 2013-521855, Office Action dated Mar. 24, 2015", W/ English Translation, 8 pgs.
"Japanese Application Serial No. 2013-521856, Notice of Allowance dated Jan. 5, 2016", w/English Translation, 6 pgs.
"Japanese Application Serial No. 2013-521856, Office Action dated Sep. 1, 2015", (W/ English Translation), 5 pgs.
"Japanese Application Serial No. 2013-521856, Response filed Dec. 1, 2015 to Office Action dated Sep. 1, 2015", w/English Translation, 9 pgs.
"Japanese Application Serial No. 2013-521857, Notice of Allowance dated Feb. 9, 2016", w/English Translation, 6 pgs.
"Japanese Application Serial No. 2013-521857, Notice of Reasons for Rejection dated Aug. 18, 2015", (W/ English Translation), 6 pgs.
"Japanese Application Serial No. 2013-521857, Preliminary Amendment filed May 18, 2014" (W/ English translation of claims), 9 pgs.
"Japanese Application Serial No. 2013-521857, Response filed Jan. 25, 2016 to Notice of Reasons for Rejection dated Aug. 18, 2015", (W/ English Translation), 17 pgs.
"Japanese Application Serial No. 2013-544655, Office Action dated Mar. 8, 2016", (W/ English Translation), 8 pgs.
"Japanese Application Serial No. 2013-544655, Office Action dated Sep. 29, 2015", (W/ English Translation), 7 pgs.
"Japanese Application Serial No. 2013-544655, Response filed Jan. 4, 2016 to Office Action dated Sep. 29, 2015", (English Translation of Claims), 14 pgs.
"Japanese Application Serial No. 2013-544655, Response filed Jul. 14, 2016 to Office Action dated Mar. 8, 2016", (w/ English Translation of Claims), 13 pgs.
"Japanese Application Serial No. 2013-544858, Request for Examination filed Feb. 4, 2014", (With English Translation), 14 pgs.
"Japanese Application Serial No. 2014-121515, Notice of Reasons for Rejection dated Jan. 5, 2016", (W/ English Translation), 9 pgs.
"Japanese Application Serial No. 2014-121515, Office Action dated Jun. 2, 2015", (W/ English Translation), 10 pgs.
"Japanese Application Serial No. 2014-121515, Response filed May 11, 2016 to Notice of Reasons for Rejection dated Jan. 5, 2016", (W/ English Translation Of Claims), 11 pgs.
"Japanese Application Serial No. 2014-121515, Response filed Aug. 20, 2015 to Office Action dated Jun. 2, 2015", (W/ English Translation Of Claims), 6 pgs.
"Japanese Application Serial No. 2014-542297, Office Action dated May 31, 2016", (W/ English Translation Of Claims), 6 pgs.
"Japanese Application Serial No. 2014-542297, Office Action dated Jun. 30, 2015", (W/ English Translation), 10 pgs.
"Japanese Application Serial No. 2014-542297, Office Action dated Nov. 24, 2015", (W/ English Translation), 10 pgs.
"Japanese Application Serial No. 2014-542297, Response filed Feb. 23, 2016 to Office Action dated Nov. 24, 2015", (W/ English Translation Of Claims), 15 pgs.
"Japanese Application Serial No. 2014-542297, Response filed Jun. 8, 2016 to Office Action dated May 31, 2016", (W/ English Translation Of Claims), 14 pgs.
"Japanese Application Serial No. 2014-542297, Response filed Sep. 28, 2015 to Office Action dated Jun. 30, 2015", (W/ English Translation Of Claims), 16 pgs.
"Japanese Application Serial No. 2014-542301, Office Action dated May 12, 2015", (W/ English Translation), 6 pgs.
"Japanese Application Serial No. 2014-542301, Response filed Aug. 10, 2015 to Office Action dated May 12, 2015", (W/ English translation of claims), 21 pgs.
"Japanese Application Serial No. 2014-554709, Office Action dated Jul. 5, 2016", (W/ English Translation), 6 pgs.
"Japanese Application Serial No. 2014-554709, Preliminary Amendment filed Jul. 29, 2015", (W/ English translation of claims), 8 pgs.
"Japanese Application Serial No. 2014-554709, Response filed Dec. 19, 2016 to Office Action dated Jul. 5, 2016", (W/ English Translation of Claims), 11 pgs.
"Japanese Application Serial No. 2015-162707, Office Action dated Nov. 29, 2016", (W/ English Translation), 3 pgs.
"Japanese Application Serial No. 2015-162707, Response filed Jan. 26, 2017 to Office Action dated Nov. 27, 2016", (W/ English Translation), 16 pgs.
"Japanese Application Serial No. 2015-199496, Office Action dated Sep. 6, 2016", (W/ English Translation), 5 pgs.
"Japanese Application Serial No. 2015-199496, Response filed Dec. 5, 2016 to Office Action dated Sep. 6, 2016", (W/ English Translation of Claims), 9 pgs.
"Japanese Application Serial No. 2015-503563, Office Action dated Dec. 20, 2016", (W/ English Translation), 10 pgs.
"Japanese Application Serial No. 2015-503563, Response Filed Mar. 13, 2017 to Office Action dated Dec. 20, 2016", (W/ English Translation), 9 pgs.
"Japanese Application Serial No. 2016-145390, Office Action dated Apr. 25, 2017", (W/ English Translation), 5 pgs.
"Japanese Application Serial No. 2016-145390, Response filed Jul. 3, 2017 to Office Action dated Apr. 25, 2017", (W/ English Translation of Claims), 16 pgs.
"Japanese Application Serial No. 2017-161246, Office Action dated May 15, 2018", (W/ English Translation), 6 pgs.
"Japanese Application Serial No. 2019-562605, Notification of Reasons for Refusal dated Jun. 16, 2020", (W/ English Translation), 7 pgs.
"Japanese Application Serial No. 2019-562605, Response filed Sep. 15, 2020 to Notification of Reasons for Refusal dated Jun. 16, 2020", (W/ English Claims), 15 pgs.
"Journey II XR, Bi-Cruciate Retaining Knee System", Smith & Nephew, Surgical Technique, (2015), 40 pgs.
"Legacy Implant Options", Nexgen Complete Knee Solution, (2002), 8 pgs.
"LPS-Flex Fixed Bearing Knee: Surgical Technique", Zimmer, Inc., (2004, 2007, 2008), 16 pgs.
"Mexican Application Serial No. MX/a/2013/000988, Office Action dated Mar. 18, 2015", w/English Claims, 17 pgs.
"Mexican Application Serial No. MX/a/2013/000988, Response filed Jun. 1, 2015 to Office Action dated Mar. 18, 2015", (W/ English Translation), 12 pgs.
"Mexican Application Serial No. MX/A/2013/000988, Office Action dated Jun. 5, 2015", w/ summary in English, 6 pgs.
"Mexican Application Serial No. MX/A/2013/000990, Final Office Action dated Feb. 4, 2016", w/ summary in English, 4 pgs.
"Mexican Application Serial No. MX/A/2013/000990, Office Action dated Feb. 19, 2015", (W/ English Translation), 4 pgs.
"Mexican Application Serial No. MX/A/2013/000990, Response filed Apr. 29, 2015 to Office Action dated Feb. 19, 2015", W/ English Claims, 18 pgs.
"MIS Minimally Invasive Solution, The M/G Unicompartmental Knee Minimally Invasive Surgical Technique", Zimmer, Inc. Nexgen Complete Knee Solution, 97-5791-02, (Aug. 14, 2008), 27 pgs.
"Multi-Reference 4-in-1 Femoral Instrumentation Surgical Technique for NexGen Cruciate Retaining & NexGen Legacy Posterior Stabilized Knees", Zimmer, Inc. Nexgen Complete Knee Solution, 97-5973-402 Rev. 1, (1998, 2000), 18 pgs.

(56) References Cited

OTHER PUBLICATIONS

"Natural-Knee II Primary System Surgical Technique", Zimmer, Inc., (2005), 48 pgs.
"Nexgen Complete Knee Solution", Extramedullary/Intramedullary Tibial Resector: Surgical Technique, Zimmer, Inc. 97-5997-002-00 Rev. 2, (2000, 2008, 2009), 28 pgs.
"Nexgen Complete Knee Solution", Extramedullary/Intramedullary Tibial Resector: Surgical Technique, Zimmer, Inc. 97-5997-02 Rev 1, (2000), 26 pgs.
"Nexgen Complete Knee Solution for the Legacy Knee LPS-Flex Fixed Bearing Knee", Zimmer Surgical Technique, 97-5964-102-00, (2004, 2007), 12 pgs.
"NexGen Complete Knee Solution, Intramedullary Instrumentation Surgical Technique for the NexGen Cruciate Retaining & Legacy Posterior Stabilized Knee", Zimmer, Inc., (1995, 1997, 1998), 1-33.
"NexGen Implant Options Surgeon-Specific", Zimmer Inc., (2000), 16 pgs.
"NexGen LPS Fixed Knee: Surgical Technique", Zimmer Inc., (2002, 2008), 44 pgs.
"NexGen LPS-Flex Mobile and LPS-Mobile Bearing Knees", Zimmer, Inc., (2007, 2008), 4 pgs.
"NexGen Trabecular Metal Modular Plates", Zimmer Inc., (2007), 19 pgs.
"Persona "Medial Congruent Articular Surface" System Overview", Zimmer, Inc., (2015), 6 pgs.
"Persona "The Personalized Knee System"", Medial Congruent Sales Training, Zimmer, Inc., (Jul. 2015), 53 pgs.
"Persona "The Personalized Knee System" Medial Congruent Advanced Bearings", Zimmer, Inc., (2015), 2 pgs.
"Persona "The Personalized Knee System" Medial Congruent Articular Surface Design Rationale", Zimmer, Inc., (2015), 20 pgs.
"Persona "The Personalized Knee System" Persona Medial Congruent", Mar. 24-28, 2015 at the American Academy of Orthopaedic Surgeons (AAOS) Annual Meeting., (Mar. 2015), 1 pg.
"Persona "The Personalized Knee System" Surgical Technique", Zimmer, Inc., (2015), 72 pgs.
"Persona Medial Congruent Articular Surface", Sales Training, Zimmer Biomet, (Jan. 2016), 71 pgs.
"PFC Sigma Knee System with Rotating Platform Technical/ Monograph", Depuy PFC Sigma RP, 0611-29-050 (Rev. 3), (1999), 70 pgs.
"Primary/Revision Surgical Technique for NexGen Rotating Hinge Knee (RHK)", Zimmer, Inc. Nexgen Complete Knee Solution, 97-5880-02, (2002), 116 pgs.
"Revision Instrumentation Surgical Technique for Legacy Knee Constrained Condylar Knee", Zimmer, Inc. Nexgen Complete Knee Solution, 97-5994-202, (2001), 61 pgs.
"Russian Application Serial No. 2013106942, Office Action dated Apr. 16, 2015", W/ English Translation, 5 pgs.
"Russian Application Serial No. 2013106942, Response filed Jul. 15, 2015 Office Action dated Apr. 16, 2015", (W/ English translation of claims), 146 pgs.
"Russian Application Serial No. 2013106943, Office Action dated Jul. 1, 2015", (W/ English Translation), 6 pgs.
"Russian Application Serial No. 2013106943, Office Action dated Dec. 28, 2015", w/ partial English Translation, 6 pgs.
"Russian Application Serial No. 2013106943, Response filed Apr. 28, 2016 to Office Action dated Dec. 28, 2015", (W/ English translation of claims), 19 pgs.
"Russian Application Serial No. 2013106943, Response filed Oct. 30, 2015 to Office Action dated Jul. 1, 2015", (W/ English translation of claims), 21 pgs.
"South African Application Serial No. 2013/01327, Amendment filed Apr. 24, 2014", W/ English Translation, 4 pgs.
"South African Application Serial No. 2013/01328, Amendment filed Apr. 24, 2014", W/ English Translation, 4 pgs.
"Surgical Technique for Cruciate Retaining Knees and Revision Instrumentation Surgical Technique for Cruciate Retaining Augmentable Knees", Zimmer, Inc. Nexgen Complete Knee Solution, 97-5970-202, (2002), 130 pgs.

"Surgical Technique for the CR-Flex Fixed Bearing Knee", NexGen Complete Knee Solution, Zimmer, Inc., (2003), 22 pgs.
"Surgical Technique for the Legacy Knee LPS-Flex Fixed Bearing Knee", Zimmer, Inc. Nexgen Complete Knee Solution, 97-5964-02, Rev. 1, (2000, 2002), 15 pgs.
"Surgical Technique for the Legacy Posterior Stabilized Knees", Zimmer, Inc. Nexgen Complete Knee Solution, 97-5996-02, (2002), 43 pgs.
"Surgical Technique—Nexgen Complete Knee Solution for the Legacy Knee LPS-Flex Fixed Bearing Knee", Zimmer, Inc., (2004, 2007), 12 pgs.
"The Zimmer Institute Surgical Technique MIS Quad-Sparing Surgical Technique for Total Knee Arthroplasty", NExGen Complete Knee Solution, (2004), 55 pgs.
"Tibial Baseplate: Pocket Guide (United States Version)", Zimmer, Inc.,, (2009), 17 pgs.
"Trabecular Metal Monoblock Tibial Components", Zimmer, Inc., (2007), 4 pgs.
"Trabecular Metal Monoblock Tibial Components Surgical Technique Addendum", Nexgen Zimmer, Inc., (2005, 2007), 12 pgs.
"Trabecular Metal Tibial Tray: Surgical Technique", NexGen Zimmer, Inc., (2007, 2009), 16 pgs.
"Turkish Application Serial No. 11808493.8, Working Requirements mailed Feb. 17, 2020", 3 pgs.
"Turkish Application Serial No. 12718882.9, Working Requirements mailed Feb. 13, 2020", 3 pgs.
"Vanguard® ID Total Knee, Surgical Technique", Zimmer Biomet; 0682.1-GLBL-en-REV0317, (2017), 36 pgs.
"Zimmer MIS Intramedullary Instrumentation Surgical Technique For NexGen Cruciate Retaining & NexGen Legacy Posterior Stabilized Knees", printed 2005, 2009, Zimmer, Inc., (2009), 45 pgs.
"Zimmer Nexgen Cruciate Retaining (CR) and Legacy Knee Posterior Stabilized (LPS) Trabecular Metal Monoblock Tibias", Zimmer, Inc Surgical Technique Addendum, 97-7253-34, Rev. 3, (2004), 11 pgs.
"Zimmer NexGen CR-Flex and LPS-Flex Knees Surgical Technique with posterior Referencing Instrumentation.", Zimmer Inc., (2010, 2011), 48 pgs.
"Zimmer NexGen LCCK Surgical Technique for use with LCCK 4-in-1 Instrumentation", Zimmer, Inc.; copyright 2009, 2010, 2011, (May 2011), 52 pgs.
"Zimmer NexGen MIS Modular Tibial Plate and Keel Cemented Surgical Technique", Zimmer Inc., (2006, 2011), 26 pgs.
"Zimmer NexGen MIS Tibial Component", Brochure-97-5950-001-00 7.5mm, (2005, 2006). 8 pgs.
"Zimmer NexGen MIS Tibial Component Cemented Surgical Technique", Zimmer, Inc, #97-5950-002-00 Rev.1 1.5ML, (2005), 14 pgs.
"Zimmer NexGen MIS Tibial Component Cemented Surgical Technique", Zimmer Inc., (2005, 2006, 2008, 2009, 2010), 16 pgs.
"Zimmer NexGen Trabecular Metal Augments—Abbreviated Surgical Technique", Zimmer, Inc., (2004, 2006), 6 pgs.
"Zimmer NexGen Trabecular Metal Augments Surgical Technique for LCCK & Rotating Hing Knee Trabecular Metal Augments", Zimmer, Inc. 97-5448-02, Rev. 1, (2004), 6 pgs.
"Zimmer NexGen Trabecular Metal Primary Patella Surgical Technique", Zimmer. Inc., 97-7255-112-00, (2005), 10 pgs.
"Zimmer NexGen Trabecular Metal Tibial Tray", Surgical Technique, Zimmer, Inc., (2007, 2009), 16 pgs.
"Zimmer Patient Specific Instruments", Surgical Techniques for NexGen Complete Knee Solution Zimmer, Inc., (2010), 16 pgs.
Annayappa, Ramesh, "Tibial Prosthesis", U.S. Appl. No. 13/189,328, filed Jul. 22, 2011, 82 pgs.
Annayappa, Ramesh, et al., "Tibial Prosthesis", U.S. Appl. No. 13/189,324, filed Jul. 22, 2011, 50 pgs.
Bellemans, Johan, et al., "Is Neutral Mechanical Alignment Normal for All Patients?", Clinical Orthopaedics and Related Research; DOI 10.1007/s11999-011-1936-5, (Jun. 9, 2011), 9 pgs.
Ding, M., et al., "Age-related variations in the microstructure of human tibial cancellous bone", Journal of Orthopaedic Research, 20(3), (2002), 615-621.

(56) References Cited

OTHER PUBLICATIONS

Ding, M., et al., "Changes in the three-dimensional microstructure of human tibial cancellous bone in early osteoarthritis", Journal of Bone & Joint Surgery (British), 85-B(6), (Aug. 2003), 906-912.
Doyle, et al., "Comparative Analysis of Human Trabecular Bone and Polyurethane Foam", Purdue University., 1 pg.
Dunbar, M. J., et al., "Fixation of a Trabecular Metal Knee Arthroplasty Component: A Prospective Randomized Study", The Journal of Bone & Joint Surgery (American), vol. 91-A(7), (Jul. 2009), 1578-1586.
Edwards, Andrew, et al., "The Attachments of the Fiber Bundles of the Posterior Cruciate ligament: An Anatomic Study", Arthroscopy: The Journal of Arthroscopic and Related Surgery, vol. 23, No. 3, (Mar. 2008), 284-290.
Freeman, M.A.R., et al., "The Movement of the Knee Studied by Magnetic Resonance Imaging", Advanced Bearings—Clinical Orthopedics & Related Research 2003, (2003), 1 pg.
Hofmann, Aaron A, et al., "Posterior Stabilization in Total Knee Arthroplasty with Use of an Ultracongruent Polyethylene", The Journal of Arthroplasty vol. 15, No. 5, (2000), 576-583.
Hutt, Jonathan, et al., "Functional joint line obliquity after kinematic total knee arthroplasty", International Orthopaedics; DOI 10.1007/s00264-015-2733-7, (Mar. 21, 2015), 6 pgs.
Hvid, Ivan, et al., "Trabecular bone Strength Patterns at the Proximal Tibial Epiphysis", Journal of Orthopaedic Research, vol. 3, No. 4, (1985), 464-472.
Klostermann, et al., "Distribution of bone mineral density with age and gender in the proximal tibia", Clinical Biomechanics 19, 376-376.
Lorenz, Stephan, et al., "Radiological evaluation of the anterolateral and posteromedial bundle insertion sites of the posterior cruciate ligament", Knee Surg Sports Traumatol Arthosc, vol. 17, (2009), 683-690.
Moorman, Claude, et al., "Tibial Insertion of the Posterior Cruciate Ligament: A Sagittal Plane Analysis Using Gross, Histologic, and Radiographic Methods", Arthroscopy: The Journal of Arthroscopic and Related Surgery, vol. 24, No. 3, (Mar. 2008), 269-275.
Parisi, Raymond C, "Motion Facilitating Tibial Components for a Knee Prosthesis", U.S. Appl. No. 13/229,103, filed Sep. 9, 2011, 46 pgs.
Partovi, Hamid, "Flow-Through Latch and Edge-Triggered Flip-Flop Hybrid Elements", Proceedings of the IEEE International Solid-State Circuits Conference, Digest of Technical Papers and Slide Supplement, NexGen Inc., Milpitas, CA, (1996), 40 pgs.
Siggelkow, Elk, et al., "Impact of Tibia Bearing Surface and Femoral Component Design on Flexion Kinematics During Lunge", Mar. 28-31, 2015 at the Orthopaedic Research Society (ORS) Annual Meeting (Poster #1645), (Mar. 2015), 1 pg.
Siggelkow, Elk, et al., "Impact of Tibia Bearing Surface Design on Deep Knee Bend Kinematics", Mar. 24-28, 2015 at the AAOS Conference (Poster #P142), (Mar. 2015), 1 pg.
Stilling, et al., "Superior fixation of pegged trabecular metal over screw-fixed pegged porous titanium fiber mesh", Acta Orthopaedica., (2011), 177-186.
Victor, Jan M. K., et al., "Constitutional Varus Does Not Affect Joint Line Orientation in the Coronal Plane", Joint Line Orientation in the Coronal Plane; 472; DOI 10.1007/s11999-013-2898-6, (Jun. 4, 2013), pp. 98-104.
Wentorf, Mary S. S, "Asymmetric Tibial Components for a Knee Prosthesis", U.S. Appl. No. 13/189,338, filed Jul. 22, 2011, 58 pgs.
Wentorf, Mary S. S, "Asymmetric Tibial Components for a Knee Prosthesis", U.S. Appl. No. 13/189,339, filed Jul. 22, 2011, 52 pgs.
Wentorf, Mary S. S, "Asymmetric Tibial Components for a Knee Prosthesis", U.S. Appl. No. 13/189,336, filed Jul. 22, 2011, 60 pgs.
"U.S. Appl. No. 18/081,481, Preliminary Amendment filed Jan. 11, 2023", 6 pgs.
"U.S. Appl. No. 18/228,322, Preliminary Amendment filed Aug. 16, 2023", 6 pgs.
"European Application Serial No. 18726670.5, Communication Pursuant to Article 94(3) EPC dated Dec. 15, 2022", 5 pgs.
"European Application Serial No. 18726670.5, Response filed Apr. 25, 2023 to Communication Pursuant to Article 94(3) EPC dated Dec. 15, 2022", 35 pgs.
"European Application Serial No. 21177256.1, Communication Pursuant to Article 94(3) EPC dated Jun. 7, 2023", 4 pgs.
"European Application Serial No. 21177256.1, Response filed Dec. 21, 2022 to Extended European Search Report dated May 17, 2022", 35 pgs.
"European Application Serial No. 21178298.2, Response filed Dec. 21, 2022 to Extended European Search Report dated Mar. 1, 2022", 23 pgs.
"Japanese Application Serial No. 2021-097369, Response filed Sep. 12, 2022 to Notification of Reasons for Rejection dated Jun. 14, 2022", w/ English claims, 17 pgs.

* cited by examiner

| | | COMP. A | COMP. B | COMP. C | COMP. D | COMP. E | COMP. F | COMP. 12 |
|---|---|---|---|---|---|---|---|---|
| ANTERIOR | RADIUS (mm) SPAN | 31.5 -25° TO 0° | 28.5 -5° TO 0° | 36.3 -24° TO 0° | 33 -14° TO 0° | 33 -14° TO 0° | 36.3 -24° TO 0° | 25.8 -20° TO 0° |
| EXTENSION TO MID-FLEXION | RADIUS (mm) SPAN | 35.6 0° TO 43° | 28.5 0° TO 45° | 28.5 0° TO 21° 36.3 21° TO 45° | 54 0° TO 14° | 54 0° TO 18° | 54 0° TO 18° | |
| POSTERIOR | RADIUS (mm) SPAN | 18.4 43° TO 92° 18.9 92° TO 126° | 36.3 45° TO 62° 15.9 62° TO 90° 18.9 90° TO 124° | 19.24 45° TO 110° | 21 15° TO 143° | 19 18° TO 132° | 18.5 18° TO 79° 29.1 80° TO 111° | 25 0° TO 90° |
| HIGH FLEX | RADIUS (mm) SPAN | 10.2 126° TO 170° | 10.2 126° TO 170° | 10 110° TO 170° | N/A | 11.4 132° TO 170° | 11.5 111° TO 170° | 10 90° TO 170° |

| PS | 1 (50mm) | 2 (52mm) | 3 (52mm) | 4 (56mm) | 5 (58mm) | 6 (60mm) | 7 (62mm) | 8 (64mm) | 9 (88mm) | 10 (68mm) | 11 (70mm) | 12 (74mm) |
|---|---|---|---|---|---|---|---|---|---|---|---|---|
| A | 1-2 / AB | | 3-5 / AB | | | | | | | | | |
| B | 1-2 / AB | | 3-5 / AB | | | | | | | | | |
| C | 1-2 / CD | | 3-4 / CD | | | 6-9 / CD | | | | | | |
| D | 1-2 / CD | | 3-4 / CD | | | 6-9 / CD | | | | | | |
| E | | | 3-5 / EF | | | 6-9 / EF | | | | 10-11 / EF | | |
| F | | | 3-5 / EF | | | 6-9 / EF | | | | 10-11 / EF | | |
| G | | | | | | 6-9 / GH | | | | 10-12 / GH | | |
| H | | | | | | 6-9 / GH | | | | 10-12 / GH | | |
| I | | | | | | | | | | 10-12 / J | | |

FIG. 10

POSTERIOR STABILIZED PROSTHESIS SYSTEM

CLAIM OF PRIORITY

This application is a continuation of U.S. patent application Ser. No. 16/389,381, filed on Apr. 19, 2019, which claims the benefit of U.S. Provisional Patent Application Ser. No. 62/664,500, filed on Apr. 30, 2018, the benefit of priority of each of which is claimed hereby, and each of which is incorporated by reference herein in its entirety.

FIELD

The present subject matter relates to orthopedic procedures and, more particularly, to prostheses, systems and methods used in knee arthroplasties.

BACKGROUND

Orthopedic procedures and prostheses are commonly utilized to repair and/or replace damaged bone and tissue in the human body. For example, a knee arthroplasty can be used to restore natural knee function by repairing damaged or diseased articular surfaces of the femur and/or tibia. An incision is made into the knee joint to expose the bones comprising the joint. Cut guides are used to guide the removal of the articular surfaces that are to be replaced. Prostheses are used to replicate the articular surfaces. Knee prostheses can include a femoral prosthesis implanted on the distal end of the femur, which articulates with a tibial bearing component and a tibial component implanted on the proximal end of a tibia to replicate the function of a healthy natural knee. Various types of procedures are known including a total knee arthroplasty (TKA), where all of the articulating compartments of the joint are repaired with prosthetic components.

OVERVIEW

This disclosure pertains generally to prostheses and systems for knee arthroplasty. The present inventors have recognized, among other things, improvements to femoral prostheses (sometimes called femoral prostheses) and tibial bearing components (sometimes called tibial bearing prostheses, tibial bearings, bearings, poly or bearing components). In particular, the present inventors have focused on posterior-stabilized (PS) prostheses, which include a spine on the tibial bearing component and a cam on the femoral prosthesis that are configured to interact together when the femoral prosthesis is in flexion to provide further stability to the knee joint. PS prostheses are typically utilized in instances where one or more of the cruciate ligaments (e.g, ACL and PCL) of the knee joint have suffered degeneration and must be eliminated. PS prostheses have particular design considerations and kinematics, which differ from other types of knee prostheses such as ultra-congruent (UC) and cruciate-retaining (CR) prostheses, for example.

Considering criteria specific to PS prostheses, the present inventors have designed femoral prostheses and tibial bearing components that allow for greater joint stability, improved kinematics during flexion of the knee joint, and increased compatibility with other known prosthesis designs. Thus, with regard to the femoral prostheses disclosed the present inventors propose an example where medial and lateral condyles are shaped to articulate with a tibial articular surface of a tibial bearing component through a range of motion. In a sagittal plane, the medial and lateral condyles can define medial and lateral multi-radius curves, respectively. The medial multi-radius curve can have a single common radius swept through a first angular extent to define a single arc length that extends from between substantially −20 degrees flexion to substantially 90 degrees flexion, inclusive. A posterior portion (shown and described subsequently) of the medial and lateral condyles can have a thickness of 9 mm. In one example, the medial multi-radius curve can have a second radius swept through a second angular extent to define a second arc length that extends from between substantially 90 degrees flexion to beyond 100 degrees flexion. The medial and lateral condyles can be symmetrically shaped such that lateral condyle can have a lateral multi-radius curve of a same shape as the medial multi-radius curve. Thus, the lateral multi-radius curve can have the single common radius swept through the first angular extent to define the single arc length that extends from between substantially −20 degrees flexion to substantially 90 degrees flexion, inclusive.

According to disclosed examples, in combination the femoral prosthesis and the tibial bearing component can be configured such that an area of contact between the medial condyle and the tibial articular surface includes a medial dwell point of the tibial articular surface when the femoral prosthesis is in full extension. The femoral prosthesis and the tibial bearing component can be configured such that the area of contact between the medial condyle and the tibial articular surface does not shift during the range of motion between zero degrees flexion and substantially 100 degrees flexion and includes the medial dwell point during the range of motion between zero degrees flexion and substantially 100 degrees flexion. A spine of the tibial bearing component and a cam of the femoral prosthesis can make initial contact when the range of motion reaches substantially 100 degrees flexion. A medial compartment of the tibial bearing component can be configured to have between about a 1.05:1 congruence ratio and about a 1.5:1 congruence ratio with the medial condyle through the first angular extent, the congruence ratio can comprise a ratio of the similarity between a sagittal radius of the medial compartment and the single common radius of the medial condyle.

Regarding the tibial bearing component, the medial compartment can be configured to have the medial dwell point a distance between about 52% and about 60% of a total anterior-posterior extent of the tibial bearing component as measured from an anterior most point to a posterior most point of the tibial bearing component. The lateral compartment can be configured to have a lateral dwell point a distance between about 59% and about 62% of a total anterior-posterior extent of the tibial bearing component as measured from an anterior most point to a posterior most point of the tibial bearing component.

Additionally, the present inventors have designed a family of tibial bearing components that can have at least eleven different stock sizes so as to achieve more compatible combinations when used with a family of tibia prostheses that can have at least nine different stock sizes and a family of femoral prostheses that can have at least twelve different stock sizes. Due to the number of components and the designed compatibility between various sizes in the respective families, thirty three combinations of the at least eleven different stock sizes of the family of tibial bearing components can be compatible for operable use with the at least twelve different stock sizes of the family of femoral prostheses.

To further illustrate the apparatuses and systems disclosed herein, the following non-limiting examples are provided:

Example 1 is a posterior-stabilized femoral prosthesis for a knee arthroplasty. The femoral prosthesis can include medial and lateral condyles, a femoral cam and a recess. The medial and lateral condyles can be shaped to articulate with a tibial articular surface of a tibial bearing component through a range of motion, in which full extension corresponds to zero degrees flexion of a knee joint and positive flexion corresponds to greater than zero degrees flexion of the knee joint. In a sagittal plane, the medial and lateral condyles can define medial and lateral multi-radius curves, respectively. The medial multi-radius curve can have a single common radius swept through a first angular extent to define a single arc length that extends from between substantially −20 degrees flexion to substantially 90 degrees flexion, inclusive. The femoral cam and the recess can be positioned between the medial and lateral condyles. The femoral cam can be positioned posterior of the recess.

In Example 2, the femoral prosthesis of Example 1, wherein an area of contact can be between the medial condyle and the tibial articular surface can include a medial dwell point of the tibial articular surface when the femoral prosthesis is in full extension.

In Example 3, the femoral prosthesis of Example 2, wherein the area of contact between the medial condyle and the tibial articular surface may not shift position during the range of motion between zero degrees flexion and substantially 100 degrees flexion, and wherein the area of contact can include the medial dwell point during the range of motion between zero degrees flexion and substantially 100 degrees flexion.

In Example 4, the femoral prosthesis of any one or any combination of Examples 1-3, wherein a posterior portion of the medial and lateral condyles can have a thickness of 9 mm.

In Example 5, the femoral prosthesis of any one or any combination of Examples 1-4, further comprising the tibial bearing component defining the tibial articular surface, the tibial articular surface can optionally include: a medial compartment and a lateral compartment configured for articulation with the medial condyle and the lateral condyle of the femoral prosthesis, respectively; and a spine extending proximally from the articular surface and configured to be received in the recess at 0 degrees flexion, the spine spaced posteriorly from an anterior edge of the tibial bearing periphery, the spine disposed between the medial and lateral compartments; wherein the spine and cam make initial contact when the range of motion reaches substantially 100 degrees flexion.

In Example 6, the femoral prosthesis of Example 5, wherein the medial compartment can be configured to have the medial dwell point a distance between about 52% and about 60% of a total anterior-posterior extent of the tibial bearing component as measured from an anterior most point to a posterior most point of the tibial bearing component.

In Example 7, the femoral prosthesis of Example 5, wherein the lateral compartment can be configured to have a lateral dwell point a distance between about 59% and about 62% of a total anterior-posterior extent of the tibial bearing component as measured from an anterior most point to a posterior most point of the tibial bearing component.

In Example 8, the femoral prosthesis of any one or any combination of Example 5-7, wherein the medial compartment can be configured to have between about a 1.05:1 congruence ratio and about a 1.5:1 congruence ratio with the medial condyle through the first angular extent, the congruence ratio comprising a ratio of the similarity between a sagittal radius of the medial compartment and a sagittal radius of the medial condyle.

In Example 9, a system of posterior-stabilized knee prostheses for a knee arthroplasty, the system can optionally comprise: a tibial bearing component having a tibial articular surface with a medial compartment and a lateral compartment, wherein the tibial bearing component has a spine extending proximally from the tibial articular surface and positioned between the medial and lateral compartments, and wherein the medial compartment has a medial dwell point; a femoral prosthesis having a cam and medial and lateral condyles spaced to either side of the cam, wherein the medial condyle is configured for articulation with the medial compartment and lateral condyle is configured for articulation with the lateral compartment, and wherein femoral prosthesis is configured to articulate through a range of motion relative to the tibial bearing component, such range of motion includes a full extension that corresponds to zero degrees flexion of a knee joint and positive flexion that corresponds to greater than zero degrees flexion of the knee joint, and wherein an area of contact between the medial condyle and the medial compartment does not shift position during the range of motion between zero degrees flexion and substantially 100 degrees flexion and the area of contact includes the medial dwell point during the range of motion between zero degrees flexion and substantially 100 degrees flexion.

In Example 10, the system of Example 9, wherein in a sagittal plane the medial and lateral condyles can define medial and lateral multi-radius curves, respectively, and wherein the medial multi-radius curve can have a single common radius swept through a first angular extent to define a single arc length that extends from between substantially −20 degrees flexion to substantially 90 degrees flexion, inclusive.

In Example 11, the system of any one or any combination of Examples 9-10, wherein a posterior portion of the medial and lateral condyles can have a thickness of 9 mm.

In Example 12, the system of any one or any combination of Examples 9-11, wherein the spine and cam can both be configured to make initial contact when the range of motion reaches substantially 100 degrees flexion.

In Example 13, the system of any one or any combination of Examples 9-12, wherein the medial compartment can be configured to have the medial dwell point a distance between about 52% and about 60% of a total anterior-posterior extent of the tibial bearing component as measured from an anterior most point to a posterior most point of the tibial bearing component.

In Example 14, the system of any one or any combination of Examples 9-12, wherein the lateral compartment can be configured to have a lateral dwell point a distance between about 59% and about 62% of a total anterior-posterior extent of the tibial bearing component as measured from an anterior most point to a posterior most point of the tibial bearing component.

In Example 15, the system of any one or any combination of Examples 9-14, wherein the medial compartment can be configured to have between about a 1.05:1 congruence ratio and about a 1.5:1 congruence ratio with the medial condyle through the first angular extent, the congruence ratio comprising a ratio of the similarity between a sagittal radius of the medial compartment and a sagittal radius of the medial condyle.

In Example 16, a system of posterior-stabilized knee prostheses for a knee arthroplasty, the system can optionally comprise: a tibial bearing component having a tibial articular surface with a medial compartment and a lateral compartment, wherein the tibial bearing component has a spine extending proximally from the tibial articular surface and positioned between the medial and lateral compartments, and wherein the medial compartment has a medial dwell point; a femoral prosthesis having a cam and medial and lateral condyles spaced to either side of the cam, wherein the medial condyle is configured for articulation with the medial compartment and lateral condyle is configured for articulation with the lateral compartment, and wherein femoral prosthesis is configured to articulate through a range of motion relative to the tibial bearing component, such range of motion includes a full extension that corresponds to zero degrees flexion of a knee joint and positive flexion that corresponds to greater than zero degrees flexion of the knee joint, wherein an area of contact between the medial condyle and the medial compartment includes the medial dwell point when the femoral prosthesis is in full extension, and wherein the spine and cam are both configured to make initial contact when the range of motion reaches substantially 100 degrees flexion.

In Example 17, the system of Example 16, wherein the area of contact between the medial condyle and the tibial articular surface may not shift during the range of motion between zero degrees flexion and substantially 100 degrees flexion and can include the medial dwell point during the range of motion between zero degrees flexion and substantially 100 degrees flexion.

In Example 18, the system of any one or any combination of Examples 16-17, wherein in a sagittal plane the medial and lateral condyles can define medial and lateral multi-radius curves, respectively, and wherein the medial multi-radius curve can have a single common radius swept through a first angular extent to define a single arc length that extends from between substantially −20 degrees flexion to substantially 90 degrees flexion, inclusive.

In Example 19, the system of any one or any combination of Examples 16-18, wherein the medial compartment can be configured to have the medial dwell point a distance between about 52% and about 60% of a total anterior-posterior extent of the tibial bearing component as measured from an anterior most point to a posterior most point of the tibial bearing component.

In Example 20, the system of any one or any combination of Examples 16-19, wherein a posterior portion of the medial and lateral condyles can have a thickness of 9 mm.

In Example 21, the apparatuses or systems of any one or any combination of Examples 1-20 can optionally be configured such that all elements or options recited are available to use or select from.

These and other examples and features of the present apparatuses and systems will be set forth in part in the following Detailed Description. This Overview is intended to provide non-limiting examples of the present subject matter—it is not intended to provide an exclusive or exhaustive explanation. The Detailed Description below is included to provide further information about the present apparatuses and systems.

BRIEF DESCRIPTION OF THE DRAWINGS

In the drawings, which are not necessarily drawn to scale, like numerals can describe similar components in different views. Like numerals having different letter suffixes can represent different instances of similar components. The drawings illustrate generally, by way of example, but not by way of limitation, various examples discussed in the present document.

FIG. 10 shows a sizing chart for a family of tibial bearing components relative to a family of femoral prostheses, tibial prostheses and tibial bearing components in accordance with an example of the present application.

DETAILED DESCRIPTION

The present application relates femoral prostheses, tibial bearing components and systems including such prostheses and components.

In a TKA, both of the medial and lateral condyles of the femur can be resected. Similarly, the tibia can be resected to remove the medial articular surface and the lateral articular surface using a cutting apparatus. Other portions of the knee, e.g., the intercondylar eminence, can also be removed. Depending on the type of TKA, features such as the ligaments can be spared or can also be removed. As discussed above, in a PS TKA, the ligaments such as the posterior cruciate ligament PCL are removed. Prostheses can be implanted on the femur and the tibia and a bearing component can be placed between the femoral prosthesis and the tibial prosthesis to provide for the replaced articular surfaces.

Figure 1:
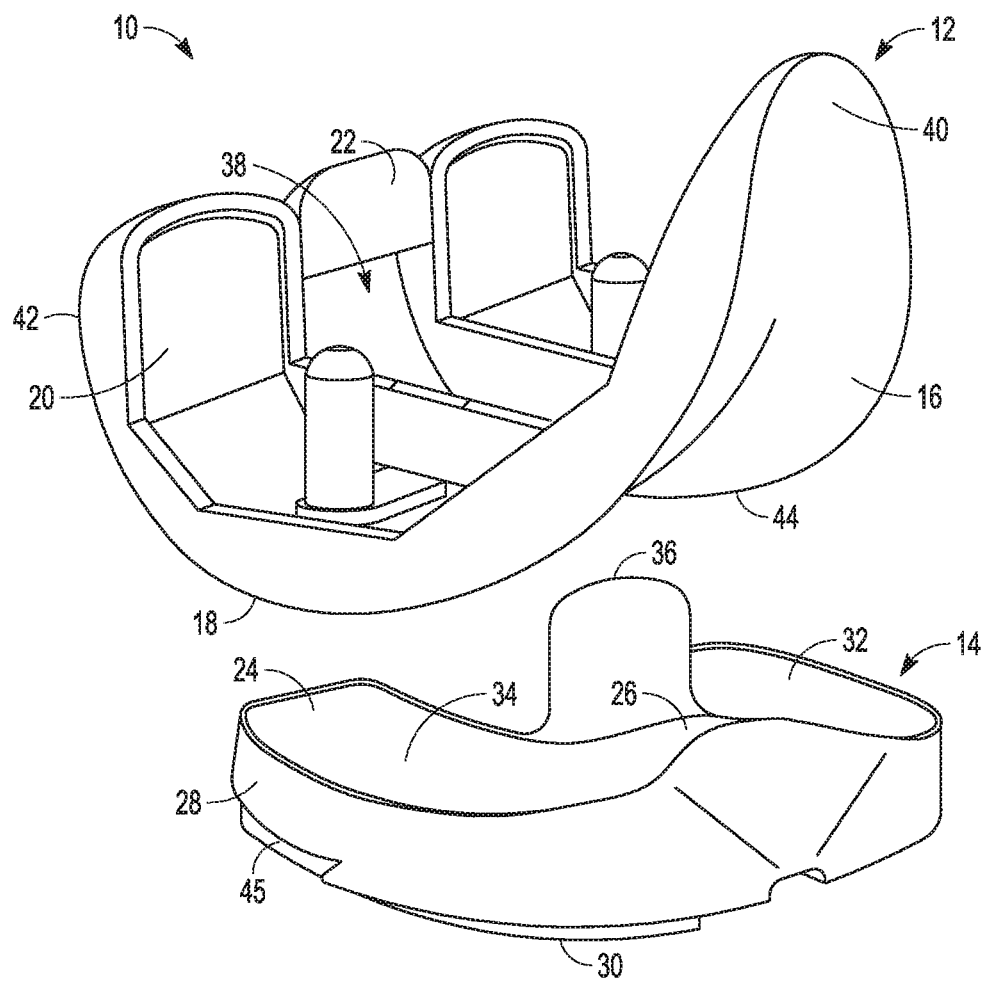
FIG. 1 is an exploded view of a femoral prosthesis and a tibial bearing component in accordance with an example of the present application.

FIG. 1 shows a system 10 that includes a femoral prosthesis 12 and a tibial bearing component 14. The femoral prosthesis 12 can include a lateral condyle 16, a medial condyle 18, bone interfacing surfaces 20, and a cam 22. The tibial bearing component 14 can include an articular surface 24, an intercondylar region 26, a periphery 28 and a distal surface 30. The articular surface 24 can include a lateral compartment 32 and a medial compartment 34. The intercondylar region 26 can include a spine 36.

The femoral prosthesis 12 can be implanted on a respected femur (not shown) via the bone interfacing surfaces 20. The tibial bearing component 14 can attach to a tibial prosthesis (not shown) that is implanted on a resected tibia (not shown). The femoral prosthesis 12 and the tibial bearing component 14 are configured to articulate together through a range of motion for the femoral prosthesis 12. This range of motion can include knee joint flexion and extension as will be illustrated and described subsequently.

The lateral condyle 16 is spaced from the medial condyle 18 in a medial-lateral direction by a sulcus space and in some portions of the femoral prosthesis 12 by a recess 38. The femoral prosthesis 12 can have an anterior end portion 40 and a posterior end portion 42. The cam 22 can be disposed at the posterior end portion 42 proximal of the recess 38. The cam 22 can extend between the lateral condyle 16 and the medial condyle 18.

Figure 2:
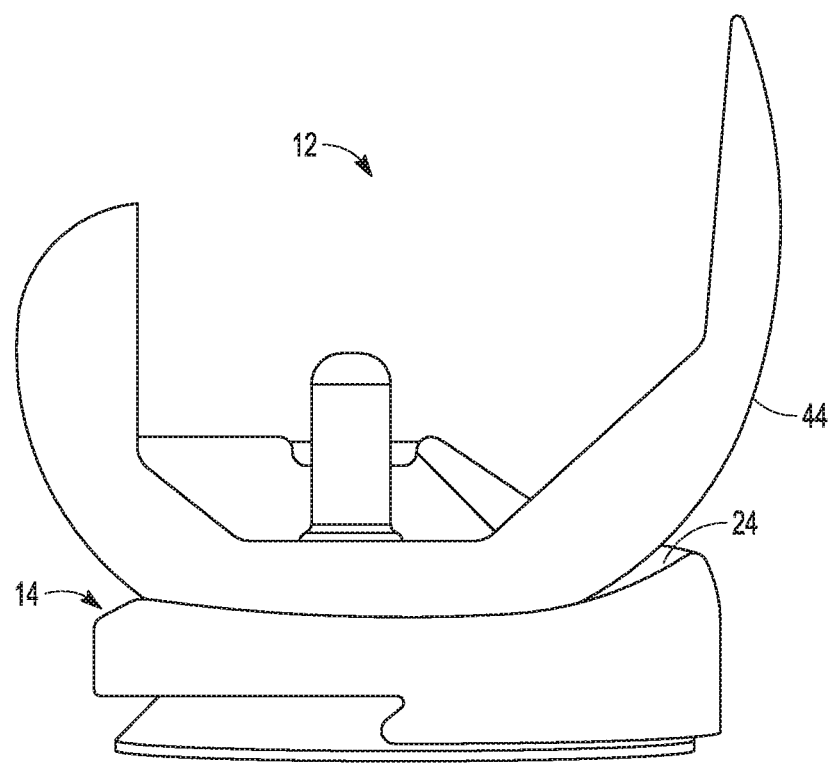
FIG. 2 is a perspective view of the femoral prostheses assembled with the tibial bearing component with the knee joint in full extension in accordance with an example of the present application.

The lateral condyle 16 can be arcuate in shape having a radius of curvature along an articular surface 44 as will be illustrated and discussed subsequently. The lateral condyle 16 can be configured to be received by the lateral compartment 32 for articulation therewith when the femoral prosthesis 12 is assembled atop the tibial bearing component 14 such as shown in FIG. 2. Similarly, the medial condyle 18 can be arcuate in shape along the articular surface 44 having a radius of curvature as will be illustrated and discussed subsequently. The medial condyle 18 can be configured to be received by the medial compartment 34 for articulation therewith when the femoral prosthesis 12 is assembled atop the tibial bearing component 14 such as shown in FIG. 2.

According to the example of FIG. 1, the lateral condyle 16 can be symmetrically shaped relative to the medial condyle 18. This results in the lateral condyle 16 and medial condyle 18 sharing the same radius of curvature resulting in each having a same shape for a multi-radius curve as shown and described subsequently.

For the tibial bearing component 14, the articular surface 24 comprises a proximal surface for the tibial bearing component 14 and can be configured to interface with the lateral and medial condyles 16 and 18. The articular surface 24 and the intercondylar region 26 can be opposed to and spaced from the distal surface 30 by the periphery 28. The periphery 28 and/or the distal surface 30 can include features 45 for attachment to the tibial prosthesis. The features 45 can be shaped to mate with corresponding features of a sidewall of a tibial tray (now shown) such as to create an interference fit, for example.

As discussed above, the articular surface 24 can include the lateral compartment 32 and the medial compartment 34. The lateral and medial compartments 32 and 34 can be dish shaped with a curvature in a proximal-distal and the medial-lateral directions. The lateral compartment 32 can be spaced in the medial-lateral direction from the medial compartment 34.

Figure 2A:
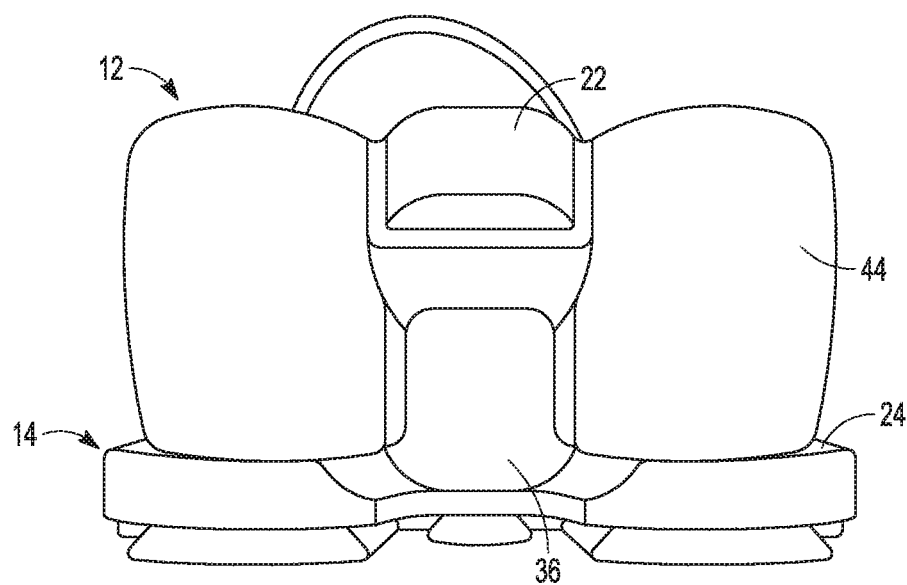
FIG. 2A is a plan view of posterior portions of the femoral prosthesis and the tibial bearing component of FIG. 2.

The intercondylar region 26 can be positioned between the lateral and medial compartments 32 and 34. The intercondylar region 26 can comprise a raised prominence relative to the lateral and medial compartments 32 and 34. The spine 36 can be part of the intercondylar region 26 positioned between the lateral and medial compartments 32 and 34. The spine 36 can also be spaced posteriorly from an anterior edge of the periphery 28. The spine 36 can comprise a projection extending generally proximally from the intercondylar region 26. The spine 36 can be canted anterior-to-posterior as will be subsequently shown. The spine 36 can configured to be received in the recess 38 at 0 degrees flexion as shown in FIGS. 2A and 2B.

Further details relating to aspects of the construct of the femoral prosthesis 12 and tibial bearing component 14 can found in U.S. Pat. Nos. 8,858,643, 9,072,607, 8,690,954, 8,764,838, 8,932,365 and United States Application Publication No. 2012/0323336, the disclosures of which are incorporated by reference in their entirety.

According to one example, the femoral component 12 can be designed to be compatible with other commercially available tibial bearing components such as those of the Zimmer Biomet Persona® knee system manufactured by Zimmer Biomet Holding, Inc. of Warsaw, Ind. Similarly, according to one example, the tibial bearing component 14 can be designed to be compatible with other commercially available femoral prostheses such as those of the Zimmer Biomet Persona® knee system.

Figure 2B:
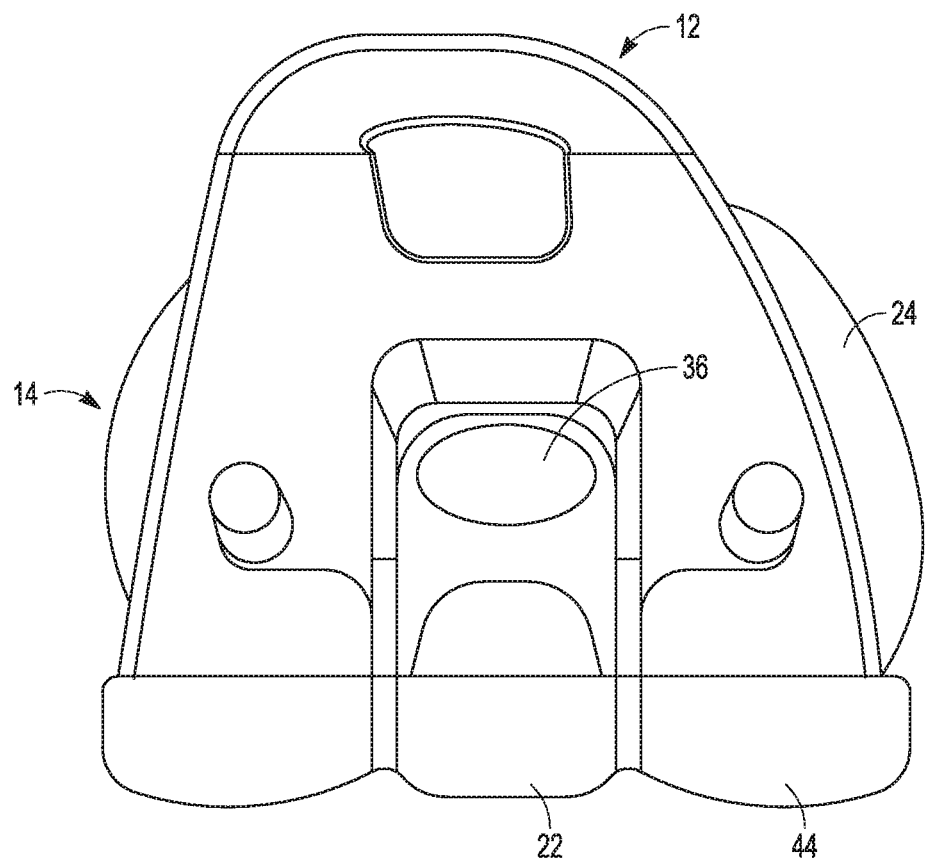
FIG. 2B is a plan view from a proximal position of the femoral prosthesis and the tibial bearing component of FIG. 2.

FIGS. 2 to 2B show the femoral prosthesis 12 assembled atop the tibial bearing component 14. In FIGS. 2 to 2B, the knee joint is illustrated in full extension (corresponding to 0 degrees flexion).

As shown in the example of FIGS. 2-2B, the tibial bearing component 14 is compatible with and configured for operable use to articulate with the femoral prosthesis 12. In particular, the articular surface 24 of the tibial bearing component 14 can be configured to receive the articular surface 44 of the femoral prosthesis 12 thereon and can be configured to allow for articular movement of the femoral prosthesis 12 relative thereto through the range of motion in a manner that simulates the kinematics of a natural knee (e.g., allow for rollback of the femoral prosthesis 12 in flexion including anterior-posterior translation, engagement of the spine 36 with the cam 22 (features shown in FIGS. 2A and 2B), etc.)

Figure 3A:
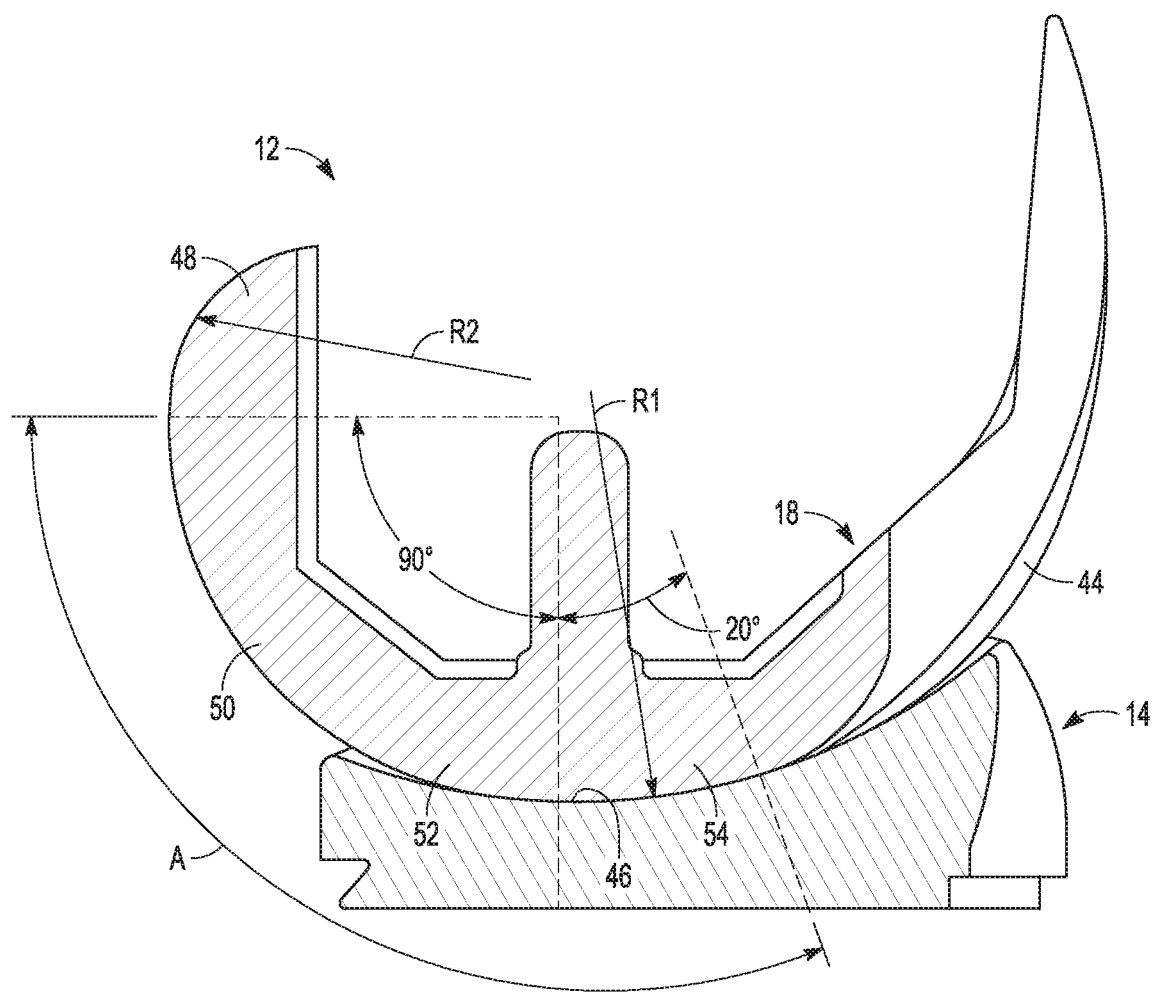
FIG. 3A is a cross-sectional view of the femoral prosthesis and the tibial bearing component of FIG. 2 taken in a sagittal plane along a medial multi-radius curve of the femoral prosthesis in accordance with an example of the present application.

FIG. 3A shows a sagittal cross-section of the tibial bearing component 14 and the femoral prosthesis 12 with the cross-section taken through the medial condyle 18. In FIG. 3A, the medial condyle 18 defines a medial multi-radius curve 46 that is part of the articular surface 44.

As shown in FIG. 3A, the medial condyle 18 can have a high flex portion 48, a posterior portion 50, an extension to mid-flexion portion 52, and a part of an anterior region 54. As shown in the example of FIG. 3, the posterior portion 50 and the extension to mid-flexion portion 52 can share a single common radius R1. Indeed, in the example of FIG. 3A, the posterior portion 50, the extension to mid-flexion portion 52, and the part of the anterior region 54 can share the single common radius R1.

In FIG. 3A, the posterior portion 50 extends to 90 degrees flexion, inclusive. The high flex portion 48 extends between substantially 90 degrees flexion to 170 degrees. The extension to mid-flexion portion 52 can extend from the posterior portion 50 to 0 degrees flexion (0 degrees flexion comprising full extension). The part of the anterior region 54 can extend from substantially 0 degrees flexion to −20 degrees flexion, inclusive, for example.

According to the example shown, the medial multi-radius curve 46 can have the single common radius R1 swept through a first angular extent to define a single arc length A that extends from between substantially −20 degrees flexion to substantially 90 degrees flexion, inclusive. The single arc length A includes the posterior portion 50, the extension to mid-flexion portion 52 and the part of the anterior region 54. Thus, the medial multi-radius curve 46 can have the single common radius R1 swept through a first portion of the first angular extent to define a first part the single arc length A that extends from between substantially 0 degrees flexion to substantially 90 degrees flexion. Additionally, the medial multi-radius curve 46 can have the single common radius R1 swept through a second portion of the first angular extent to define a second part the single arc length A that extends from between substantially −20 degrees flexion to substantially 0 degrees flexion.

In the example of FIG. 3A, the high flex portion 48 can have a second radius R2 that differs from that of the single common radius R1. In particular, the second radius R2 can be smaller than the single common radius R1. Such a configuration can avoid or reduce the likelihood of a kinematic conflict between the cam 22 (features shown in FIGS. 2A and 2B) and the spine 36. This can allow for a transition region in the high flex portion 48 of substantially 10 degrees of flexion (as measured from the end of the posterior portion 50 at substantially 90 degrees) as the spine 36 and the cam can be configured to make initial contact with the range of motion reaches substantially 100 degrees flexion with the tibial bearing component 14 positioned at a 5 degree anterior-to-posterior slope. If the tibial bearing component 14 was positioned at another angle (e.g., 3 degrees of slope anterior-to-posterior) as can occur in other examples, the cam and spine 36 would make initial contact at a different degree of flexion. For example, with the tibial bearing component 14 positioned at 3 degrees of slope anterior-to-posterior, the cam and spine 36 would make initial contact at an angle of flexion less than 100 degrees.

Figure 3B:
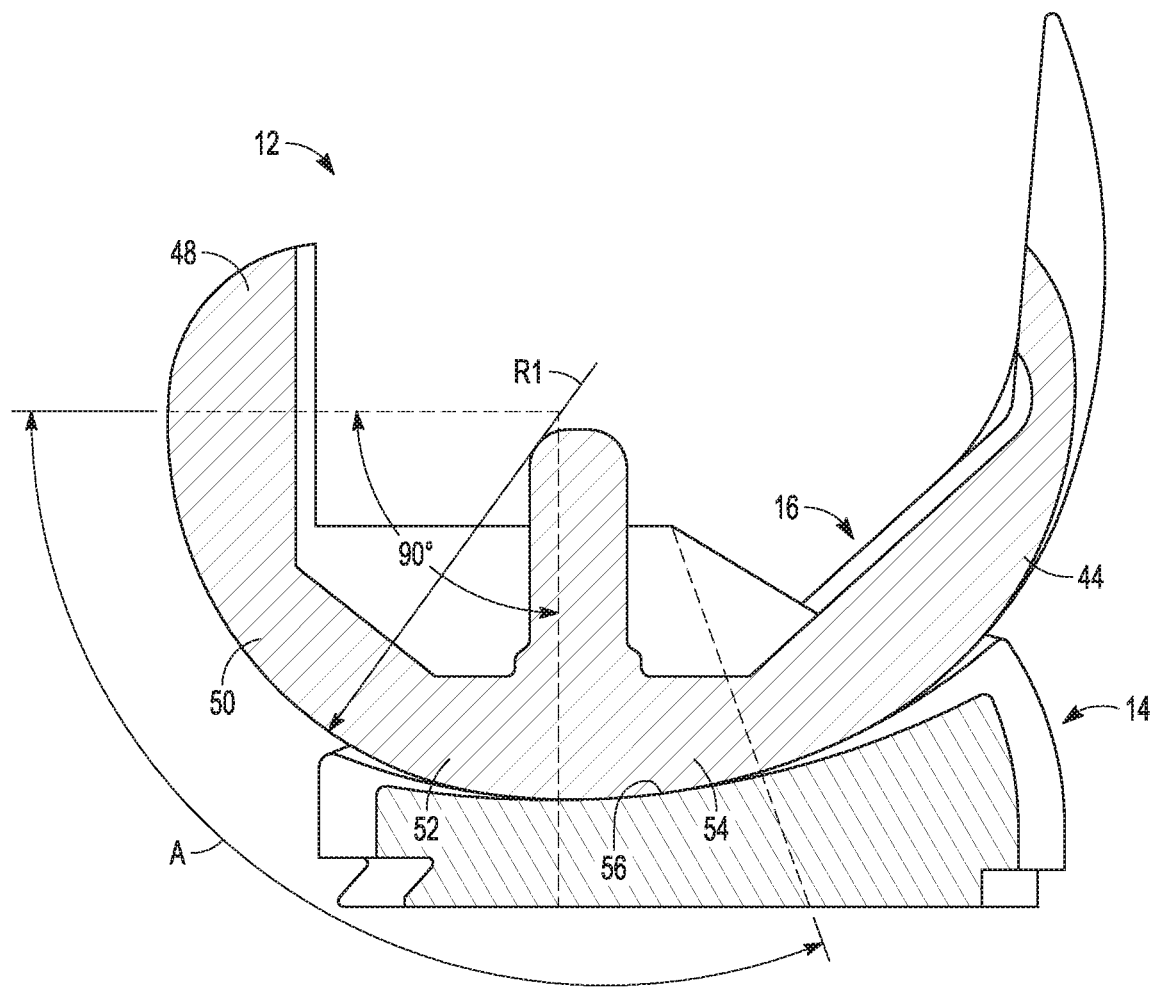
FIG. 3B is a cross-sectional view of the femoral prosthesis and the tibial bearing component of FIG. 2 taken in the sagittal plane along a lateral multi-radius curve of the femoral prosthesis in accordance with an example of the present application.

FIG. 3B shows a sagittal cross-section of the femoral prosthesis 12 with the cross-section taken through the lateral condyle 16. In FIG. 3B, the lateral condyle 16 defines a lateral multi-radius curve 56 that is part of the articular surface 44. As discussed previously the lateral condyle 16 can by symmetrically shaped with respect to the medial condyle 18. Thus, the lateral condyle 16 can have a same shape as the medial condyle 18.

As a result of the symmetry in geometry between the medial condyle 18 and the lateral condyle 16, the lateral multi-radius curve 56 can have a same shape as the medial multi-radius curve 46. The medial condyle 16 can have the high flex portion 48, the posterior portion 50, the extension to mid-flexion portion 52, and the part of the anterior region 54, as previously discussed. As shown in the example of FIG. 3B, the posterior portion 50 and the extension to mid-flexion portion 52 can share the single common radius R1. Indeed, in the example of FIG. 3B, the posterior portion 50, the extension to mid-flexion portion 52, and the part of the anterior region 54 can share the single common radius R1.

In FIG. 3B, the posterior portion 50 extends to 90 degrees flexion, inclusive. The high flex portion 48 extends between substantially 90 degrees flexion to greater degrees of flexion (e.g., 170 degrees). The extension to mid-flexion portion 52 can extend from the posterior portion 50 to 0 degrees flexion (0 degrees flexion comprising full extension). The part of the anterior region 54 can extend from substantially 0 degrees flexion to −20 degrees flexion, inclusive, for example.

According to the example shown, the lateral multi-radius curve 56 can have the single common radius R1 swept through a first angular extent to define a single arc length A that extends from between substantially −20 degrees flexion to substantially 90 degrees flexion, inclusive. The single arc length A includes the posterior portion 50, the extension to mid-flexion portion 52 and the part of the anterior region 54. Thus, the lateral multi-radius curve 56 can have the single common radius R1 swept through a first portion of the first angular extent to define a first part the single arc length A that extends from between substantially 0 degrees flexion to substantially 90 degrees flexion. Additionally, the lateral multi-radius curve 56 can have the single common radius R1 swept through a second portion of the first angular extent to define a second part the single arc length A that extends from between substantially −20 degrees flexion to substantially 0 degrees flexion.

Figure 4:
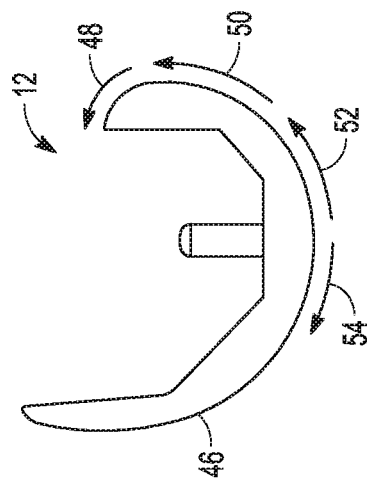
FIG. 4 is a table comparing radii of curvatures for various portions of the medial multi-radius curve of the femoral prosthesis as presently disclosed with other commercially available femoral prostheses in accordance with an example of the present application.

FIG. 4 shows a table comparing the sagittal radii of the medial multi-radius curve 46 (FIG. 3A) of the present femoral prostheses 12 with the medial multi-radius curve 46 of various commercially available femoral prostheses of comparable size for the high flex portion 48, the posterior portion 50, the extension to mid-flexion portion 52, and the part of the anterior region 54, as previously discussed. In the table of FIG. 4, the commercially available femoral prostheses are labeled "Comp. A" to "Comp. F", while the femoral prosthesis 12 is labeled as "Comp. 12".

The table of FIG. 4 shows the single common radius R1 (illustrated in FIGS. 3A and 3B) is shared by the posterior portion 50, the extension to mid-flexion portion 52, and the part of the anterior region 54 for the medial multi-radius curve as previously described. As shown in the table, none of the commercially available femoral prostheses exhibit similar geometry of the medial multi-radius curve. Indeed, all the commercially available femoral prostheses include three separate and distinct radii for the high flex portion 48, the posterior portion 50, the extension to mid-flexion portion 52, and the part of the anterior region 54.

Figure 5:
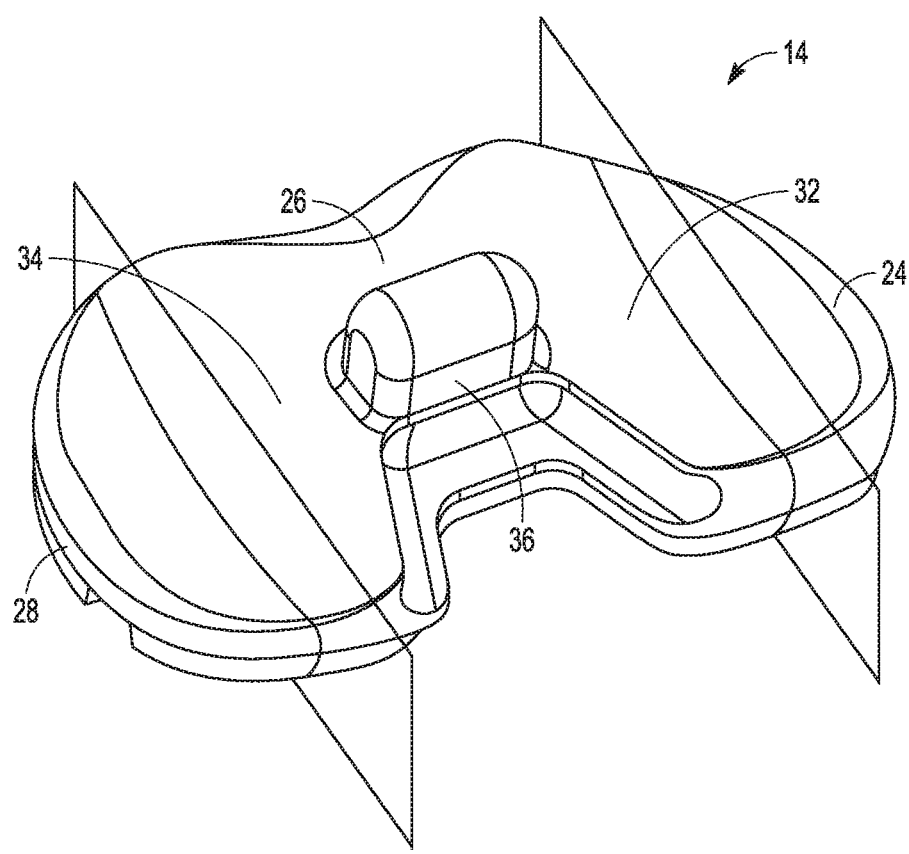
FIG. 5 is a perspective view of the tibial bearing component according to one example of the present application.
Figure 5A:
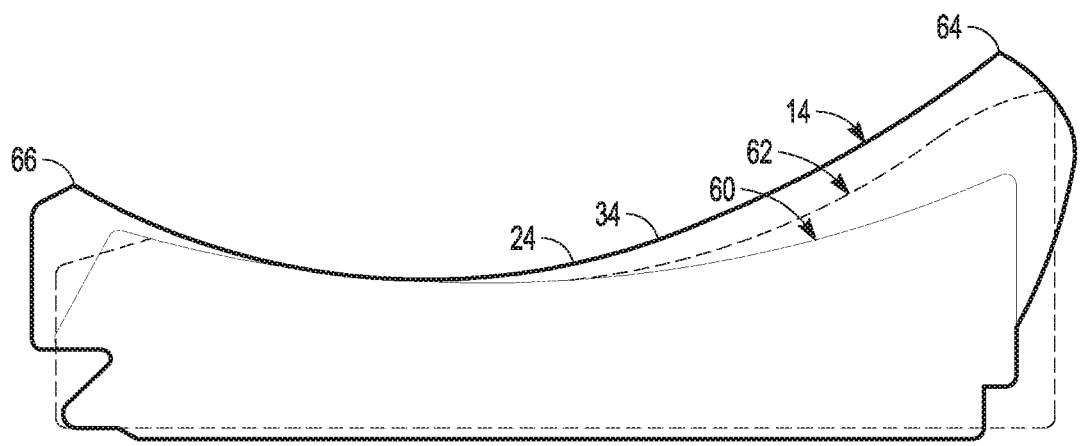
FIG. 5A is a view in a sagittal plane extending through the medial compartment showing an outline of shape of the articular surface and other portions for various tibial bearing components including the tibial bearing component of FIGS. 2 and 5 in comparison with two commercially available tibial bearing components of similar size according to one example of the present application.
Figure 5B:
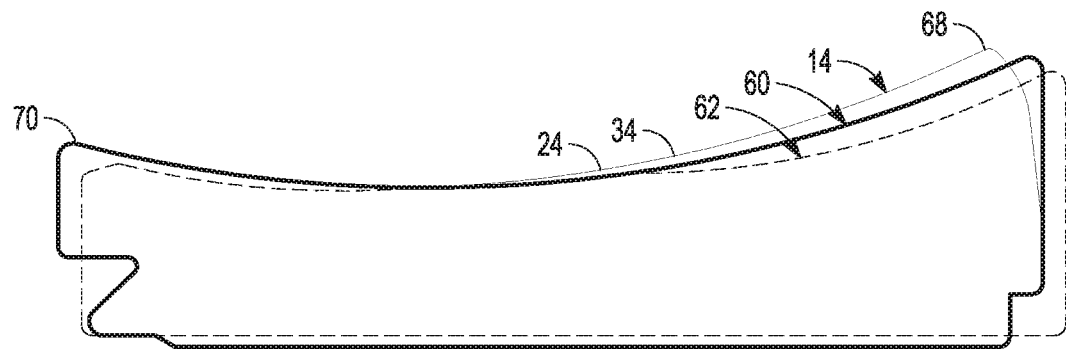
FIG. 5B is a view in a sagittal plane extending through the lateral compartment showing an outline of shape of the articular surface and other portions for various tibial bearing components including the tibial bearing component of FIGS. 2 and 5 in comparison with two commercially available tibial bearing components of similar size according to one example of the present application.
Figure 5C:
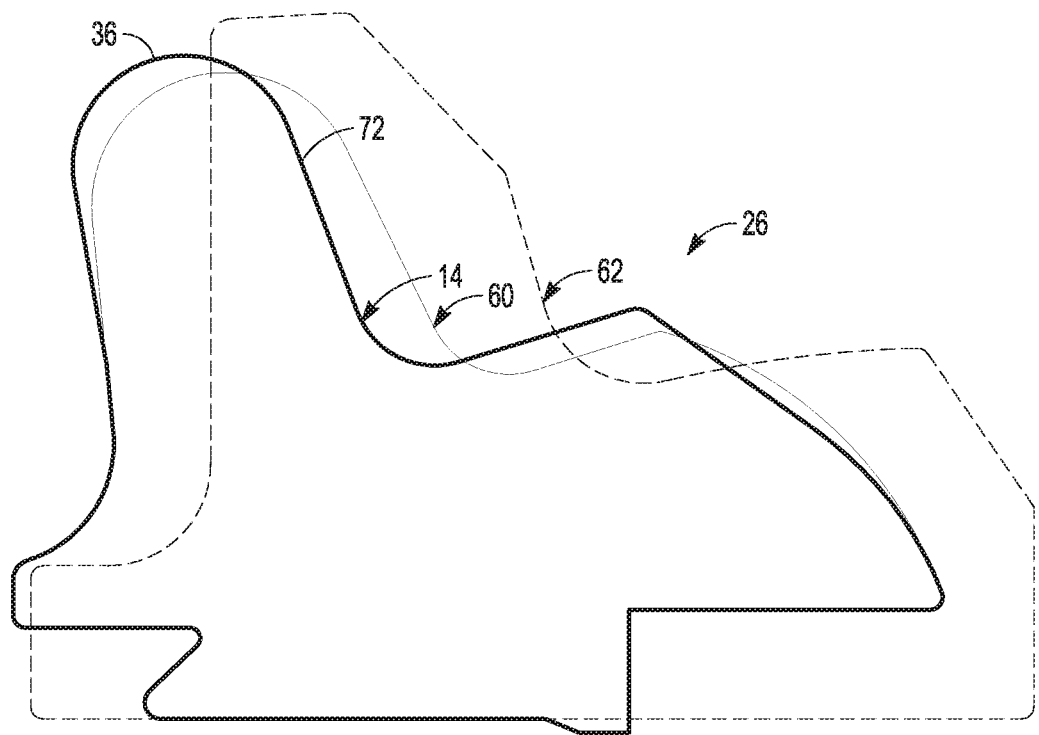
FIG. 5C is a view in a sagittal plane extending through the spine and intercondylar space showing an outline of shape of the spine and intercondylar space for various tibial bearing components including the tibial bearing component of FIGS. 2 and 5 in comparison with two commercially available tibial bearing components of similar size according to one example of the present application.

FIGS. 5 to 5C show aspects of the construction of the tibial bearing component 14 according to one example. FIG. 5 shows the tibial bearing component 14 as previously described including include the articular surface 24, the intercondylar region 26, the periphery 28 and the distal surface 30 as previously described in reference to FIG. 1. The articular surface 24 can include the lateral compartment 32 and the medial compartment 34. The intercondylar region 26 can include the spine 36.

Unlike the lateral and medial condyles 16 and 18, the lateral compartment 32 and the medial compartment 34 can have a different shape relative to one another as illustrated in the example of FIGS. 5A and 5B.

FIG. 5A shows a sagittal cross-section through the medial compartment 34 of the tibial bearing component 14. FIG. 5A shows a comparison of the articular surface 24 in the medial compartment 34 overlaid with the corresponding articular surfaces in the medial compartments of two commercially available tibial bearing components (indicated as component 60 and component 62). Component 60 can comprise a cruciate retaining tibial bearing component of the Persona@ knee system, for example.

As shown in FIG. 5A, the tibial bearing component 14 in the medial compartment 34 can have an anterior lip 64 at the transition between an anterior portion of the articular surface 24 and the periphery 28, and similarly, can have a posterior lip 66 at the transition between a posterior portion of the articular surface 24 and the periphery 28. As shown in FIG. 5A, a height of the anterior lip 64 and the posterior lip 66 exceeds those of components 60 and 62. This configuration gives the articular surface 24 a steeper inclination as compared to components 60 and 62 as the articular surface 24 has a similar geometry to those of components 60 and 62 in a mid-portion.

FIG. 5B shows a sagittal cross-section through the lateral compartment 32 of the tibial bearing component 14. FIG. 5B shows a comparison of the articular surface 24 in the lateral compartment 32 overlaid with the corresponding articular surfaces in the lateral compartments of component 60 and component 62. For the articular surface 24 in the lateral compartment 32, this configuration can be very similar to that of component 60, for example. The articular surface 24 in the lateral compartment 32 can have an anterior lip 68 that is slightly greater in height than that of components 60 and 62. However, a height of a posterior lip 70 height can be comparable to that of component 60.

FIG. 5C shows a sagittal cross-section through the intercondylar region 26 including the spine 36 of the tibial bearing component 14. FIG. 5C shows a comparison of the intercondylar region 26 overlaid with the corresponding intercondylar regions of component 60 and component 62. As shown in FIG. 5C, an anterior facing surface 72 of the spine 36 for the tibial bearing component 14 can be disposed rearward of the comparable surface of components 60 and 62.

Figure 6:
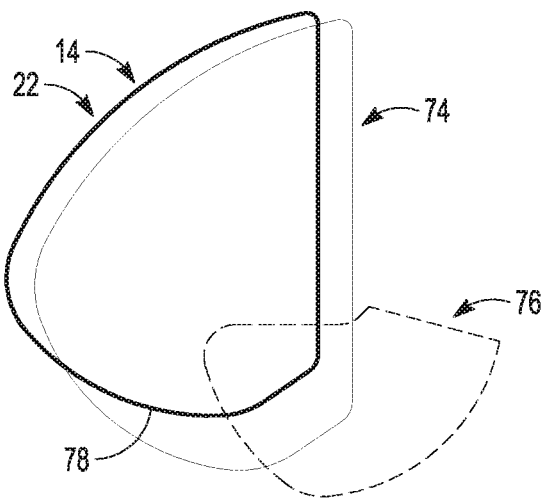
FIG. 6 shows a view in a sagittal plane extending through the cam showing an outline of shape of the cam for various tibial bearing components including the femoral prostheses of FIG. 2 in comparison with two commercially available femoral prostheses of similar size according to one example of the present application.

FIG. 6 shows a sagittal cross-section through the cam 22 of the femoral prosthesis 22. FIG. 6 shows a comparison of the cam 22 overlaid with the corresponding cams of components 74 and 76 (femoral prostheses designed to be operably used with component 60 and component 62, respectively). As shown in FIG. 6, the cam 22 can have a reduced cross-sectional area and a surface 78 of the cam 22 for the femoral prosthesis 12 that is configured to make contact with the spine can be disposed rearward of the comparable surface of components 74 and 76.

FIGS. 7A-8B illustrate the femoral prosthesis 12 and the tibial bearing component 14 previously discussed and illustrated can provide for a more stable medial condyle in terms of laxity ranges. A sizing scheme is presented in FIG. 10 for sizing various of the tibial bearing components and femoral prostheses of the respective families in a manner such that they can be used in combination to better achieve the desired more stable medial condyle.

Figure 7A:
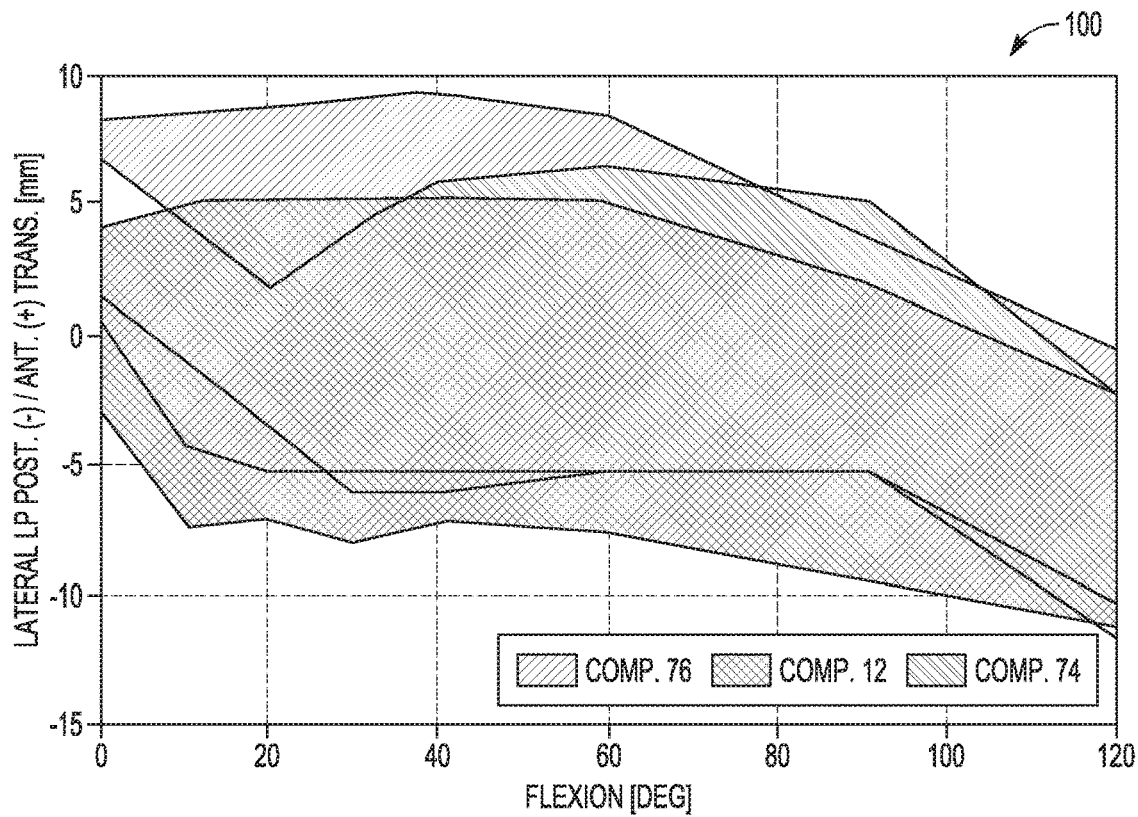
FIGS. 7A and 7B illustrate laxity envelopes and allowable anterior-posterior translation of the femoral prosthesis with the tibial bearing component of FIG. 2 as compared with the two commercially available femoral prosthesis and tibial bearing component systems in accordance with an example of the present application.
Figure 7B:
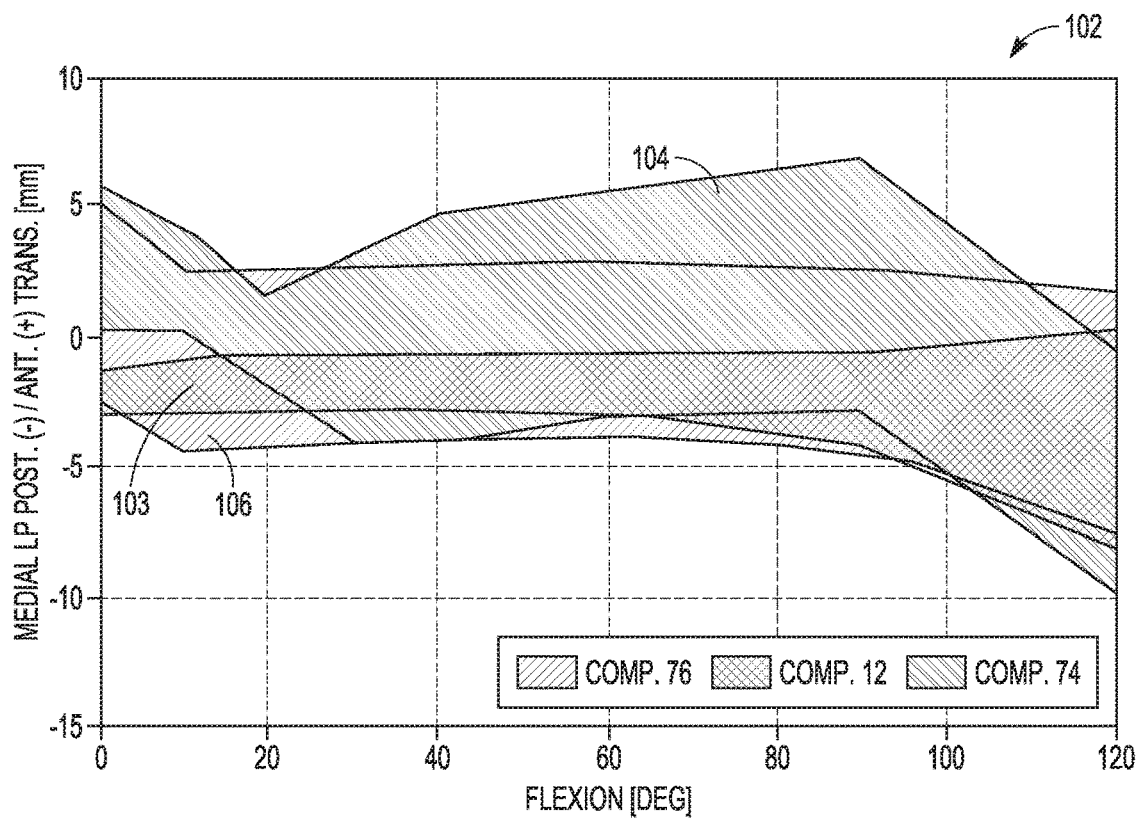

In FIGS. 7A and 7B, the femoral prosthesis 12 (indicated as Comp. 12) in particular the lateral condyle (FIG. 7A) and the medial condyle (FIG. 7B) are illustrated having different average anterior-posterior laxity from 0° to 120° flexion as shown in the graphs of FIGS. 7A and 7B, the laxity can comprise a degree of change in the anterior-posterior position (under various applied load scenarios) of the lateral condyle and the medial condyle plotted against degrees of flexion of the femoral prosthesis. The graph 100 of FIG. 7A and graph 102 of FIG. 7B, are plots of the lateral condyle and the medial condyle, respectively, for the posterior stabilized femoral component 12 (Comp. 12) articulating through the range of motion with the tibial bearing component previously illustrated and discussed. As exhibited by the graph 102 of FIG. 7B the medial condyle when used with the tibial bearing component's medial compartment can be relatively more stabilized (has a tighter laxity area 103 as indicated) when measured against commercially available PS knee system designs (as indicated by areas 104 and 106 of FIG. 7B), where area 104 indicates the envelope for a PS femoral prosthesis (previously illustrated and described as component 74) and tibial bearing component (previously illustrated and described as component 60) of the Persona® knee system and area 106 comprises the laxity of the components 62 and 76 used in combination.

Figure 8A:
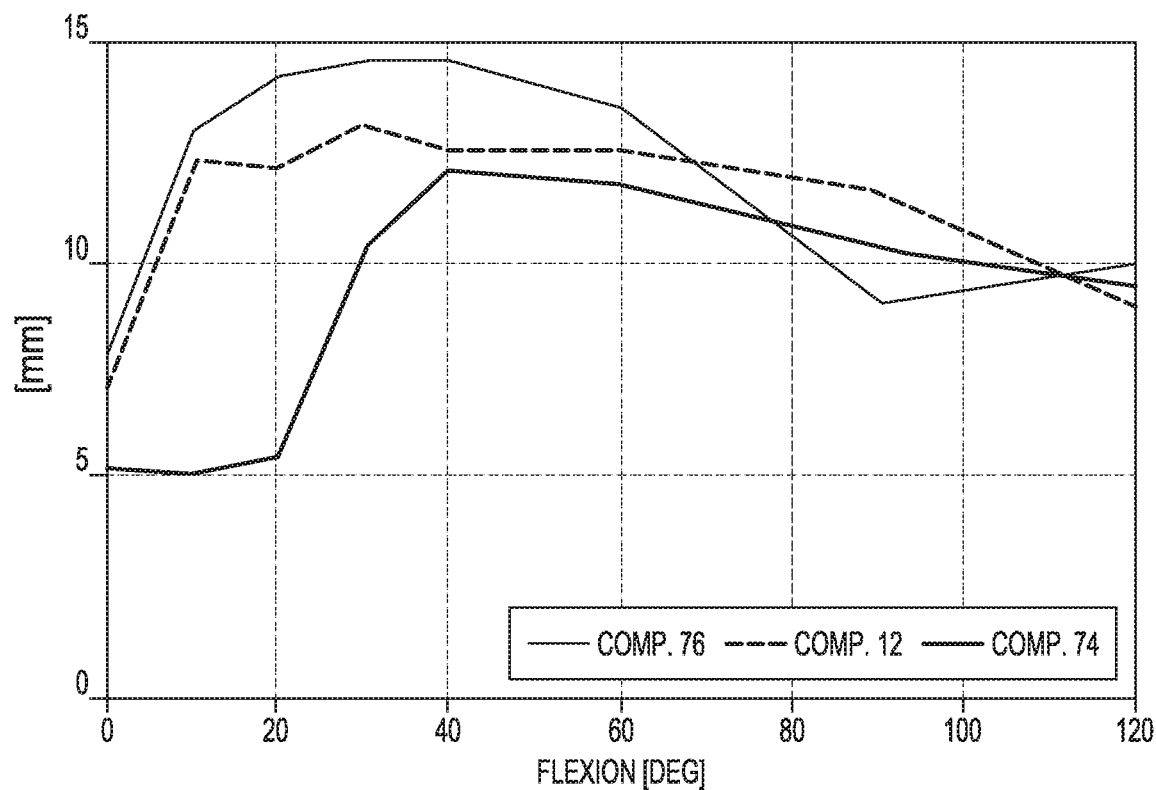
FIGS. 8A and 8B illustrate a width of the laxity envelopes of the femoral prosthesis with the tibial bearing component of FIG. 2 as compared with the two commercially available femoral prosthesis and tibial bearing component systems in accordance with an example of the present application.
Figure 8B:
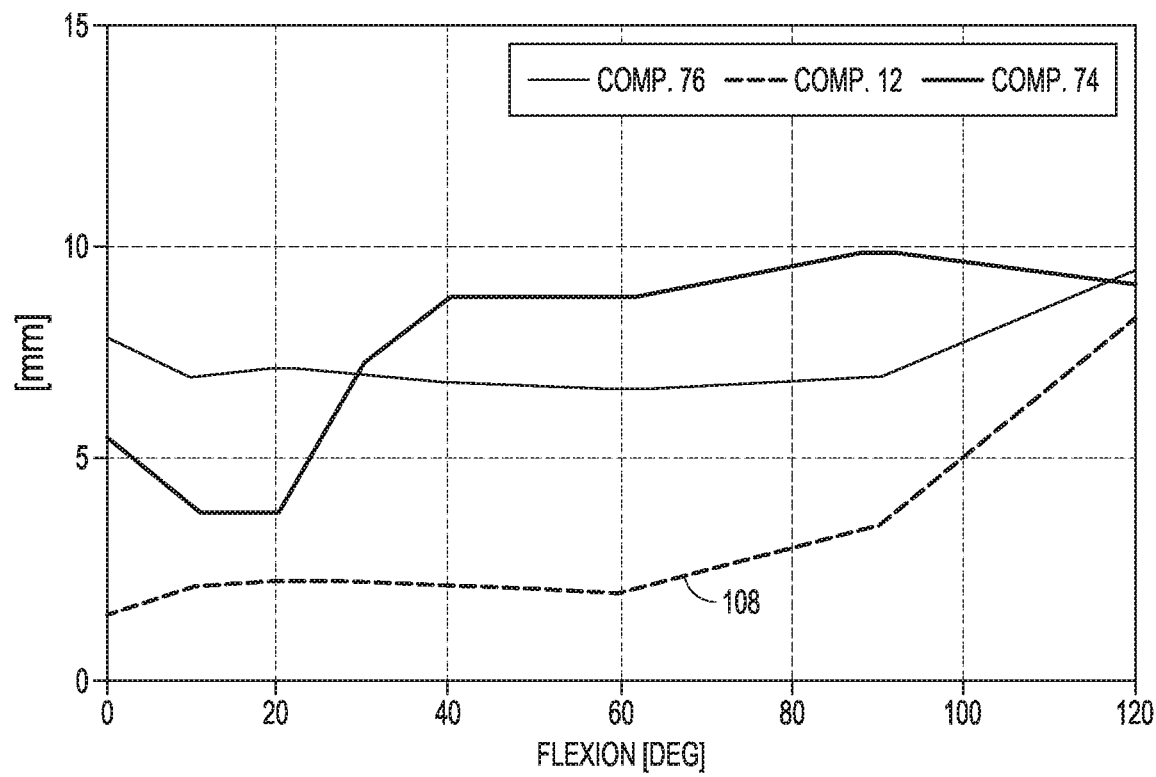

FIGS. 8A and 8B show the average width of the laxity range for the various systems of FIGS. 7A and 7B. Again, in FIG. 8B, the average width of the laxity range indicated by line 108 for the medial condyle of the femoral prosthesis (Comp. 12) with the medial compartment of the tibial bearing component as previously shown and described is lower than that of the other commercially available systems previously described in reference to FIGS. 7A and 7B.

Figure 9:
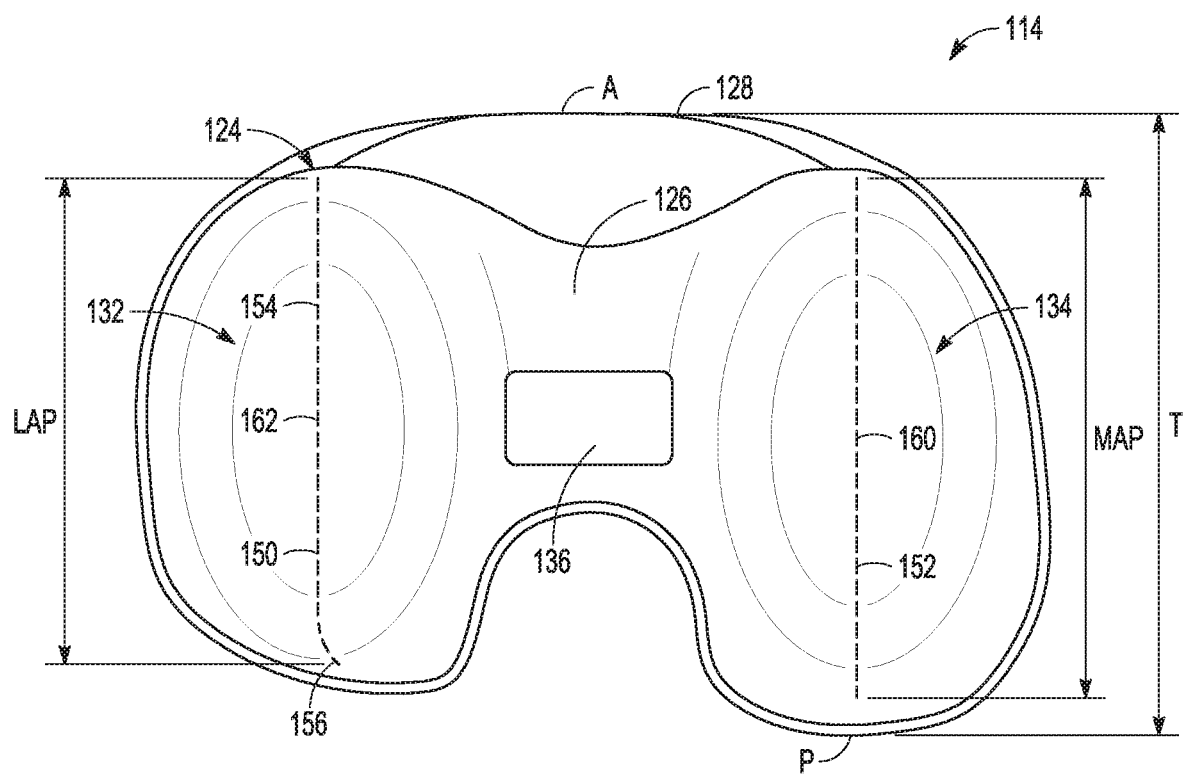
FIG. 9 is a plan view of a proximal surface of the tibial bearing component as previously disclosed further illustrating features such as the spine, the medial compartment and the lateral compartment in accordance with an example of the present application.

FIG. 9 is a plan view of a proximal portion of a tibial bearing component 114 according to an example of the present application. Tibial bearing component 114 can be substantially similar to tibial bearing component 14 previously described herein. However, FIG. 9 adds further detail regarding aspects of the construction of the tibial bearing component 114. As shown in FIG. 9, the tibial bearing component 114 can include an articular surface 124, an intercondylar region 126, a periphery 128, a lateral compartment 132, a medial compartment 134 and a spine 136.

As previously described, the articular surface 124 can be contacted by the femoral condyles (not shown) when operably assembled in the knee. The condyles of the femoral prosthesis can contact the medial and lateral compartments 134, 132. More particularly, the medial compartment 134 and the lateral compartment 132 can be configured (e.g. are dish shaped) for articulation with the medial condyle and the lateral condyle of the femoral prosthesis 12, respectively (as shown in FIG. 2 and further shown in FIG. 11). The periphery 128 can comprise sidewalls connecting with the distal surface (not shown) and the articular surface 124. The medial compartment 134 can differ in configuration from the lateral compartment 132 as will be explained in further detail subsequently. For example, the medial compartment 134 can have a different size and shape relative to the lateral compartment 132. For example, the anterior-posterior curvature of the lateral compartment 132 can differ from that of the medial compartment 134. A position of a medial dwell point for the medial compartment 134 can differ than a lateral dwell point for the lateral compartment 132.

As shown in the example of FIG. 9, the lateral compartment 132 can have a lateral articular track 150 having a lateral anterior-posterior extent $L_{AP}$. The lateral articular track 150 can comprise a plurality of distal-most points along the proximal surface of the lateral compartment 132 that are contacted by the lateral femoral condyle during rollback of the femoral prosthesis. Similarly, the medial compartment 134 can have a medial articular track 152 having a medial anterior-posterior extent MAP that differs from the lateral anterior-posterior extent $L_{AP}$. The medial articular track 152 can comprise a plurality of distal-most points along the proximal surface of the medial compartment 134 that are contacted by the medial femoral condyle during rollback of the femoral prosthesis.

As shown in FIG. 9, in one example the lateral compartment 132 can have an anterior portion 154 and a posterior portion 156. The anterior portion 154 can define the lateral articular track 150 as a nominally straight line when projected onto a transverse plane of the tibial bearing component 114. The posterior portion 156 can define the lateral articular track 150 as a curved line toward the medial compartment 134 when projected onto the transverse plane of the tibial bearing component 114.

In contrast, the medial articular track 152 can define a nominally straight line when projected onto the transverse plane of the tibial bearing component 114, and the medial articular track 152 defined by the medial compartment 134 can be comprised of a uniform single curve. The nominally straight line that can be defined by the medial articular track 152 can be substantially parallel to the nominally straight line defined by the anterior portion 154 of the lateral articular track 150 in some cases.

For convenience, the present discussion refers to points, tracks or lines of contact between tibial bearing component 114 and the femoral prosthesis along the articular tracks 150, 152. However, it is of course appreciated that each potential point or line of contact (i.e., any of the points along one of the articular tracks 150, 152) is not truly a point or line, but rather an area of contact. These areas of contact may be relatively larger or smaller depending on various factors, such as prosthesis materials, the amount of pressure applied at the interface between tibial bearing component 114 and femoral prosthesis, relative shapes of the tibial bearing component 114 relative to the femoral prosthesis, and the like. Moreover, it is appreciated that some of the factors affecting the size of the contact area may change dynamically during prosthesis use, such as the amount of applied pressure at the femoral/tibial interface during walking, climbing stairs or crouching, for example. For purposes of the present discussion, a contact point may be taken as the point at the geometric center of the area of contact. The geometric center, in turn, refers to the intersection of all straight lines that divide a given area into two parts of equal moment about each respective line. Stated another way, a geometric center may be said to be the average (i.e., arithmetic mean) of all points of the given area. Similarly, a line or track is the central line of contact passing through and bisecting an elongate area of contact.

Both the medial compartment 134 and the lateral compartment 132 can include dwell points comprising the medial dwell point 160 and the lateral dwell point 162, respectively. The medial and lateral dwell points 160 and 162 can comprise a distal-most point along the medial articular track 152 and the lateral articular track 150, respectively. As shown in TABLE 1 below, the medial compartment 134 can be configured to have the medial dwell point 160 a distance between about 52% and about 60% of a total anterior-posterior extent T of the tibial bearing component 114 as measured from an anterior most point A of the tibial bearing component 114 to a posterior most point P of the tibial bearing component 114.

TABLE 1

With Anterior Slope 0°

| | Name | % of A/P Dwell point to overall Medial A/P |
|---|---|---|
| PS | 1-2/AB | 52% |
| | 3-6/AB | 52% |
| | 1-2/CD | 58% |
| | 3-9/CD | 57% |
| | 3-11/EF | 58% |
| | 7-12/GH | 60% |
| | 9-12/J | 60% |

TABLE 2

With Anterior Slope 0°

| | Name | % of A/P Dwell point to overall Lateral A/P |
|---|---|---|
| PS | 1-2/AB | 60% |
| | 3-6/AB | 59% |
| | 1-2/CD | 62% |
| | 3-9/CD | 61% |
| | 3-11/EF | 62% |
| | 7-12/GH | 60% |
| | 9-12/J | 64% |

As shown in TABLE 2, the lateral compartment 132 can be configured to have the lateral dwell point 162 a distance between about 59% and about 62% of the total anterior-posterior extent T of the tibial bearing component 114 as measured from the anterior most point A to the posterior most point P of the tibial bearing component 114.

As shown in FIG. 9 the intercondylar region 126 can comprise an eminence or ridge of the articular surface 124 that can be disposed between the medial and lateral compartments 134, 132. The intercondylar region 126 can extend generally anterior-posterior and can have the spine 136 as previously discussed. Thus, the intercondylar ridge defined by the intercondylar region 126 an be disposed between the medial and lateral dished medial and lateral compartments 134, 132 and occupies the available space therebetween.

The tibial bearing components and the femoral prostheses described herein can each be available as a family of tibial bearing components and a family of femoral prostheses, respectively. The family of tibial prostheses can be of a same design class (e.g., be shaped to be PS) and can have different stock sizes (e.g., from use with a small stature tibial component size A to a largest size J). Similarly, the family of femoral prostheses can be a same design class (e.g., be shaped to articulate with a posterior stabilized configured tibial bearing component) and can have different stock sizes (e.g., from a small stature size 1 to a largest size 12). Different sizes of tibial bearing components can be used depending on the size of the femoral prosthesis and the tibial prosthesis selected.

FIG. 10 shows a sizing chart for the family of tibial prostheses 200 relative to the family of femoral prostheses 202. More particularly, the sizing chart shows the family of femoral prostheses 202 can have at least twelve different stock sizes 1 to 12. As previously discussed and illustrated, each femoral prosthesis can be of a same design class PS and can include a medial condyle and a lateral condyle. The family of tibial prostheses 200 can have at least nine different stock sizes A to J. As shown in FIG. 10, the family of tibial bearing components 204 can be configured such that at least eleven stock sizes exist and that combinations of the at least nine different stock sizes of the family of tibial prostheses 200 are compatible for operable use (e.g. to facilitate a desired articulation similar to that of a natural knee) with the at least twelve different stock sizes of the family of femoral prostheses 202.

This overlapping sizing and the provision of many different compatible sizes can have benefits including providing for increased stability of the medial condyle of the femoral prosthesis. For example, by having a family of tibial bearing components that can include at least eleven different stock sizes and a family of femoral prostheses that can include at least twelve different stock sizes with thirty three different possible operable combinations.

Furthermore, having overlapping sizing and the provision of many different compatible sizes (alone and/or in addition to shaping the compartments to better conform with the condyles using aspects previously discussed) can provide for an increased contact area between the medial condyle of the femoral prosthesis and the medial compartment of the tibial bearing component. As a result, the femoral prosthesis can have greater stability with respect to the medial condyle.

A medial conformity between the femoral prosthesis and the tibial bearing component can be between about 1.05:1 and about 1.5:1 through the first angular extent (previously discussed in reference to FIG. 3A). Put another way, the medial compartment is configured to have between about a 1.05:1 congruence ratio and about a 1.5:1 congruence ratio with the medial condyle through the first angular extent. "Conformity," (also referred to as "congruence" or "congruence ratio" in the context of knee prostheses, refers to the similarity of curvature between the convex femoral condyles and the correspondingly concave tibial articular compartments in the sagittal plane. Thus, the conformity ratio can comprise a ratio of the similarity between a sagittal radius of the medial tibial bearing compartment and a sagittal radius of the medial femoral condyle.

Figure 11:
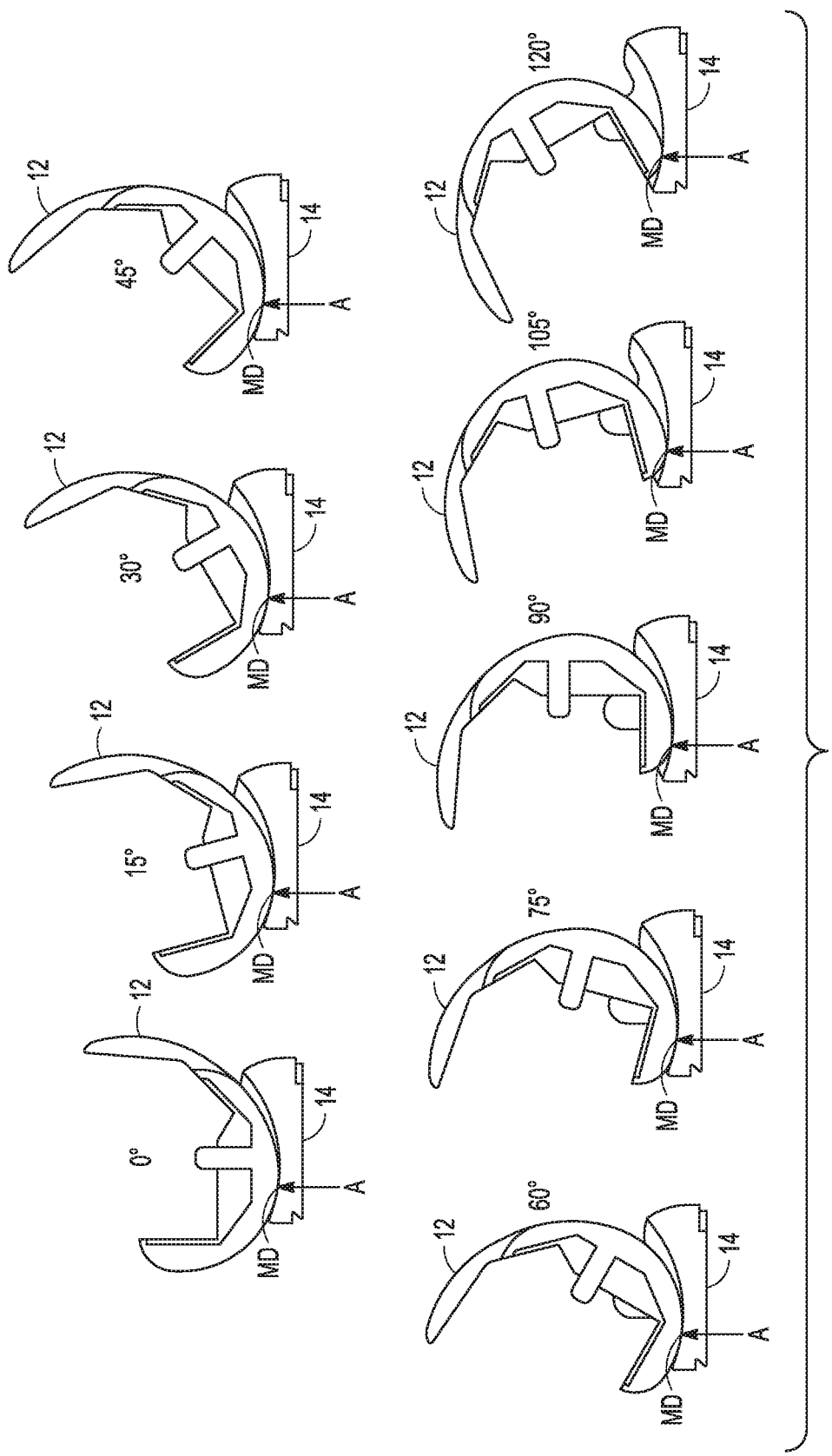
FIG. 11 shows sagittal views illustrating contact areas as indicated by arrows between the medial femoral condyle of the femoral prosthesis and the medial compartment of the tibial bearing component shown at different degrees of flexion of the femoral prosthesis relative to the tibial bearing component in accordance with an example of the present application.

FIG. 11 shows articulation of the femoral prosthesis 12 with the tibial bearing component 14 through a range of motion between 0 degrees and 120 degrees flexion. Recall 0 degrees flexion comprises full extension as previously discussed and positive flexion corresponds to greater than zero degrees flexion of the knee joint. As indicated by arrows A in FIG. 11, an area of contact between the medial condyle and the medial compartment does not shift position during the range of motion between zero degrees flexion and substantially 100 degrees flexion. Furthermore, the area of contact (as indicated by arrow A) includes the medial dwell point MD of the tibial articular surface during the range of motion between zero degrees flexion and substantially 100 degrees flexion. Thus, the area of contact includes the medial dwell point MD of the tibial articular surface when the femoral prosthesis 12 is in full extension. Recall from prior discussion that the spine and cam can make initial contact when the range of motion reaches substantially 100 degrees flexion with the anterior-posterior slope of the tibial bearing component of five degrees, when such initial contact occurs the area of contact (indicated as arrow A) can begin to shift position and can move off the medial dwell point MD as shown in reference to the image where the femoral prosthesis has been articulated to 120 degrees flexion.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

As used herein the terms "substantially" or "about" means within two percent of a referenced value, within two degrees of the reference value, within 0.1 mm or less of the reference value, or the like, whatever, context best applies.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) can be used in combination with each other. Other examples can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above detailed description, various features can be grouped together to streamline the disclosure. This should not be interpreted as intending that an unclaimed disclosed feature is essential to any claim. Rather, inventive subject matter can lie in less than all features of a particular disclosed example. Thus, the following claims are hereby incorporated into the detailed description as examples or embodiments, with each claim standing on its own as a separate example, and it is contemplated that such examples can be combined with each other in various combinations or permutations. The scope of the invention The claimed invention is:

1. A posterior-stabilized femoral prosthesis for a knee arthroplasty comprising:
   medial and lateral condyles shaped to articulate with a tibial articular surface of a tibial bearing component through a range of motion, in which full extension corresponds to zero degrees flexion of a knee joint and positive flexion corresponds to greater than zero degrees flexion of the knee joint, wherein in a sagittal plane the medial and lateral condyles define medial and lateral multi-radius curves, respectively, and wherein the medial multi-radius curve includes a single common radius swept through a first angular extent to define a single arc; and
   a femoral cam and a recess positioned between the medial and lateral condyles, wherein the femoral cam is positioned posterior of the recess, wherein an area of contact between the medial condyle and the tibial articular surface includes a medial dwell point of the tibial articular surface when the femoral prosthesis is in full extension, wherein the area of contact between the medial condyle and the tibial articular surface does not shift position during the range of motion encompassing at least a majority of the single arc;
   wherein a medial compartment of the tibial articular surface is configured to have between about a 1.05:1 congruence ratio and about a 1.5:1 congruence ratio with the medial condyle through the first angular extent, the congruence ratio comprising a ratio of a similarity between a sagittal radius of the medial compartment and a sagittal radius of the medial condyle.

2. The prosthesis of claim 1, wherein the single arc extends from between substantially −20 degrees flexion to substantially 90 degrees flexion, inclusive.

3. The prosthesis of claim 2, wherein the area of contact between the medial condyle and the tibial articular surface does not shift position during the range of motion between zero degrees flexion and substantially 100 degrees flexion.

4. The prosthesis of claim 1, wherein a posterior portion of the medial and lateral condyles have a thickness of 9 mm.

5. The prosthesis of claim 1, further comprising the tibial bearing component defining the tibial articular surface, the tibial articular surface including:
   the medial compartment and a lateral compartment configured for articulation with the medial condyle and the lateral condyle of the femoral prosthesis, respectively; and
   a spine extending proximally from the articular surface and configured to be received in the recess at 0 degrees flexion, the spine spaced posteriorly from an anterior edge of a tibial bearing periphery, the spine disposed between the medial and lateral compartments;
   wherein the spine and cam make initial contact when the range of motion reaches 100 degrees flexion.

6. The prosthesis of claim 1, wherein the medial compartment is configured to have the medial dwell point a distance between about 52% and about 60% of a total anterior-posterior extent of the tibial bearing component as measured from an anterior most point to a posterior most point of the tibial bearing component.

7. The prosthesis of claim 1, wherein a lateral compartment of the tibial articular surface is configured to have a lateral dwell point a distance between about 59% and about 62% of a total anterior-posterior extent of the tibial bearing component as measured from an anterior most point to a posterior most point of the tibial bearing component.

8. A system of posterior-stabilized knee prostheses for a knee arthroplasty, the system comprising:
   a tibial bearing component having a tibial articular surface with a medial compartment and a lateral compartment, wherein the tibial bearing component has a spine extending proximally from the tibial articular surface and positioned between the medial and lateral compartments, and wherein the medial compartment has a medial dwell point;
   a femoral prosthesis having a cam and medial and lateral condyles spaced to either side of the cam, wherein the medial condyle is configured for articulation with the medial compartment and lateral condyle is configured for articulation with the lateral compartment, and wherein femoral prosthesis is configured to articulate through a range of motion relative to the tibial bearing component, such range of motion includes a full extension that corresponds to zero degrees flexion of a knee joint and positive flexion that corresponds to greater than zero degrees flexion of the knee joint, and wherein an area of contact between the medial condyle and the medial compartment does not shift position during the range of motion between zero degrees flexion and substantially 100 degrees flexion and the area of contact includes the medial dwell point during the range of motion between zero degrees flexion and substantially 100 degrees flexion.

9. The system of claim 8, wherein in a sagittal plane the medial and lateral condyles define medial and lateral multi-radius curves, respectively, and wherein the medial multi-radius curve includes a single common radius swept through a first angular extent to define a single arc length that extends from between substantially −20 degrees flexion to substantially 90 degrees flexion, inclusive.

10. The system of claim 8, wherein a posterior portion of the medial and lateral condyles have a thickness of 9 mm.

11. The system of claim 8, wherein the spine and cam are both configured to make initial contact when the range of motion reaches 100 degrees flexion.

12. The system of claim 8, wherein the medial compartment is configured to have the medial dwell point a distance between about 52% and about 60% of a total anterior-posterior extent of the tibial bearing component as measured from an anterior most point to a posterior most point of the tibial bearing component, and wherein the lateral compartment is configured to have a lateral dwell point a distance between about 59% and about 62% of a total anterior-posterior extent of the tibial bearing component as measured from an anterior most point to a posterior most point of the tibial bearing component.

13. The system of claim 8, wherein the medial compartment is configured to have between about a 1.05:1 congruence ratio and about a 1.5:1 congruence ratio with the medial condyle through a first angular extent, the congruence ratio comprising a ratio of similarity between a sagittal radius of the medial compartment and a sagittal radius of the medial condyle.

14. A system of posterior-stabilized knee prostheses for a knee arthroplasty, the system comprising:
   a tibial bearing component having a tibial articular surface with a medial compartment and a lateral compartment, wherein the tibial bearing component has a spine extending proximally from the tibial articular surface and positioned between the medial and lateral compartments, and wherein the medial compartment has a medial dwell point;

a femoral prosthesis having a cam and medial and lateral condyles spaced to either side of the cam, wherein the medial condyle is configured for articulation with the medial compartment and lateral condyle is configured for articulation with the lateral compartment, and wherein femoral prosthesis is configured to articulate through a range of motion relative to the tibial bearing component, such range of motion includes a full extension that corresponds to zero degrees flexion of a knee joint and positive flexion that corresponds to greater than zero degrees flexion of the knee joint, wherein an area of contact between the medial condyle and the medial compartment includes the medial dwell point when the femoral prosthesis is in full extension, and wherein the spine and cam are both configured to make initial contact when the range of motion reaches substantially 100 degrees flexion;

wherein in a sagittal plane the medial and lateral condyles define medial and lateral multi- radius curves, respectively, and wherein the medial multi-radius curve includes a single common radius swept through a first angular extent to define a single arc, wherein the area of contact between the medial condyle and the tibial articular surface does not shift position during the range of motion encompassing at least a majority of the single arc.

15. The system of claim 14, wherein the area of contact between the medial condyle and the tibial articular surface does not shift during the range of motion between zero degrees flexion and substantially 100 degrees flexion and includes the medial dwell point during the range of motion between zero degrees flexion and substantially 100 degrees flexion.

16. The system of claim 14, wherein the medial compartment is configured to have the medial dwell point a distance between about 52% and about 60% of a total anterior-posterior extent of the tibial bearing component as measured from an anterior most point to a posterior most point of the tibial bearing component.

17. The system of claim 14, wherein a posterior portion of the medial and lateral condyles have a thickness of 9 mm.

18. The system of claim 14, wherein the single arc extends from between substantially −20 degrees flexion to substantially 90 degrees flexion, inclusive.

19. The system of claim 14, wherein the medial compartment is configured to have between about a 1.05:1 congruence ratio and about a 1.5:1 congruence ratio with the medial condyle through the first angular extent, the congruence ratio comprising a ratio of a similarity between a sagittal radius of the medial compartment and a sagittal radius of the medial condyle.

* * * * *